United States Patent
Tam et al.

(10) Patent No.: US 10,114,931 B2
(45) Date of Patent: Oct. 30, 2018

(54) PHARMACEUTICAL PLATFORM TECHNOLOGY FOR THE DEVELOPMENT OF NATURAL PRODUCTS

(71) Applicant: Sinoveda Canada Inc., Edmonton, Alberta (CA)

(72) Inventors: Yun Kau Tam, Edmonton (CA); Jack Adam Tuszynski, Edmonton (CA)

(73) Assignee: SINOVEDA CANADA INC. (CA)

( * ) Notice: Subject to any disclaimer, the term of this patent is extended or adjusted under 35 U.S.C. 154(b) by 529 days.

(21) Appl. No.: 14/327,529

(22) Filed: Jul. 9, 2014

(65) Prior Publication Data

US 2014/0348963 A1   Nov. 27, 2014

Related U.S. Application Data

(63) Continuation of application No. 12/174,412, filed on Jul. 16, 2008, which is a continuation-in-part of application No. PCT/IB2008/001401, filed on Mar. 31, 2008.

(60) Provisional application No. 60/909,018, filed on Mar. 30, 2007.

(51) Int. Cl.
G06F 19/00 (2018.01)
G06K 9/62 (2006.01)
A61K 36/48 (2006.01)
G06F 19/12 (2011.01)
C40B 30/02 (2006.01)

(52) U.S. Cl.
CPC ............ G06F 19/704 (2013.01); A61K 36/48 (2013.01); C40B 30/02 (2013.01); G06F 19/12 (2013.01); G06K 9/6228 (2013.01)

(58) Field of Classification Search
None
See application file for complete search history.

(56) References Cited

U.S. PATENT DOCUMENTS

| | | | |
|---|---|---|---|
| 2004/0132633 A1 | 7/2004 | Carter | |
| 2004/0138826 A1* | 7/2004 | Carter et al. | 702/27 |
| 2004/0203043 A1* | 10/2004 | Scott | 435/6 |
| 2005/0089923 A9 | 4/2005 | Levinson et al. | |
| 2006/0136140 A1 | 6/2006 | Perschke et al. | |

OTHER PUBLICATIONS

Ei-Masri, H. A., Reardon, K. F. & Yang, R. S. H. Integrated Approaches for the Analysis of Toxicologic Interactions of Chemical Mixtures. Crit. Rev. Toxicol. 27, 175-197 (1997).*

(Continued)

*Primary Examiner* — Soren Harward
(74) *Attorney, Agent, or Firm* — Law Offices of Albert Wai-Kit Chan, PLLC

(57) ABSTRACT

The present invention provides a set of in vitro and in silico methodologies for predicting in vivo pharmacokinetics and pharmacodynamics of multiple components; the methodologies comprise mathematical models for solving multiple unknowns which are linearly independent and/or interacting with each other. The present invention can be applied to develop phytomedicines which contain multiple active ingredients without prior identification, isolation and purification of these components.

7 Claims, 36 Drawing Sheets

(56) References Cited

OTHER PUBLICATIONS

Xue, L., Godden, J., Gao, H. & Bajorath, J. Identification of a Preferred Set of Molecular Descriptors for Compound Classification Based on Principal Component Analysis. J. Chem. Inf. Comput. Sci. 39, 699-704 (1999).*
Chen, V. C. P., Tsui, K.-L., Barton, R. R. & Meckesheimer, M. A review on design, modeling and applications of computer experiments. IIE Transactions 38, 273-291 (2006).*
U.S. Office Action, dated Apr. 25, 2011, for U.S. Appl. No. 12/174,412, filed Jul. 16, 2008.
U.S. Office Action, dated Aug. 1, 2011, for U.S. Appl. No. 12/174,412, filed Jul. 16, 2008.
U.S. Office Action, dated Feb. 16, 2012, for U.S. Appl. No. 12/174,412, filed Jul. 16, 2008.
U.S. Office Action, dated Aug. 28, 2013, for U.S. Appl. No. 12/174,412, filed Jul. 16, 2008.
U.S. Office Action, dated Mar. 18, 2014, for U.S. Appl. No. 12/174,412, filed Jul. 16, 2008.
Cohen Ira et al., 2002.
Huang X et al., 2004, J Chromatogr B, vol. 812:71-84.
Krzanowski W.J. et al., 1987, App Stat, vol. 36:22-23.
Lavine B.K. and Workman J., 1998, Anal Chem, vol. 70:209-228.
Li H., 2006, Drug Dev Res, vol. 66:245-259.
Su X., 2007, Mini Rev Med Chem, vol. 7:89-98.
Sumathi S. and Sivanandam S.N., 2006, Studies in Computational Intelligence, vol. 29.
Kincl et al., 2005, Int. J. Pharm, vol. 291:39-49.
Kong and Lee, 2006, Biometrics, vol. 62:986-95.
Sastry et al., 1997, J. Control. Release, vol. 45:121-130.
Ridgway et al., "Reassessing Models of Hepatic Extraction," Journal of Biological Physics, Mar. 2003, vol. 29 (1), pp. 1-21.

* cited by examiner

PHARMACEUTICAL PLATFORM TECHNOLOGY FOR THE DEVELOPMENT OF NATURAL PRODUCTS

This application is a continuation application of U.S. application Ser. No. 12/174,412, filed Jul. 16, 2008, which is a continuation-in-part of International App'l No. PCT/IB2008/001401, filed Mar. 31, 2008, which claims benefit of U.S. Ser. No. 60/909,018, filed Mar. 30, 2007. The entire contents and disclosures of the preceding applications are incorporated by reference into this application.

Throughout this application, various references are referred to and disclosures of these publications in their entireties are hereby incorporated by reference into this application to more fully describe the state of the art to which this invention pertains.

BACKGROUND OF THE INVENTION

Natural products have been used by the human civilization for thousands of years. Their medicinal values have been recorded throughout history. Since the advancement of pharmacology, clinical pharmacology, pharmacognosy and analytical chemistry, the active components in a natural substance were beginning to be unveiled. A good example is the discovery of acetylsalicylic acid in willow bark. Bayer has recently celebrated the 100$^{th}$ anniversary of Aspirin, a purified form of acetylsalicylic acid.

There are two streams of natural product research. Since the dawn of modern pharmaceutical sciences, there has been an insatiable quest for the isolation and purification of a single active component in a natural substance. In fact, more than 60% of the pharmaceuticals which have been developed for treating cancer, hypertension and migraine are either natural in origin or natural product mimics (Newman et al., 2003). Although combinatorial techniques have succeeded as methods of optimizing structures, no de novo combinatorial compound approved as a drug has been identified on or before 2002. In hope of finding new core chemical structures, efforts are still being spent in natural product research.

Natural remedies are often composed of one or more herbs. Each herb has multiple active components. The identification, purification, activity determination, using known pharmacological models for a complex mixture, has been a monumental task. The complexity of this area of research has been the major obstacle in natural medicine development (Williamson, 2001). In his review, Liu and Yang (2006) commented that identifying active components in traditional Chinese Medicine (TCM) is the most important issue in the development of TCM. The active components could be active metabolites of the principle components of the preparation. For example, ginsenosides are major components responsible for the efficacy of ginseng. However, the activity of these ginsenosides is low and their bioavailability after oral administration is minuscule. The metabolic products, protopanaxadiols and protopanaxatriols are easily absorbed and pharmacologically active (Hasegawa, 2004). Although it is important to understand the pharmacokinetic and pharmacodynamic nature of the active components in TCM, there was no suggestion for sorting out the complicated interrelationships between potential pharmacokinetic and pharmacodynamic interactions.

The study of active ingredients in natural substances has been rather primitive in pharmaceutical sciences terms. The approach is stagnated at the discovery stage of pharmaceutical development. The general approach is to employ activity guided extraction to identify targets that have in vitro activities. This approach is extremely unsuitable for the development of nature products. For the longest time, *Panax ginseng* was thought to be an expensive "junk" because it has no apparent active ingredients. It was not until Hasegawa (2004) reported that the inactive ginsenosides of *Panax ginseng* were acting like prodrugs, when metabolized by intestinal flora release the aglycones, which have physiological activity. Rutin, a flavonoid glycoside, which is present in *ginkgo* and a number of other herbs, has been shown to be a potent antioxidant in vitro. However, it is difficult to substantiate the actual in vivo activity of rutin, simply because this substance is not detected in the blood stream (Hollman et al., 1997). A major component of Chuanxiong, z-ligustilide, has been shown to be a major active component of the herb; however, the bioavailability of this component is less than 3% (Yan et al., 2008). It is quite obvious that there will not be enough ligustilide reaching the site of action to exert its activity. These examples clearly show the shortcoming of using the classical pharmaceutical approach of identifying actives in an herbal preparation. The natural prodrugs, like that of ginsenosides, will be missed and actives like rutin will be pursued. In pharmaceutical science terms, compounds like ligustilide lacks drug-like properties for oral administration. Drug-like properties are basically pharmacokinetic properties of a substance which, after administration, has the ability to be absorbed in a substantial amount without being metabolized, and to be distributed via the blood stream to the site of action in sufficient quantity before being eliminated from the body. It is no surprise that drug-like properties have not been a major component of natural product research because it is new to the pharmaceutical development. Since there are permutations in arriving at the actives of an herbal extract, the complexity of delineating pharmacokinetic profiles for multi-components does appear to be prohibitive.

Recognizing the complex nature of herbal product development, Homma et al. (1992) proposed a strategy to discover biologically active components in an herbal product. The premise of the strategy is that ingredients and/or their metabolites have to be absorbed before they can exert their biological effects. Contents in plasma and urine after product administration were measured. This approach has been employed by Pan and Cheng (2006) to evaluate a Chinese herbal product, Shuangdan. It was proposed that some of the components that were present in plasma could be used for standardization of the product. This approach can certainly be used to identify absorbable components and their metabolites. Zhang et al. (2005) examined using chemical and metabolic fingerprinting for identifying potentially active ingredients in Danshen injection batches.

The advance of analytical technology may complicate this approach because the nature of components present in plasma will be different from that of the product and the number of components present could exceed that of the product because the number of potential metabolites formed could be daunting. One could argue that only the major components needed be standardized; however, this assumption is clearly flawed because potent components present in minute quantities may be missed. Among other shortcomings, this approach to discover biologically active components does not permit optimization of ratio and dosage of biologically active components.

In recent years, interests in performing pharmacological and pharmacokinetic studies on natural substances such as St. John's Wort (Schulz et al., 2005) and Ginkgo (Kwak et al., 2002; Ahlemeyer and Krieglstein, 2003) are increasing.

There is no lack of publications in the area of herb-drug interactions (Brazier and Levine, 2003; Hu et al., 2005; Williamson, 2005), herbal effects on drug metabolizing enzymes (Venkataramanan et al., 2000; Mathews et al., 2002; Komoroski et al., 2004; Yim et al., 2004; Chang et al., 2006) and pharmacokinetics of active ingredients of herbs (Mathews et al., 2005; Zhou et al., 2005; Yan et al., 2007). The latter is limited to a single component. There are studies which attempted to predict in vivo herb-drug interaction using in vitro methodologies (Williamson, 2001; Mohutsky et al., 2006; Venkataramanan et al., 2006). These studies met with partial success and the general conclusion is that an in vivo study is required to confirm the results.

It has been frequently postulated that the advantage of alternative therapy is the relatively low dosage required for the treatment of an ailment (Williamson, 2001). Active components could act either additively, synergistically or antagonistically. This subject remains elusive to scientists working on the development of herbal medicine. Wang et al. (2006) have designed a method called Quantitative Composition-activity Relationship (QCAR) to identify herbs that are active in a multiple herb formula. While individual herbs contain mixtures of compounds, there was no attempt to address the effects of potential variability within each herb on the pharmacological outcome of the formula. Although in vivo interaction between herbs was reported, there were no indications as to which components in each herb were involved. The same group of scientists have also published a method to address the issue faced with mixtures in QCAR (Cheng et al., 2006). However, the active components identified using these methodologies were restricted to activity only; there was no attempt to investigate the "drug-like" properties of active components. Since a large number of herbs contain ingredients that behave like precursors, e.g., ginsenosides from *Panax ginseng*. In their native forms, they are inactive. This method would have missed this category of "active" ingredients. In the absence of an understanding of the number of components/precursors involved and their respective drug-like properties, it would be close to impossible to determine these intricate interactions in the body. The methods developed by this group of scientists were based on linear models. This limitation has restricted the evaluation of interactions, including synergism and antagonism. Furthermore, they do not take the nonlinear relationship between intensity of activity and concentration into account, a relationship that is important for understanding optimal dosing and degree of component-component interaction (Chou, 2006).

Pharmaceutical technologies for drug discovery have not been employed extensively in the development of natural products. There are a number of in vitro microsomal or hepatocyte studies reported for evaluating herb-drug interactions (Hu et al., 2005; Williamson, 2005; Venkataramanan et al., 2006) and metabolism of active components (Komoroski et al., 2005). However, there is no study on using physiologically based pharmacokinetic and/or pharmacodynamic models to predict the time course of active ingredients of an herbal extract in the body, nor are there any studies using the same approach to quantify the time course of a response. No in silico methods to-date employed for drug discovery have been applied to predict pharmacokinetic and pharmacodynamic interaction of active components and their metabolites after administration of an herbal extract.

There are a number of patents filed in the last 20 years outlining methods for standardizing natural products. The most advanced ones are that of Paracelsian's BioFit® (Blumenthal and Milot, 2004), CV Technologies' ChemBioPrint® (Pang et al., 2000) and PharmaPrint Inc's. PharmaPrint® technologies (Khwaja and Friedman, 2000; Khwaja and Friedman, 2002). The later two utilize bioassays involving concentrating fractions that are pharmacologically active and one or more markers are standardized along with desired activities. When both conditions are satisfied, the batch is accepted. PharmaPrint® rates these extracts pharmaceutical grade. They have used this technology to produce standardized herbs such as St. John's Wort (Khwaja and Friedman, 2000). ChemBioPrint® appears to be a bit more involved in that in addition to the in vitro assays, in vivo assays are also incorporated in the standardization procedures. Neither of these two standardization procedures directly links the activity with the putative standardized ingredients. Therefore, it is not known whether the standardized ingredients are of the right amount or the appropriate ratios. There is also no information on active ingredients that are not identified. It is well known that some of these ingredients are inactive in vitro, but they have biological activities in vivo (Hasegawa, 2004). The reason is that some of these ingredients are not actually absorbed; therefore lacking "drug-like" properties. Paracelsian's BioFit® technology claimed that an absorption assessment using Caco-2 cells were performed on the active components. However, Caco-2 has shortcomings in predicting large molecule absorption because these molecules are not permeable through the Caco-2 membrane. A significant percentage of natural ingredients have large molecular weights. The absorption of these molecules such as polysaccharides, glycosides, etc. is difficult to estimate using Caco-2 cells.

Kinetana's SimBioDAS® technology (Tam and Anderson, 2000) appears to overcome the problems that Caco-2 technology faces (Blumenthal and Milot, 2004). This technology has been employed to measure absorbable components which are active in vitro. This technology, however, has two problems: 1. it does not provide an estimate of the pharmacokinetics of ingredients and therefore, concentration-time profiles at the site of action; and 2. the cell membranes are susceptible to rupture when they are incubated with certain herbal extracts such as St. John's Wort.

There was a news release in January 2008 by an Indian firm Avesthagen announcing a new technology, MetaGrid, for the standardization of multi-constituent plant-based extracts. This technology is based on matching retention times of active components analyzed using an analytical method. While the technology may be useful for standardizing active components, however, these so-called active components have not been subjected to vigorous testing for in vivo testing. In other words this technology does not provide information on the "drug-like" properties of these components.

In short, there is no method available to adequately mine the physiologically active components of an herbal substance. It is generally believed that the activity of phytomedicine is mediated by a large number of active ingredients, each of which constitutes a relatively low quantity compared to those used in Western medicines. Furthermore, each ingredient, if given individually, would require a much higher dose to achieve the same physiological effect. It is believed, however, (while rarely demonstrated directly by experiment) that these individual ingredients, when taken together, may mutually reinforce each other synergistically. For example, in a given herbal extract (e.g. Echinacea or *Ginkgo biloba*), there could be several hundred chemical entities, dozens of which are active compounds and a subset of these can strongly interact with each other synergistically or by mutual inhibition. However, existing technology does not allow stringent quality control because there have been no success in elucidating the activity of these ingredients as a group. In this invention, a platform technology, which is based on formulating a mathematically rigorous procedure of describing these interactions through a combination of in vitro and in silico modelling and data analysis resulting in reverse engineering of the process and then designing an optimal composition in order to yield the most efficacious multi-component formulation, is described. The advantage of this approach is that there is no requirement to study the components individually. As a result, separation, isolation and purification of active components are not necessary; therefore, saving time and resources. FIG. 1 illustrates a model which is used to describe the concentration and effect time course of a single component and this same model can be used for describing the time course of multiple components after incorporating the mathematical procedures described herein.

SUMMARY OF THE INVENTION

Mathematical models for solving multiple unknowns which are linearly independent and/or interacting with each other have been incorporated into a set of in vitro and in silico methodologies for predicting in vivo pharmacokinetics and pharmacodynamics of multiple components. This method is applied to develop phytomedicines which contain multiple active ingredients without prior identification, isolation and purification of these components.

The in vitro techniques include, but are not limited to: incubation with artificial gastric and intestinal juice, intestinal flora, intestinal microsomes, cell membrane, intestinal tissue, hepatocytes, plasma, and blood. In silico techniques include an augmented physiologically based pharmacokinetic/pharmacodynamic model, prediction of log P, log D, volume of distribution and renal excretion.

In one embodiment, the present invention provides a method of predicting in vivo pharmacokinetics and pharmacodynamics of a mixture with multiple components, comprising the steps of: determining the rate of metabolism of individual and interacting components in the mixture in gastrointestinal tract and liver; determining distribution of the components in blood or plasma; determining the rate of the components' renal elimination; and determining the potency of an individual component and synergism or inhibition among the components, wherein the above determinations comprise mathematical models that will predict the pharmacokinetics and pharmacodynamics properties of the mixture in vivo.

In another embodiment, there is also provided a composition comprising multiple components as identified by the method described herein, wherein the components have desirable in vivo pharmacokinetics and pharmacodynamics properties as determined by the method described herein.

DETAILED DESCRIPTION OF THE FIGURES

FIG. 1 shows a schematic describing the fate of a component after oral administration. Inter-compartmental transfer is assumed to be first order, as indicated by the arrows.

FIG. 2A shows a typical dose-response relationship that follows Michaelis-Menton kinetics. FIG. 2B shows the same relationship graphically transformed to depict log dose vs. response. Response is approximately linear related to log dose in the range between 20-80% of maximum.

Figure 6A:
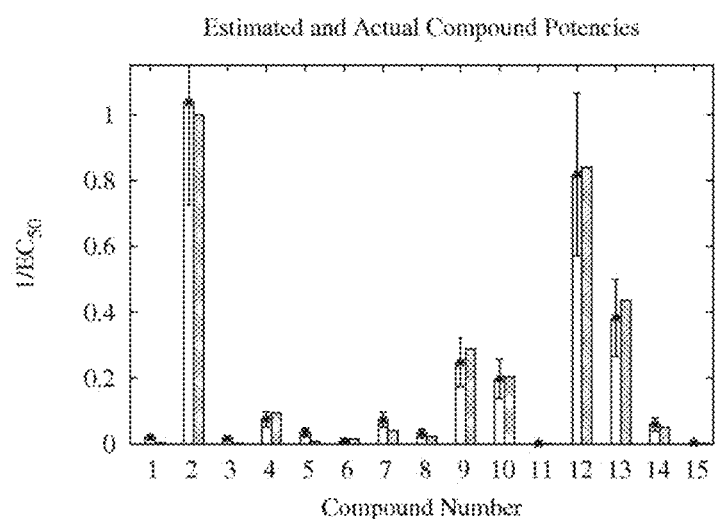
Figure 6B:
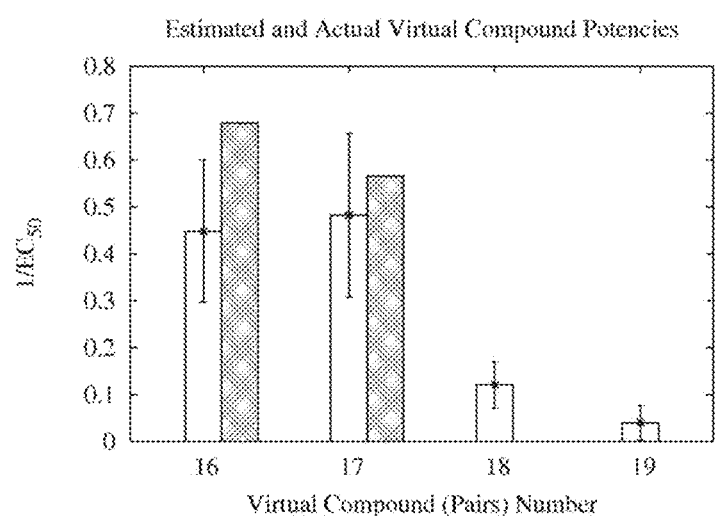

FIGS. 6A and B show predicted (open bars) vs. actual (hatch bars) potencies ($1/EC_{50}$). FIG. 6A: Relative potencies of the 15 hypothetical compounds. Compounds 2, 9, 10, 12 and 13 are predefined to be active (>10% noise). FIG. 6B: Compound 16 (compounds 4 and 10) and 17 (compounds 7 and 8) showed activities higher than the individuals combined. Compounds 18 and 19 are fictitious pairings of compounds 1 and 2; and 3 and 4, respectively.

Figure 7:
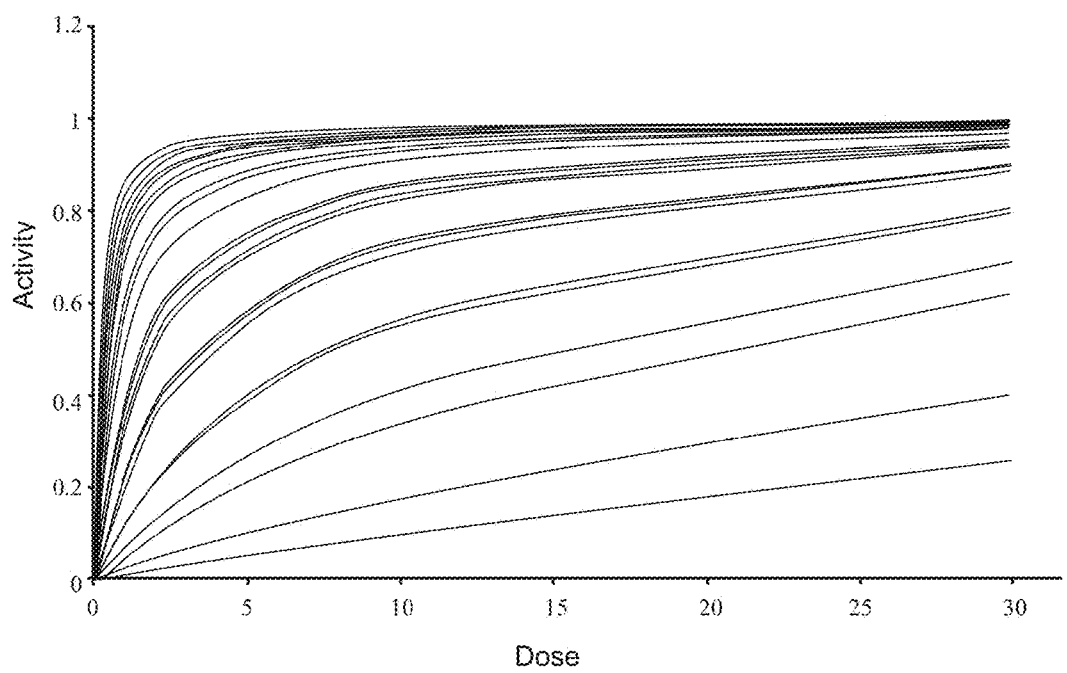

FIG. 7 shows the response for each individual formulation (for the hypothetical sample). The curves on the plot represent, in order from the bottom-most curve, samples 25, 15, 14, 10, 9, 18, 20, 7, 24, 22, 6, 5, 3, 23, 11, 2, 17, 12, 13, 19, 4, 1, 21, 16, and 8.

Figure 8:
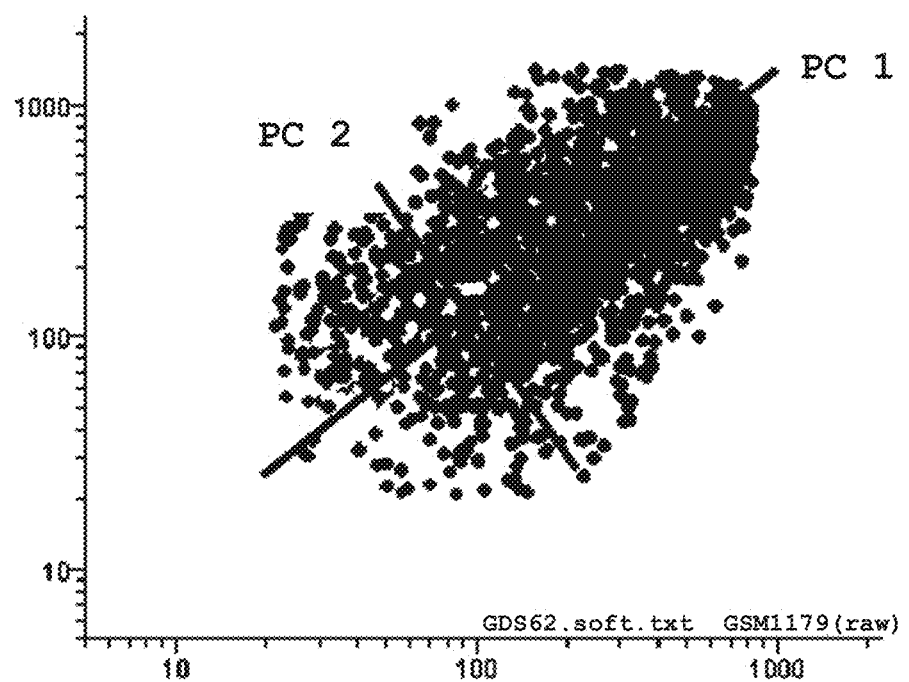

FIG. 8 shows a schematic illustration of the principal component analysis applied to a two-dimensional data set.

Figure 9:
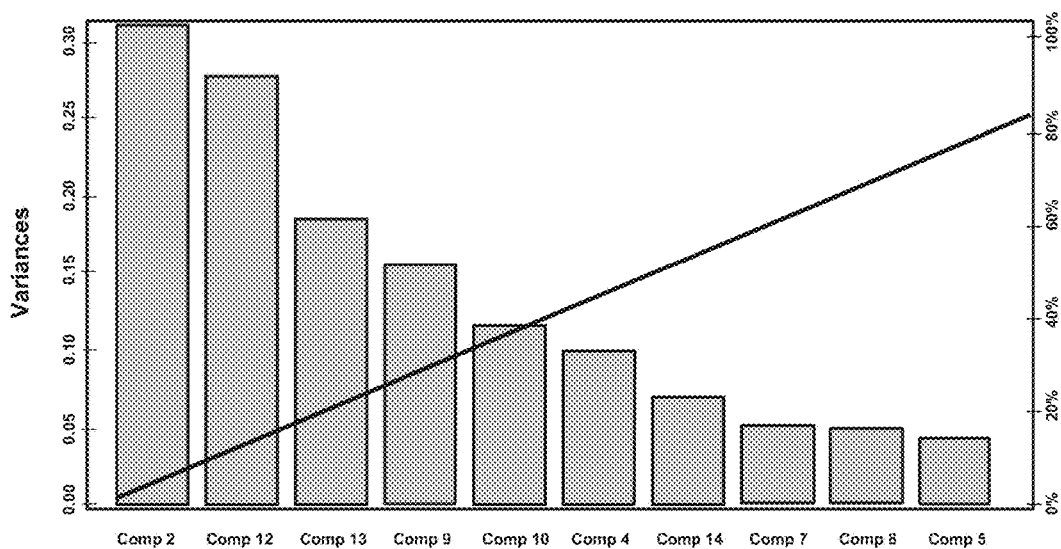

FIG. 9 shows the results of the application of the PCA to a set of synthetic data. Note that 10 variables out of 5 (transformed variables) cover 80% of the variation in data. This suggests very little correlation/dependence/interaction and the information are spread over all the variables.

Figure 10:
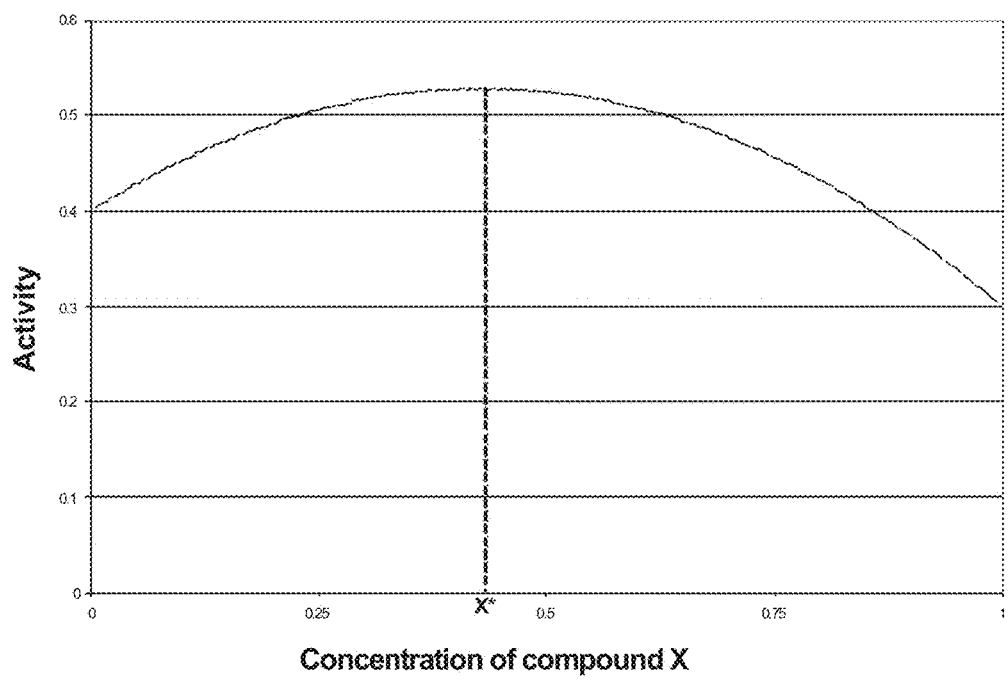

FIG. 10 shows an analytical elaboration of the location of the peak X*.

Figure 11A:
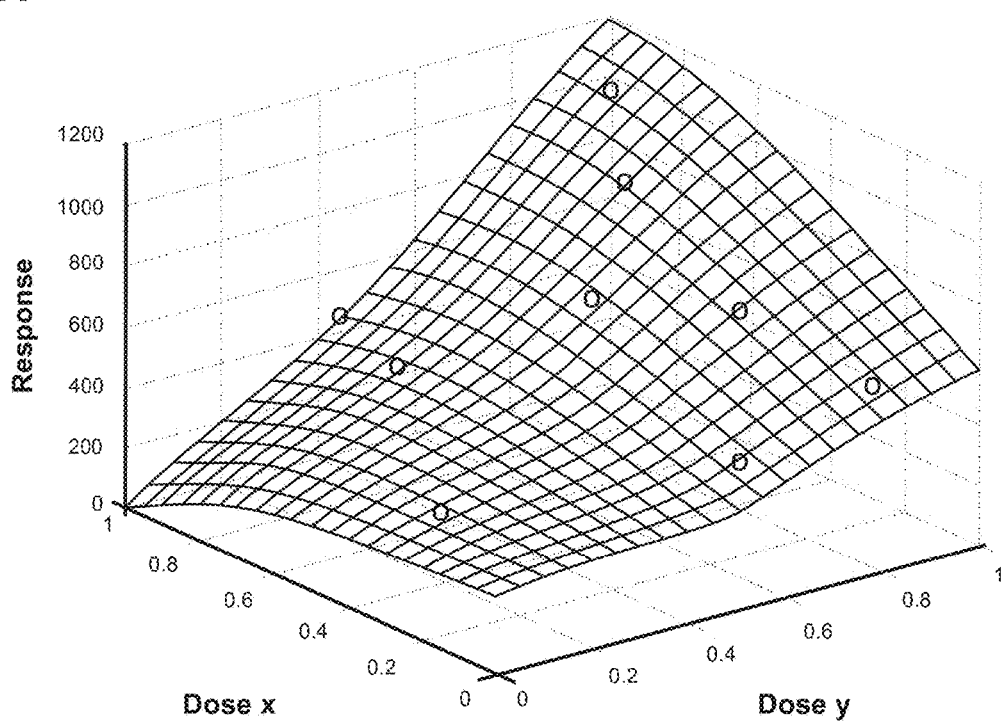
Figure 11B:
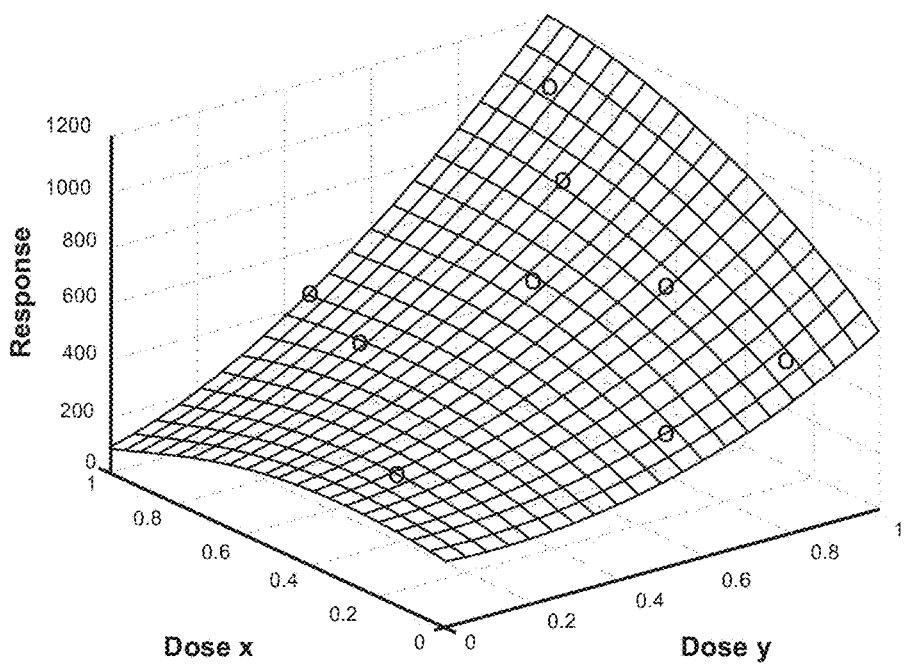
Figure 11C:
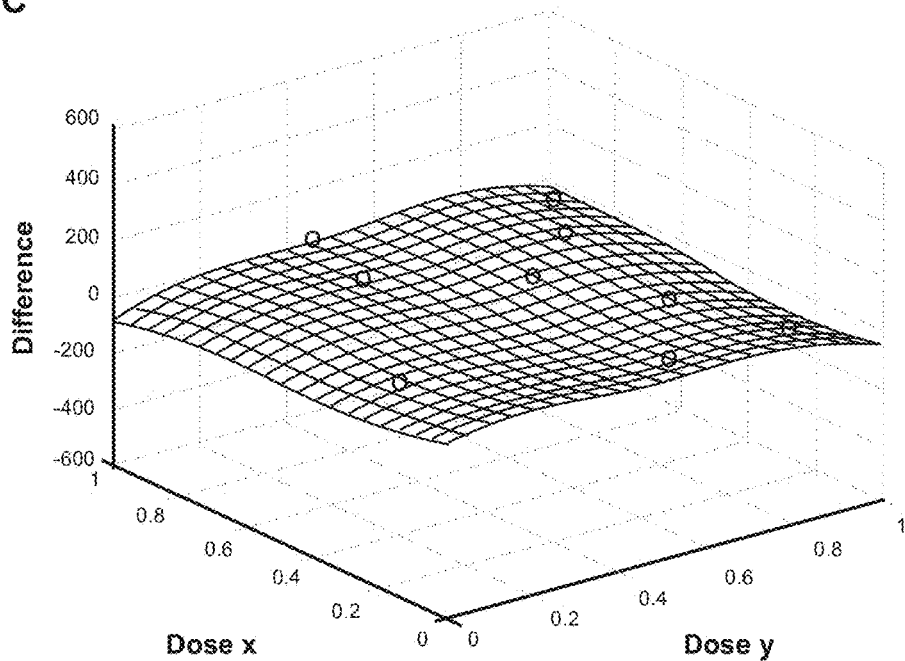
Figure 11D:
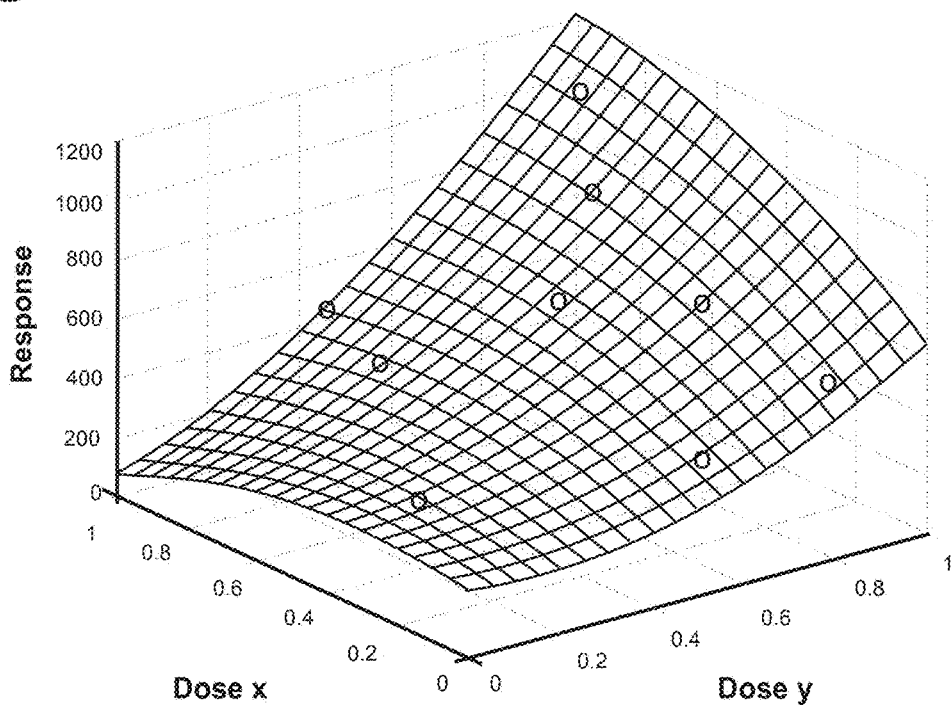
Figure 11E:
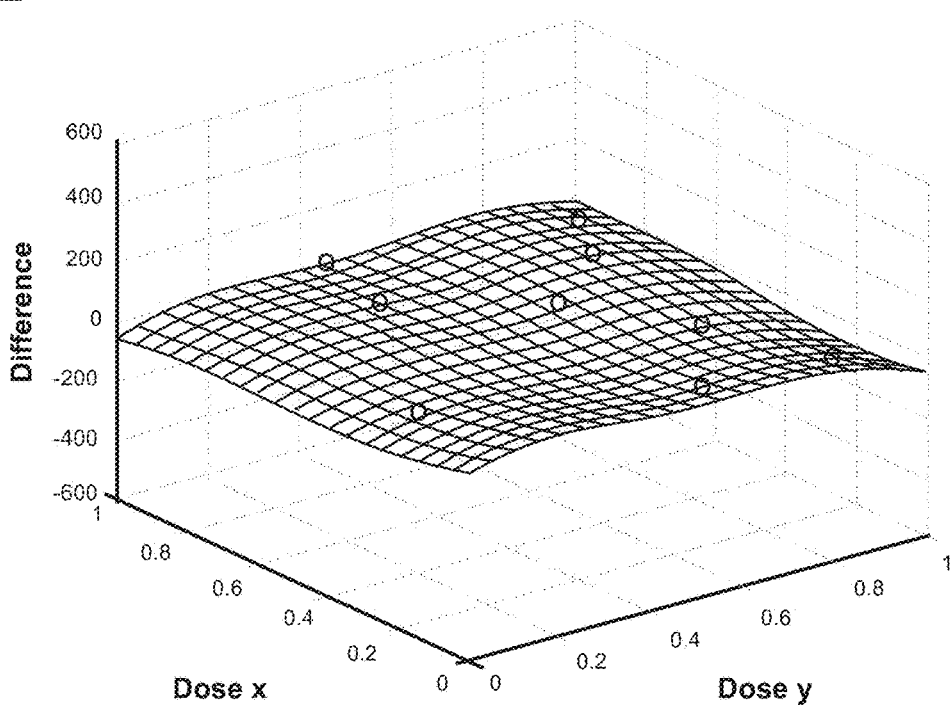
Figure 11F:
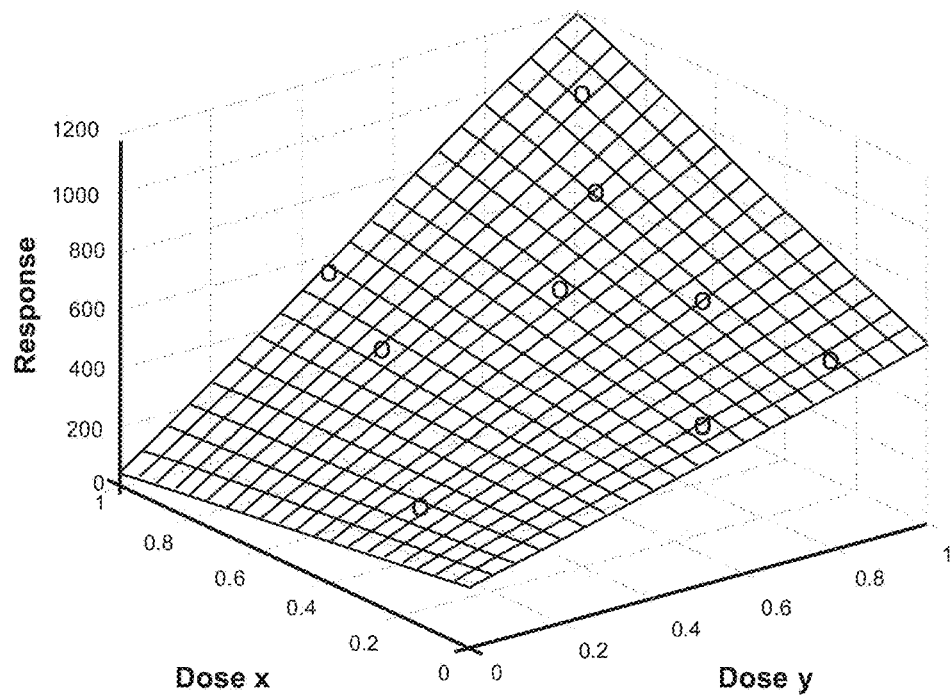
Figure 11G:
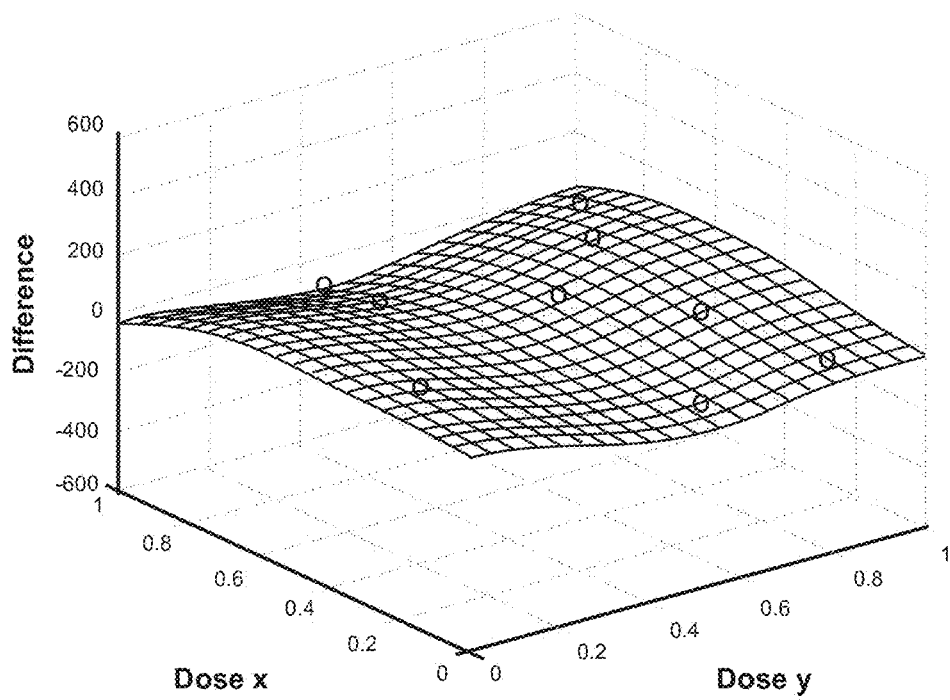

FIGS. 11A-G show an illustration of the various dose dependent functions in example. Original data, model responses, and differences between the original and the models. Locations used in the model fitting are marked with circles. FIG. 11A shows a plot of the original data, FIG. 11B shows a plot of the eight-term model, FIG. 11C shows a plot of the eight-term difference, FIG. 11D shows a plot of the six-term model, FIG. 11E shows a plot of the six-term difference, FIG. 11F shows a plot of the four-term model, and FIG. 11G shows a plot of the four-term difference.

Figure 12:
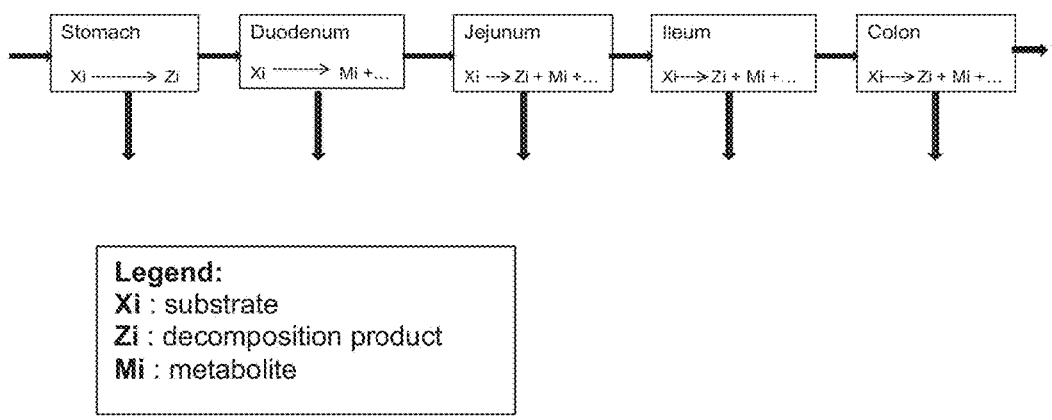

FIG. 12 shows a schematic showing the transit of a component and its decomposition products and/or metabolites along the gastrointestinal tract. Decomposition is chemical and metabolism could originate from enzymes of pancreas in the duodenum or intestinal flora in the colon. Xi, Zi, and Mi represent substrates, decomposition products, and metabolites, respectively.

Figure 13:
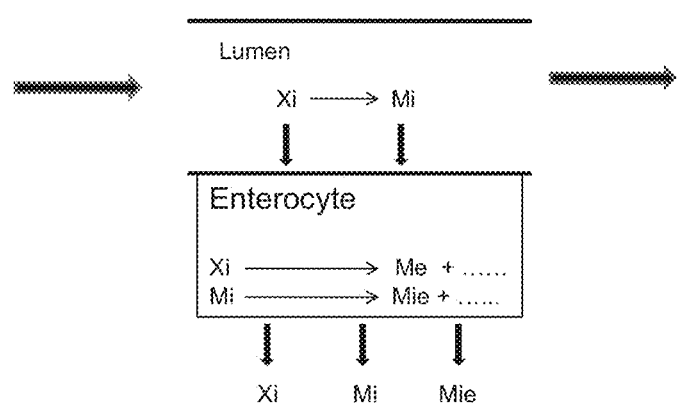

FIG. 13 shows a schematic showing the transport of a component and its metabolites across an enterocyte. Within the enterocyte, metabolism of the component and its metabolite could also occur. The rate at which these species traverse is measured by their permeability, which can be used to estimate absorption rate. Xi and Mi represent substrates and metabolites, respectively.

Figure 14:
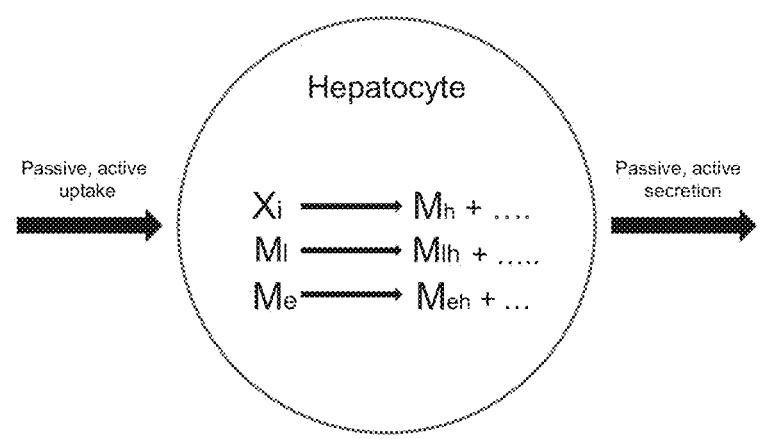

FIG. 14 shows events occur to a representative hepatocyte. The uptake of a component and/or its decomposition products and metabolites is potentially governed by passive and active processes. Within the hepatocyte, all of the species could potentially be bound or metabolized. The exit of these species is also governed by passive and/or active processes. Xi, Mi, and Me represent substrates, metabolite 1, e and h are metabolites formed in the intestinal lumen, the enterocytes and the liver, respectively. These metabolites are from intestinal lumen and enterocytes.

Figure 15:
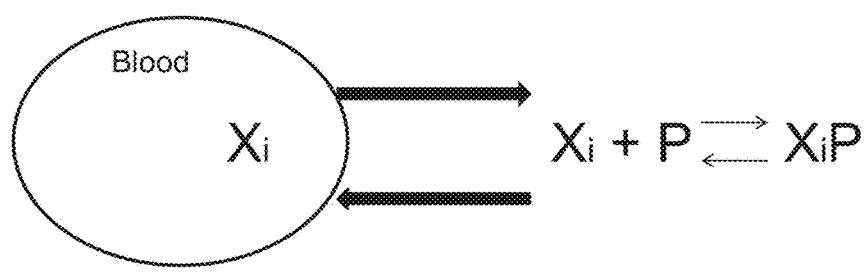

FIG. 15 is a schematic showing the distribution of a component in blood. In general, the free concentration in plasma, Xi, is the target for measurement.

Figure 16:
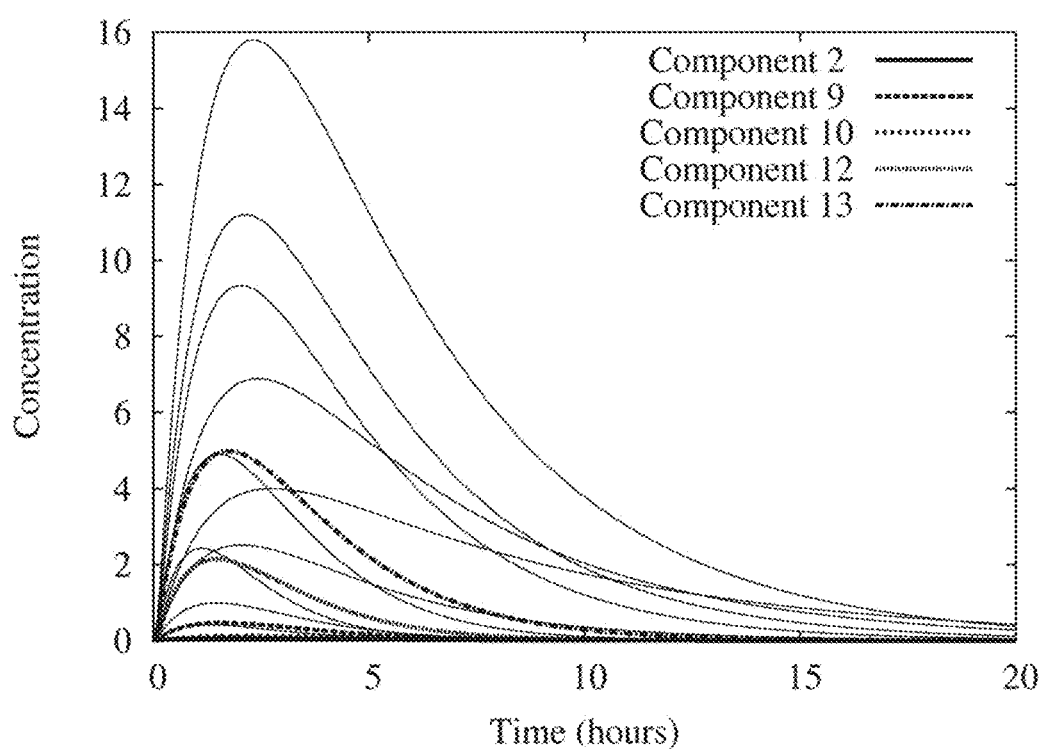

FIG. 16 shows concentration vs. time profiles of the components after 50 units of mixture 1 was administered orally. Components 2, 9, 10, 12 and 13 are shown in bold. Note: Concentration of compound 2 was too low to be shown.

Figure 17:
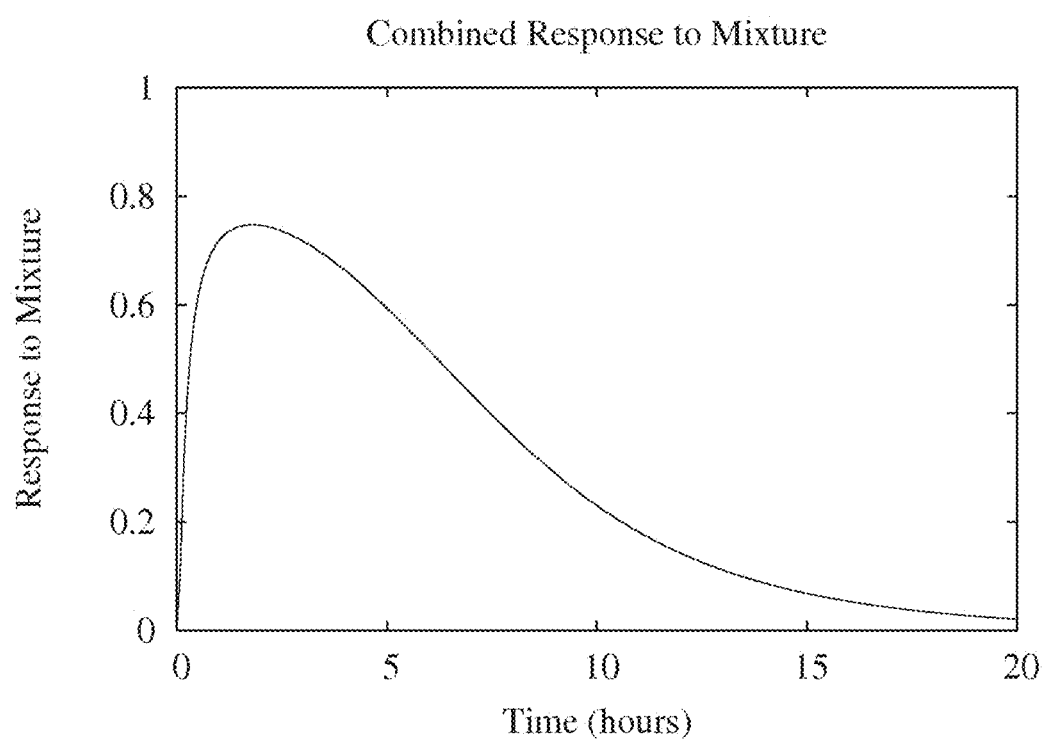

FIG. 17 shows combined effect vs. time profile after 50 units of mixture 1 was given orally. The response is mainly contributed by components 2, 9, 10, 12 and 13.

Figure 18:
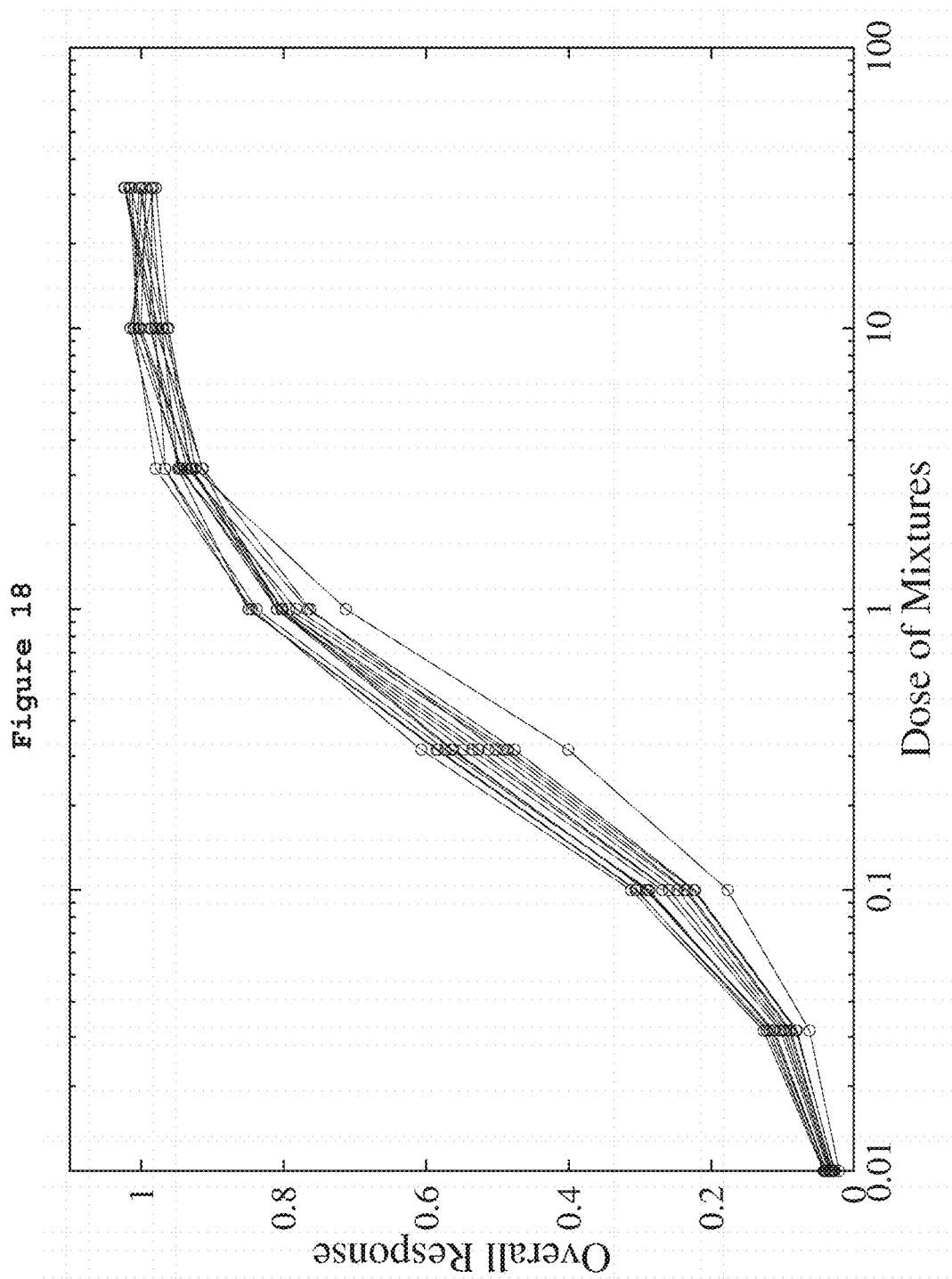

FIG. 18 shows a system of 50 components, each with a linear response and two pairs with additional interactions. With a Michaelis-Menton style limit to the total interactions and ±5% noise was noted that the above curves are typical of the overall response data for mixtures with components randomly distributed between 0 and 1 unit in each mixture.

Figure 19:
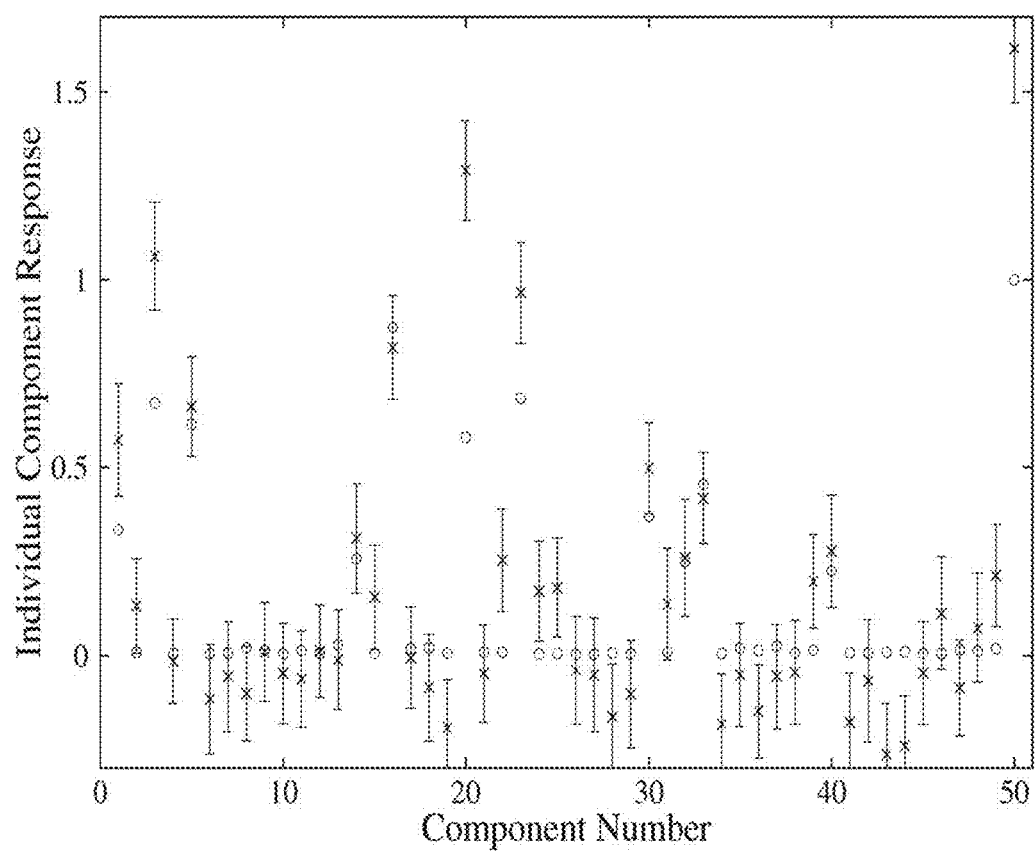

FIG. 19 shows 150 mixtures and overall responses from the 1.0 dose point assuming a linear response from each of the 50 components.

Figure 20:
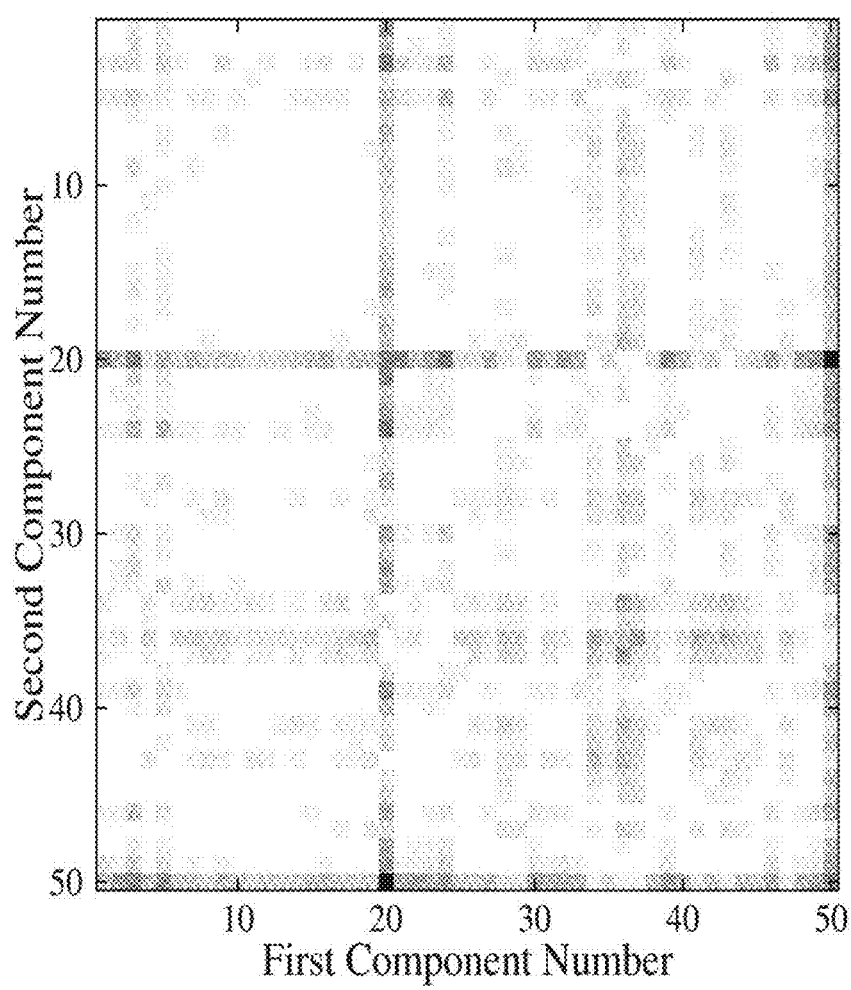

FIG. 20 shows a plot of the correlations between the residual and each of the multiplicative pair terms. Higher correlations are darker.

Figure 21:
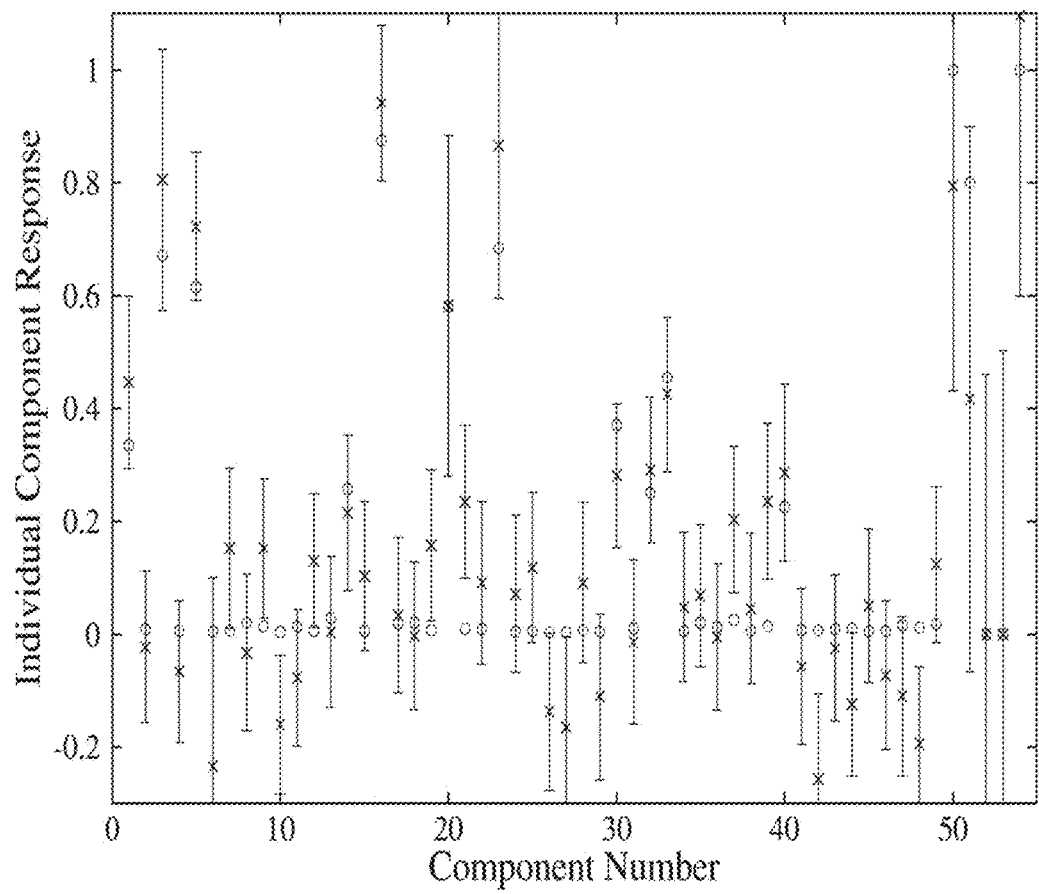

FIG. 21 shows a new and improved estimate yielded by adding four pair terms as pseudo-components 51 to 54.

Figure 22:
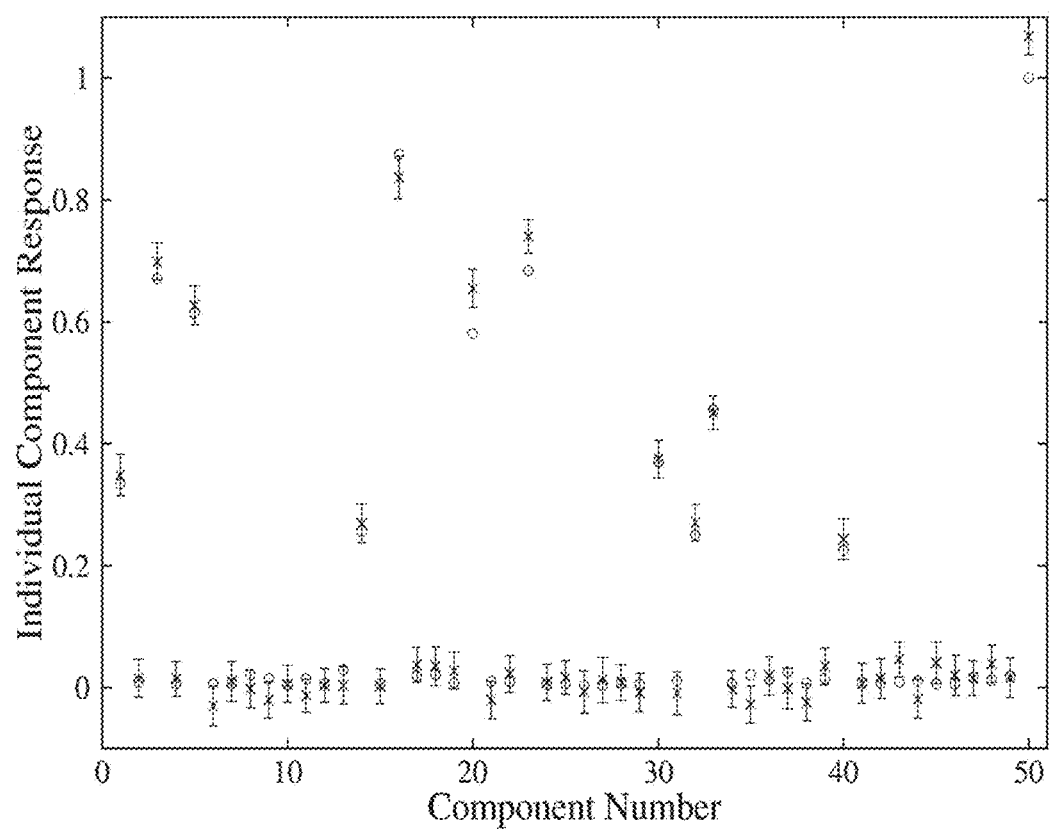

FIG. 22 shows an estimate obtained by repeating the same systems, but now using data from three dose points (1.0, 0.3, and 0.1) gives a tighter and more accurate fit in the first estimate.

Figure 23:
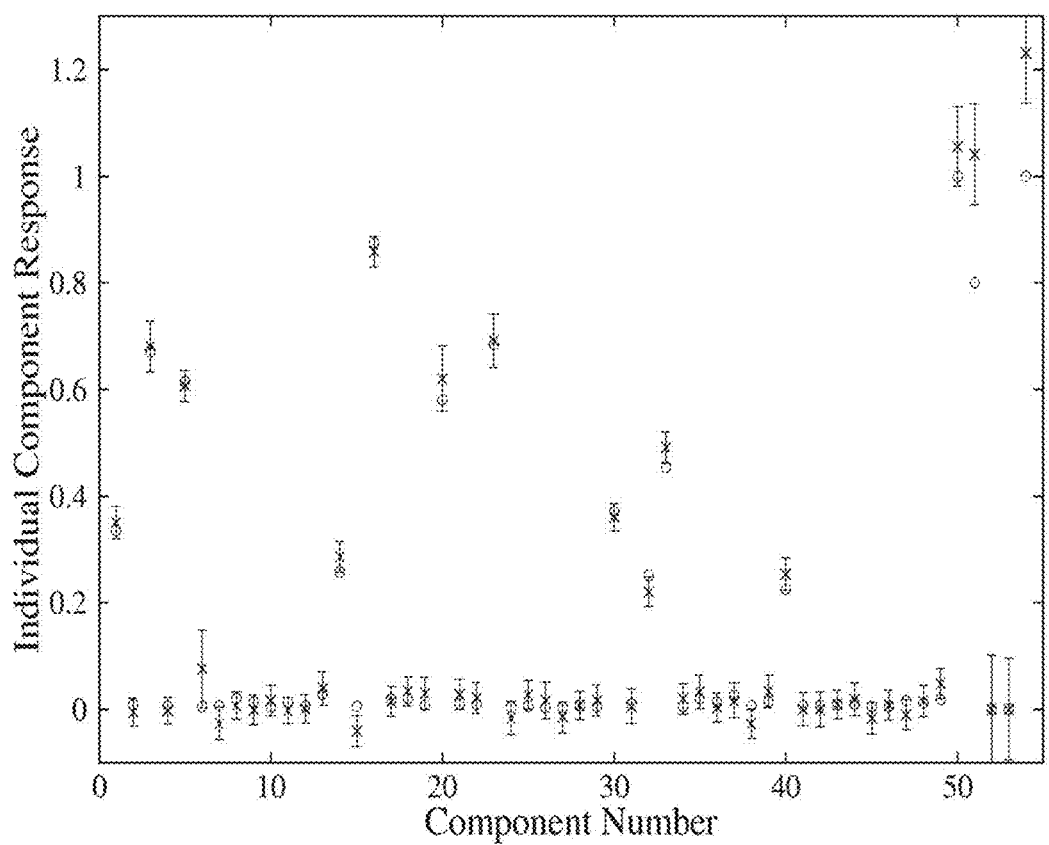

FIG. 23 uses the same four pseudo-components and gives a second estimate with a better fit than in the single dose point case.

Figure 24:
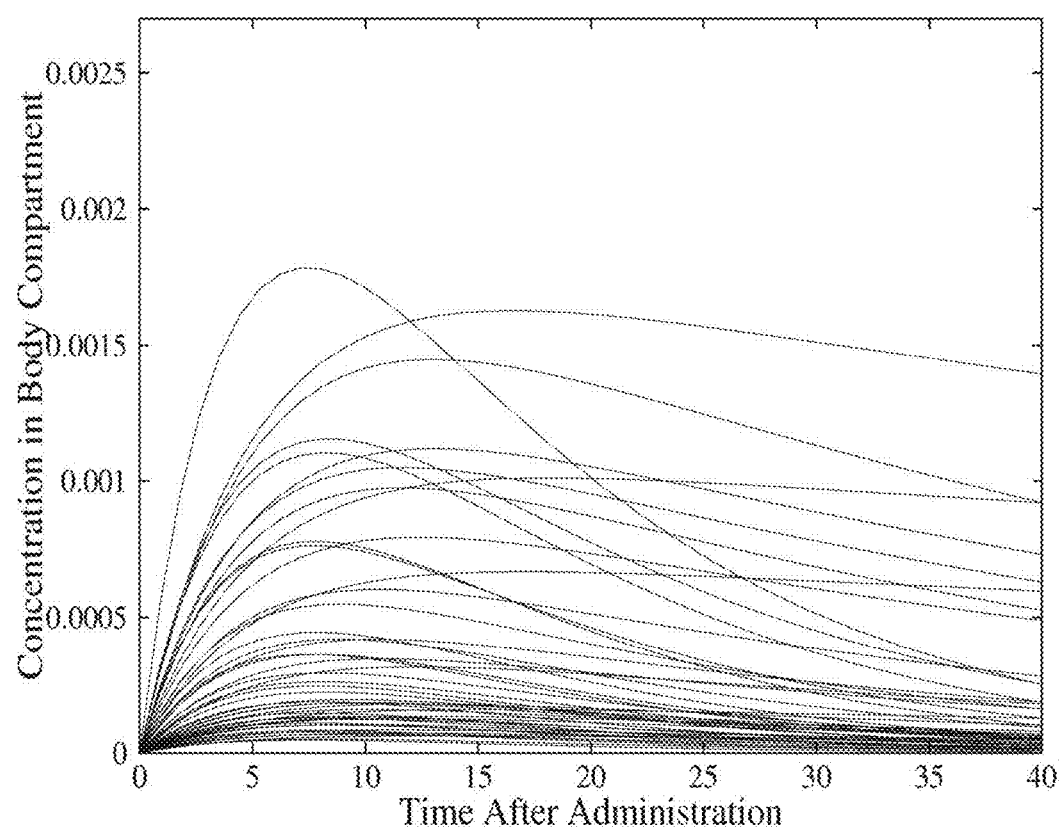

FIG. 24 shows time curves for doses of 4 and 0 units in the intestine and body compartments respectively at time 0 for the system described in Table 11.

Figure 25:
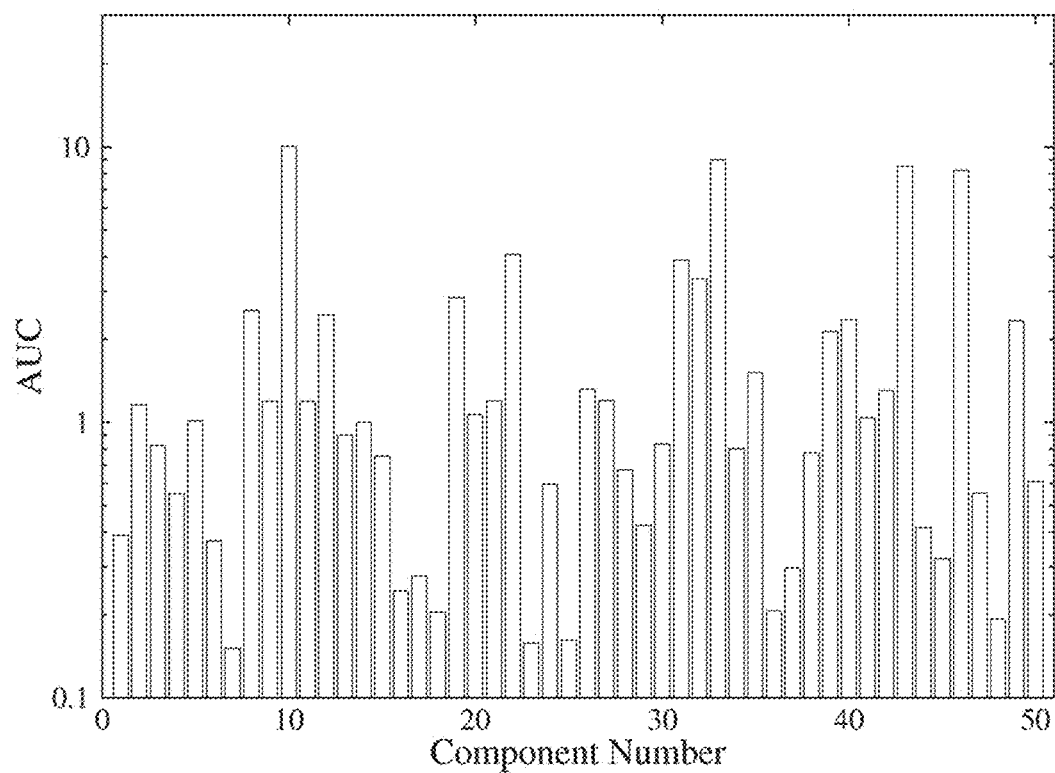

FIG. 25 shows the Area Under Curve (AUC) for the quantity in body-time curves. This data was given in Table 11. Note the broad range of effective absorption and elimination (nearly 2 orders of magnitude in variation).

Figure 26:
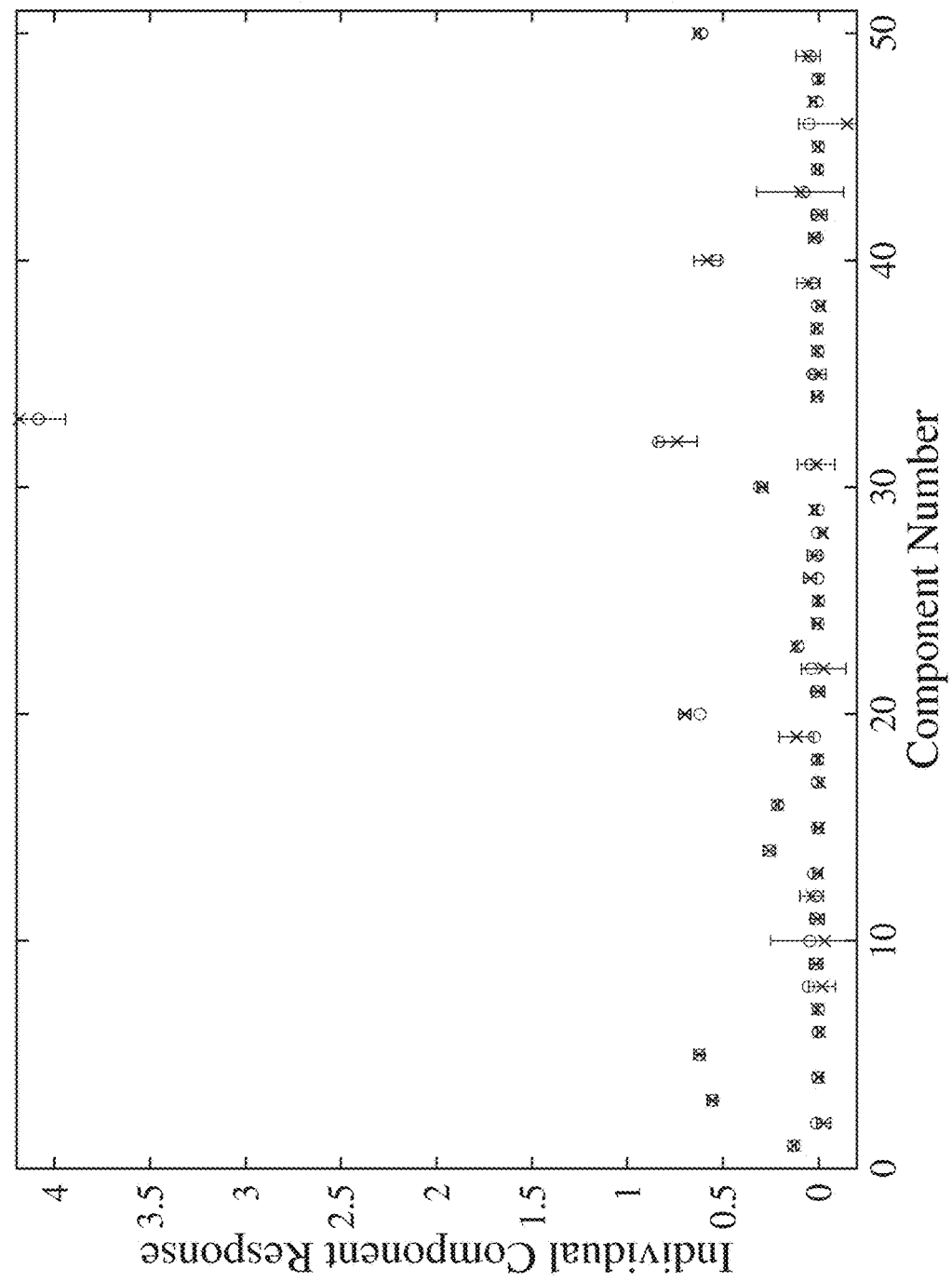

FIG. 26 shows the same set of 150 mixtures scaled by the AUC of each compound (taking the AUC values to be the exposure of the body to each compound).

Figure 27:
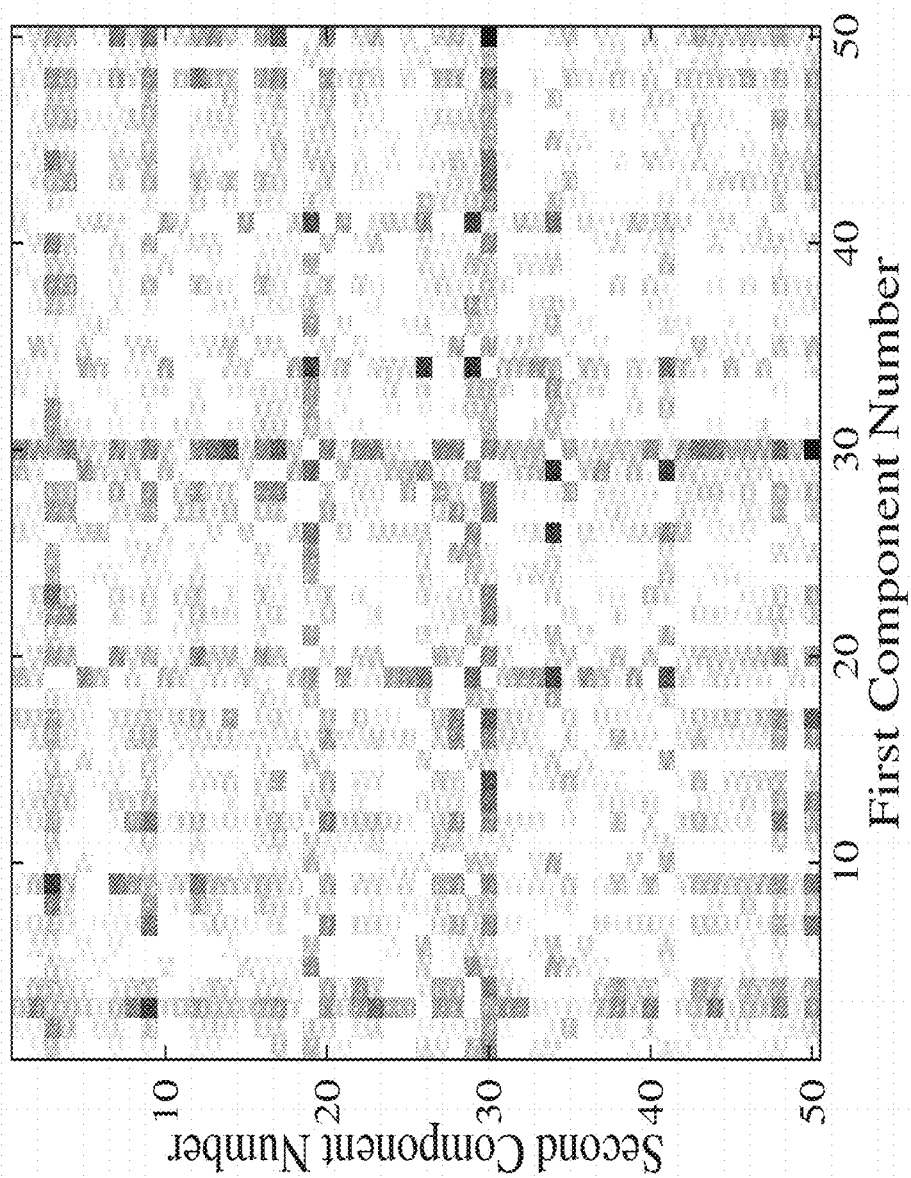

FIG. 27 shows the residuals, which vary dramatically from the previous plots. The darkness in each of these plots is scaled to the most correlated points in the plot, so the appearance of individual points can only be compared within each of these figures and not between them. The strongest correlations are actually weaker in this plot than in the previous one.

Figure 28:
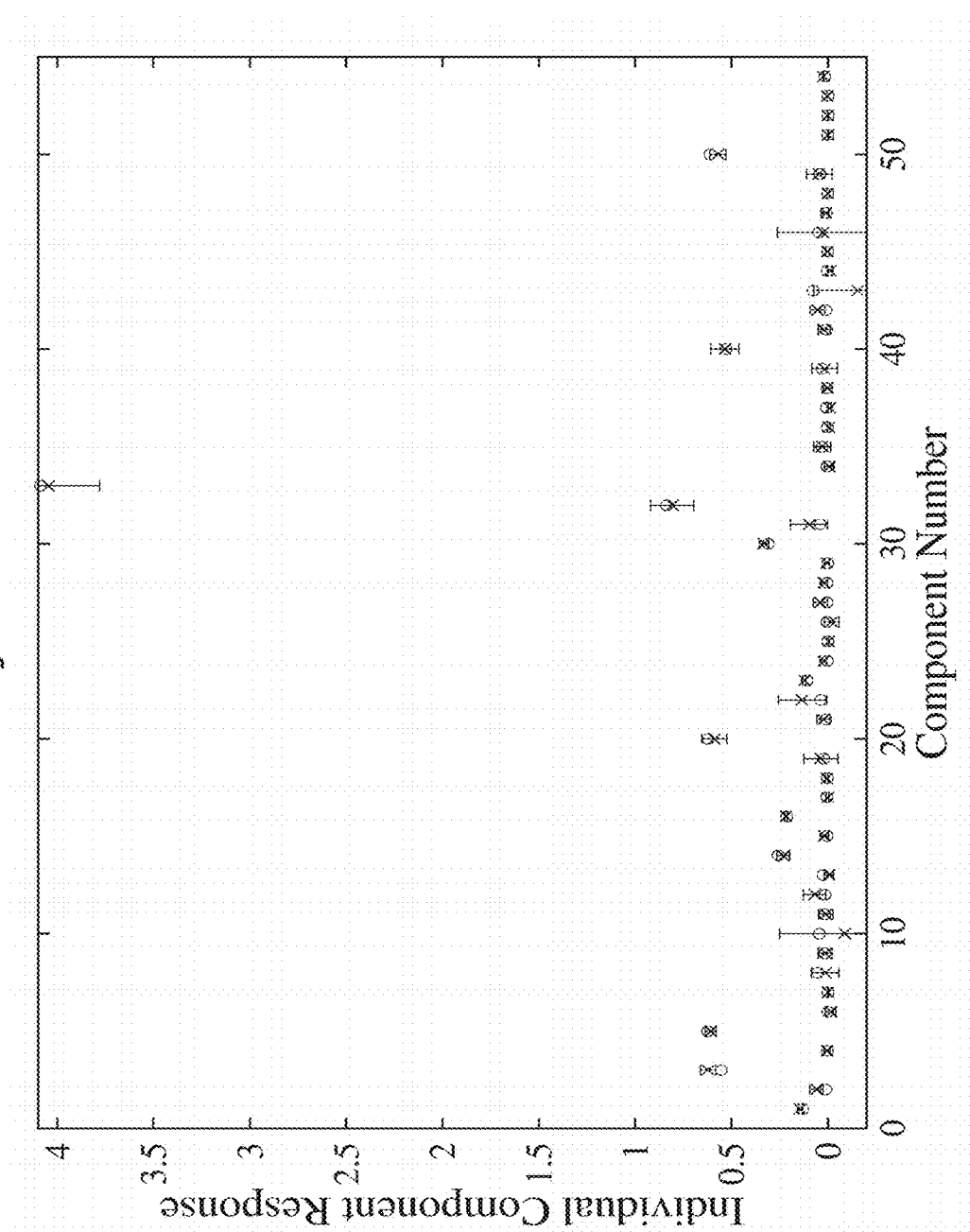

FIG. 28 shows a second estimate with four pseudo-components added. It is not much different from the first estimate, and the pseudo-components have very small responses as the components composing them are not significantly present.

Figure 29:
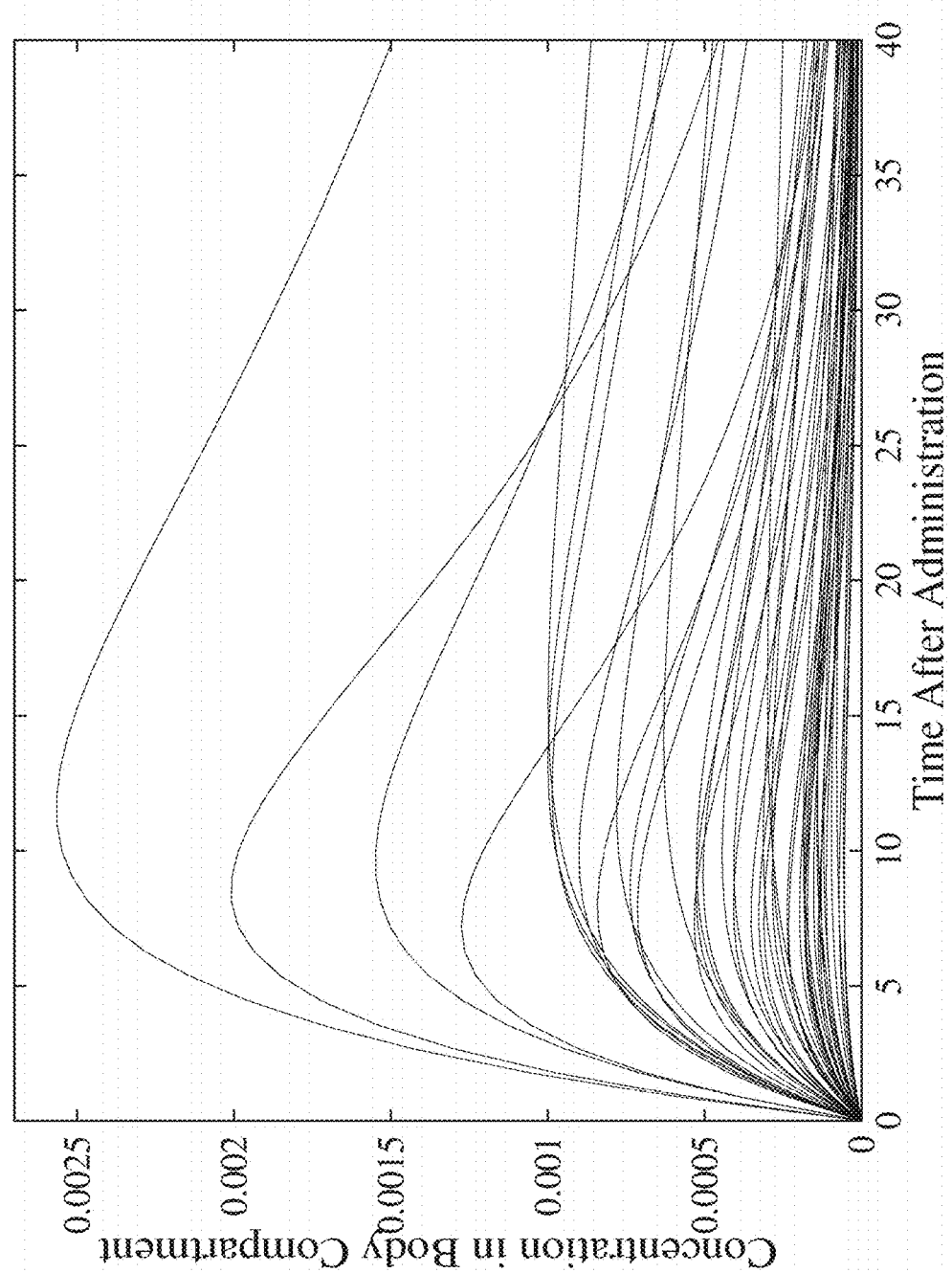

FIG. 29 shows the time curves given by the second set of pharmacokinetic parameters.

Figure 30:
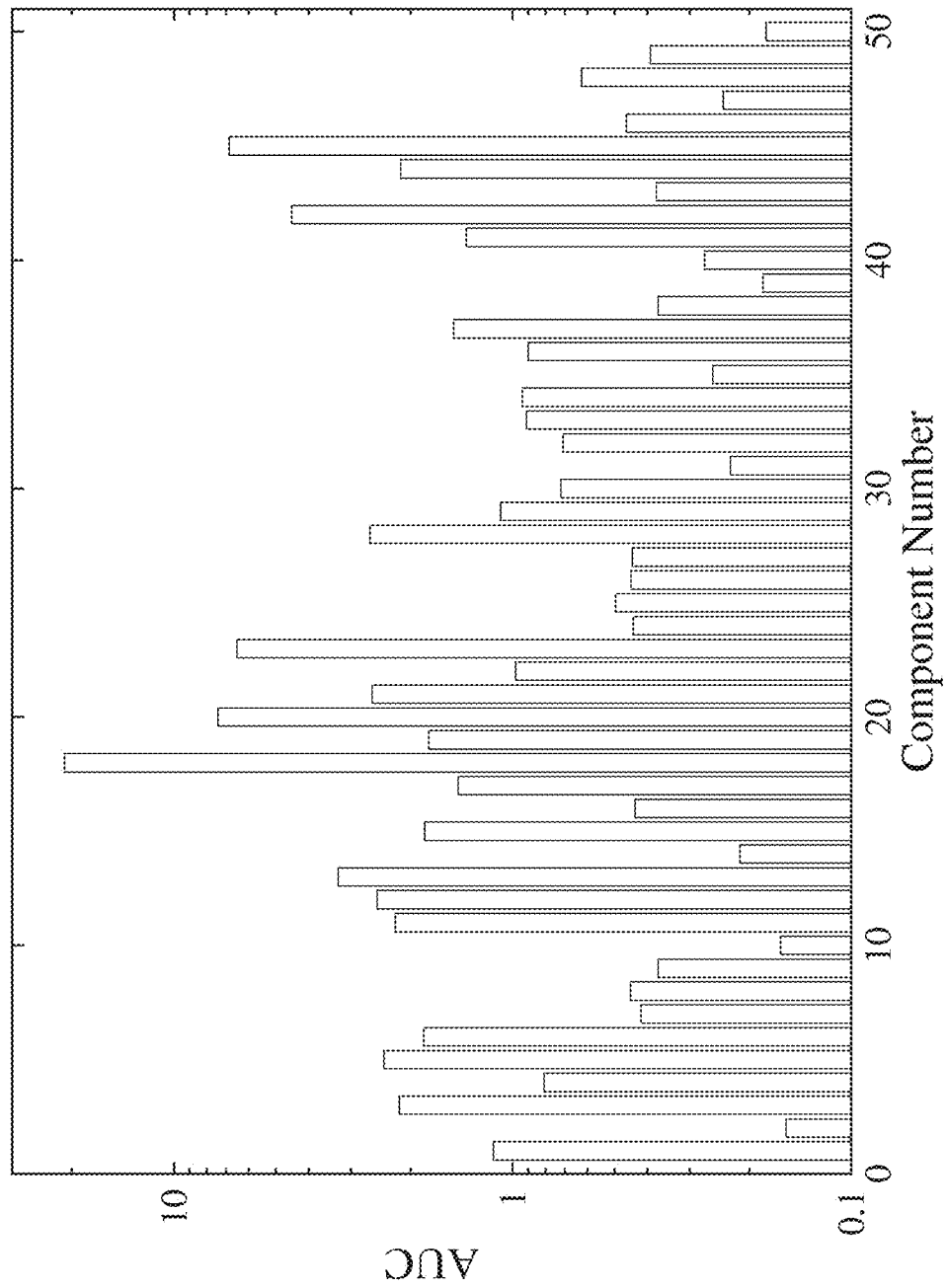

FIG. 30 shows the AUCs corresponding to the quantities in the previous plot.

Figure 31:
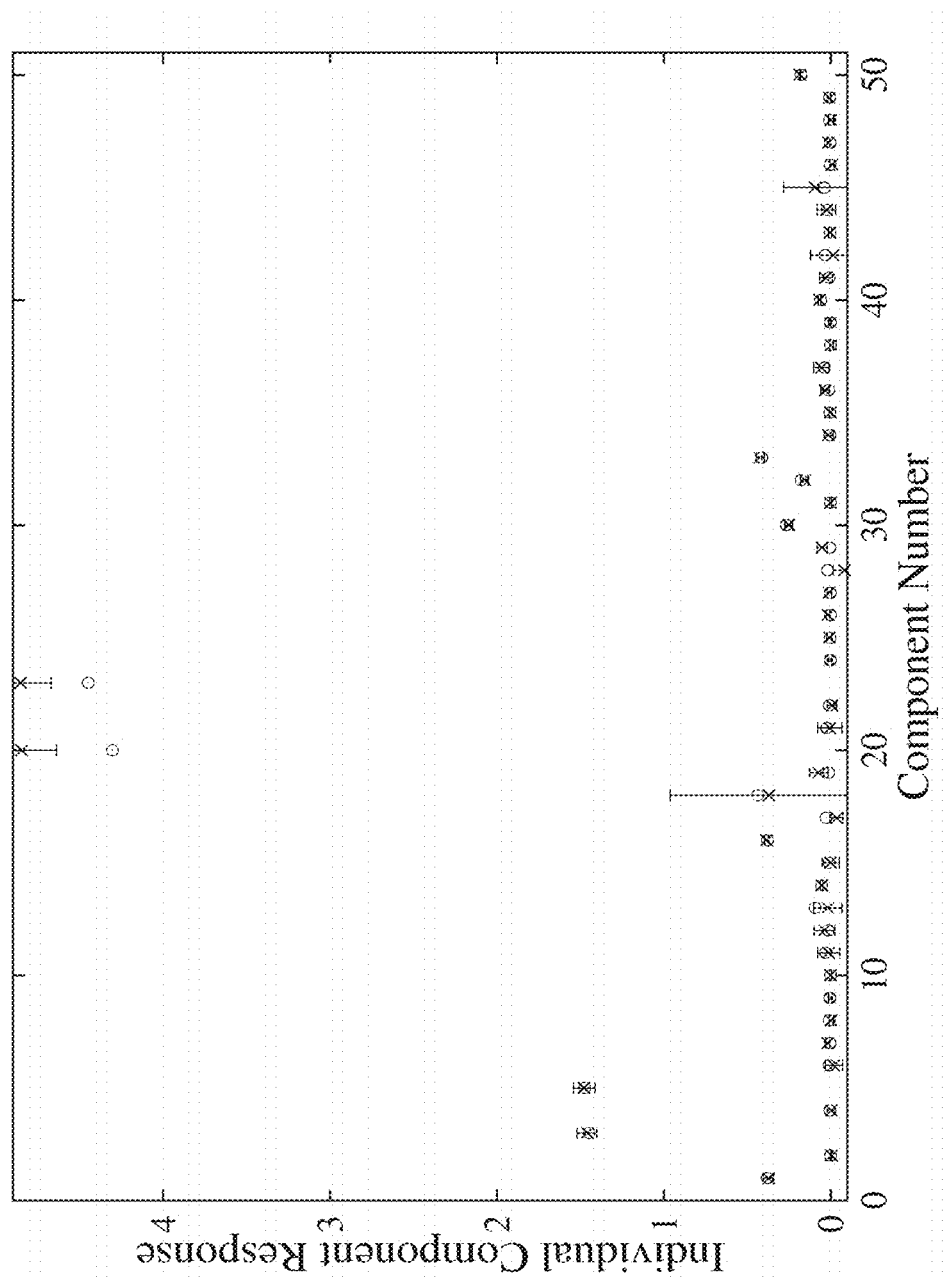

FIG. 31 shows how the first estimate now reveals two important components, and two moderate ones.

FIG. 32 shows how, again, adding four pseudo-components has little effect on the system as the synergistic terms are largely suppressed.

Figure 33:
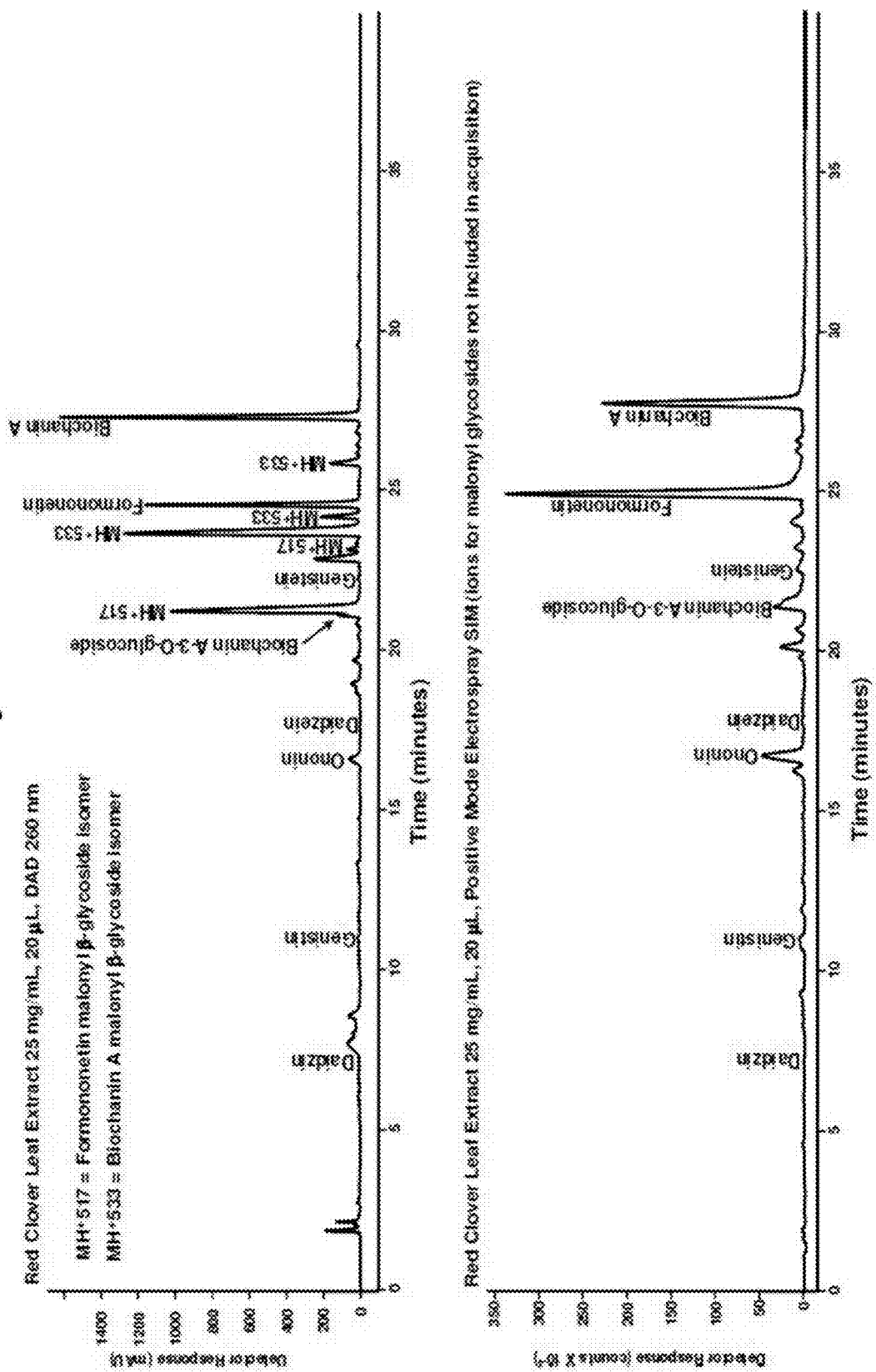

FIG. 33 are representative ultra violet (UV) and Mass spectrometric (MS) chromatograms obtained from an extract of Red clover (*Trifolium pratense*). It is clear that the precursors of genistein and daidzein are the major components in the extract.

DETAILED DESCRIPTION OF THE INVENTION

The present invention describes a process to: a. identify a group of active compounds from a mixture such as, but not limited to, that of an herbal extract; b. identify groups of ingredients, be they active or inactive, which interact with each other to produce an observable effect; c. estimate pharmacokinetic and pharmacodynamic characteristics of the active ingredients; d. estimate concentration time profiles of active ingredients at the site of action in vivo; e. estimate the overall response time profile; and f. calculate optimum dosage to provide desired response profile.

Pharmacokinetics of a Single Component

An understanding of the pharmacokinetics of a compound is important for the illustration of the concept behind this invention. Pharmacokinetics is a discipline which deals with absorption, distribution, metabolism and excretion of a compound in the body. Basically, it is a mathematical description of the time-course of a compound in the body. The name, pharmacokinetics, was first coined by Dietrich in 1952. This area became an important branch of pharmaceutical development after stellar research performed by Professors Gerhard Levy, Milo Gilbaldi, Leslie Benet, along with other prominent pharmacokineticists of our time. Apart from our understanding today, these researchers also had to convince pharmaceutical scientists at the time that a potent chemical is not effective and cannot be developed into a drug unless it can be absorbed and delivered to the site of action in adequate amounts. Not only must the ingredient be delivered to the site of action in adequate amounts, the component also has to be retained at the site of action for an adequate period of time before an adequate clinical response can be measured. This fundamental concept has led to the understanding that in order for a chemical to be developed into a drug, it has to have adequate potency and it also has to have adequate "drug-like" properties. Drug-like properties are quantified by pharmacokinetic properties. Potency is a measure of the inherent activity of a chemical, for example, the concentration which could inhibit an enzyme (such as cholinesterase) by 50%.

Traditionally, pharmacokinetic parameters such as clearance, half-life and volume of distribution, are measured in vivo. In the last two decades, many in vitro and in silico methods have been reported in the literature. These methodologies are being refined constantly and their predictive power improves over the years (Grass et al., 2003; Brightman et al., 2006a). Nowadays, there are commercial programs available for estimating pharmacokinetic and pharmacodynamic characteristics of a lead.

Since one object of this invention is to develop natural products, most of which are given orally, the pharmacokinetics of a compound after oral administration is described in detail in this invention. It should be noted that this concept can easily be extended for components which are administered parenterally or non-parenterally.

Figure 1:
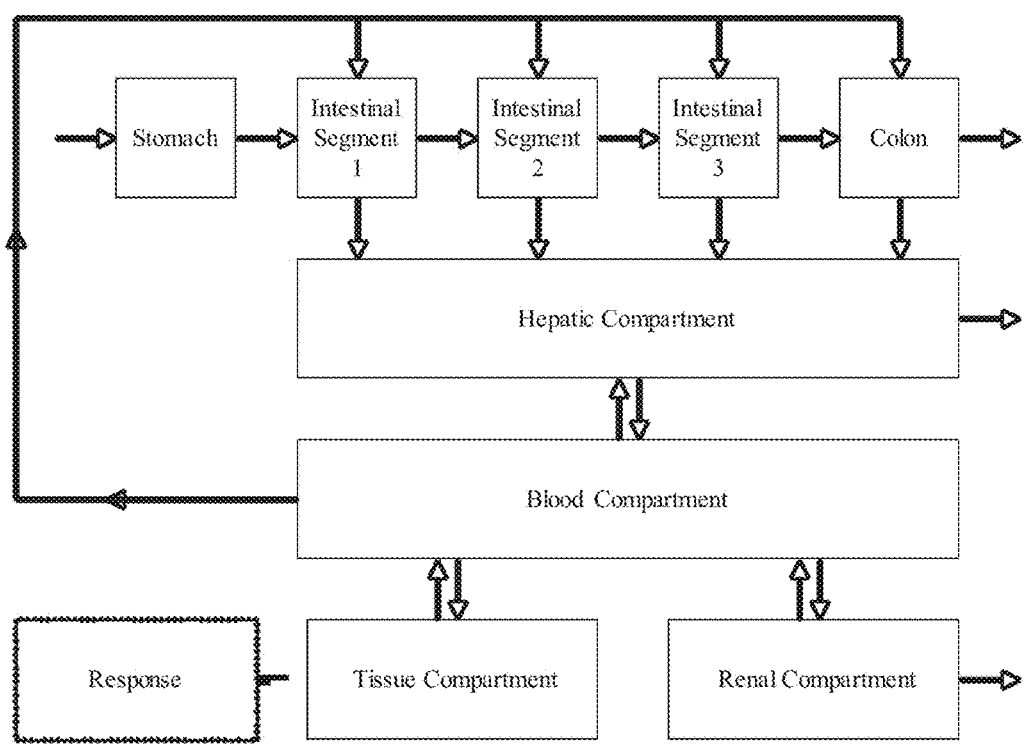

Absorption:

After a compound is ingested orally, a number of events could occur before it is absorbed into the systemic circulation (FIG. 1). If the compound was not ingested as a solution, it would have to be dissolved before it can enter the enterocytes. Before the compound is absorbed, it has to survive the harsh environment in gastrointestinal lumen. The high acidity in the stomach and enzymes produced in the pancreas and intestinal cells and intestinal bacteria have the ability to break down or metabolize the compound. Examples are z-ligustilide of Chuanxiong, ginsenosides of *Panax ginseng* and polysaccharides of *Ganoderma lucidum*. At times, the breakdown or metabolic products are active; therefore, the overall response in the body could include that of the breakdown or metabolic products. There are instances where the component, which has in vitro activity, is not the actual active species in the body because it is not absorbed and is incapable of reaching the site of action. Instead, the breakdown products or metabolites are active and it is these species that are responsible for the in vivo activity of the "active" component. A good example is the ginsenosides of *Panax ginseng*. The oligosaccharides connected to the aglycone are cleaved by colonic bacteria in a stepwise fashion to form the major metabolites, 20S-protopanaxadiol 20-O-beta-D-glucopyranoside and 20S-protopanaxatriol (Hasegawa, 2004). The aglycones are the active moieties of ginseng and the ginsenosides act like prodrugs.

The rate and extent of permeation of a component into enterocytes is dependent on its physicochemical properties, such as solubility, pKa, lipophilicity, partition coefficient, etc. Inside the enterocytes, the component is exposed to metabolic enzymes which could potentially convert it to metabolites. Again, these metabolites may be active. Z-ligustilide, glycerrhetic acid, etc. are good examples of intestinal metabolism.

After the component is absorbed, it is transported by blood in the mesenteric circulation which drains into the liver through the portal vein. This component is then faced with an abundance of liver metabolic enzymes which could metabolize it into more polar metabolites.

The loss of a component through chemical or metabolic degradation during the absorption process is called first-pass effect. The bioavailability, F, of the component is determined by:

$$F = 1 - F_g F_l \quad (1)$$

where $F_g$ is the fraction that survives the intestine, and $F_l$ is the fraction that passes through the liver intact. $F_g$ is estimated using the following equation:

$$F_g = 1 - F_d - F_{ml} - F_{na} - F_{m,int} \quad (2)$$

where $F_d$ is fraction of dose decomposed in the gastric and intestinal lumen; $F_{ml}$ is the fraction that is metabolized by the enzymes in the intestinal lumen; $F_{na}$ is the fraction which is not absorbed and $F_{m,int}$ is the fraction which is metabolized by enterocytes.

Distribution:

The component, which survives first-pass, is carried by blood to the heart through the superior vena cava. After being pumped through the pulmonary circulation, the component is transported to the rest of the body through the blood circulation. During this process, the component is distributed to various organs and tissues such as lungs, heart, brain, kidneys, adipose tissues, red blood cells and muscles. The component could also bind to cell membranes, plasma and cellular proteins. The extent to which a component distributes in the body is dependent on its physicochemical properties. A pharmacokinetic parameter describing the extent of the distribution of a component is called volume of distribution ($V_d$).

Elimination:

While the component is being circulated and distributed in the body, it could be degraded chemically or metabolized by enzymes in the blood, liver, kidneys and the lungs. The component and its degradation products may be secreted into the bile and/or excreted through the kidneys. The component or its degradation products that are eliminated through the bile may be absorbed from the intestine again. The later process is termed enterohepatic cycling.

The time course of a component in plasma or blood can be described using a pharmacokinetic model. Pharmacokinetic parameters that are used to describe a component are: absorption, F, volume of distribution, $V_d$, and total body clearance, $Cl_T$. $Cl_T$ is a term which includes all the elimination processes in the body. This term is described by equation 3:

$$Cl_T = Cl_h + Cl_r + Cl_{other} \quad (3)$$

where $Cl_h$ is hepatic clearance, $Cl_r$ is renal clearance, and $Cl_{other}$ is elimination by other organs.

Pharmacodynamics of a Single Component

While the component is being distributed to various parts of the body, it could also react with various cellular components, including receptors, to trigger a series of biochemical responses. These responses may be translated into a measurable clinical response. For example, ginkgolide B has been shown to be a platelet-activating factor receptor antagonist and it has a potential of being used to treat asthma when used in combination with carotenoid astaxanthin (Mahmoud et al., 2004).

Figure 2A:
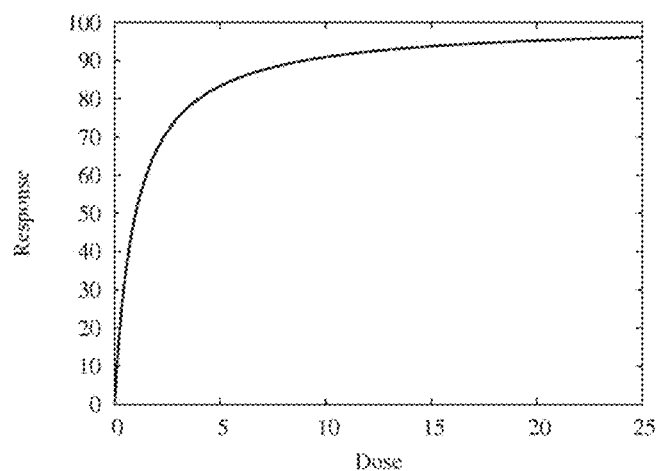
Figure 2B:
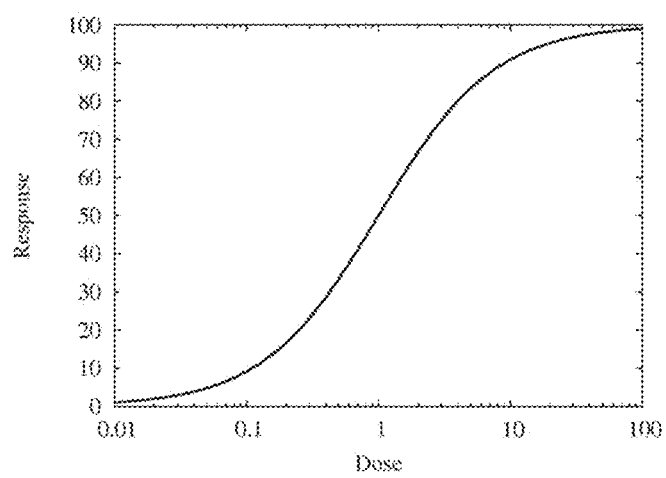

For a typical response, there is a dose- or concentration-response relationship. This type of relationship is often described using Michaelis-Menton kinetics (FIG. 2). Although there are other types of concentration-response relationships, the important issue in this invention is to be able to mathematically describe this type of relationship.

Pharmacokinetics of Multiple Components

When a mixture of components, such as that of a natural substance, is administered orally, they will undergo pharmacokinetic processes such as absorption, distribution and elimination that are similar to that of a single component. The complication with a mixture is that the administered components may interact with each other at various levels. For example, a component may enhance the absorption of other components. Rutin has been shown to increase the bioavailability of a natural substance. A component may be stabilized by the presence of other components. For example, z-ligustilde is stable in an alcoholic Chuanxiong extract; whereas the pure compound itself is unstable. Interaction at the enzyme level is well documented in the literature. For example, hyperforin in St. John's wort has been shown to induce P450 isozymes, particularly, CYP 3A4. This induction has led to a number of serious herb-drug interactions (Venkataramanan et al., 2006). A component may play a role in changing transporter functions, leading to a change in permeability of other components which are substrates for these transporters. Hence, the rate of absorption and elimination of a component may be changed significantly.

Components could compete for plasma protein binding sites. This competition could lead to a change in $V_d$, leading to a change in distribution and elimination of the affected components. Components may also compete for renal excretion where an active process is involved.

Besides pharmacokinetic interactions, the components and their breakdown products have the potential to interact at the receptor level; thereby changing the potency of another component.

Challenges of Developing a Multiple Component Product

It is very clear that the development of a multiple component product is extremely complicated, particularly when the conventional approach is used. Imagine trying to isolate all active substances from a mixture and study them individually before the actives are studied again in combination. It is no wonder this is not a preferred route for developing new pharmaceuticals or nutraceuticals (Williamson, 2001). The obvious question is: Is there a simpler way? To be more precise: Can the pharmacokinetics and pharmacodynamics of individual components and their mutual interactions be evaluated and quantified without disturbing the mixture?

Figure 3:
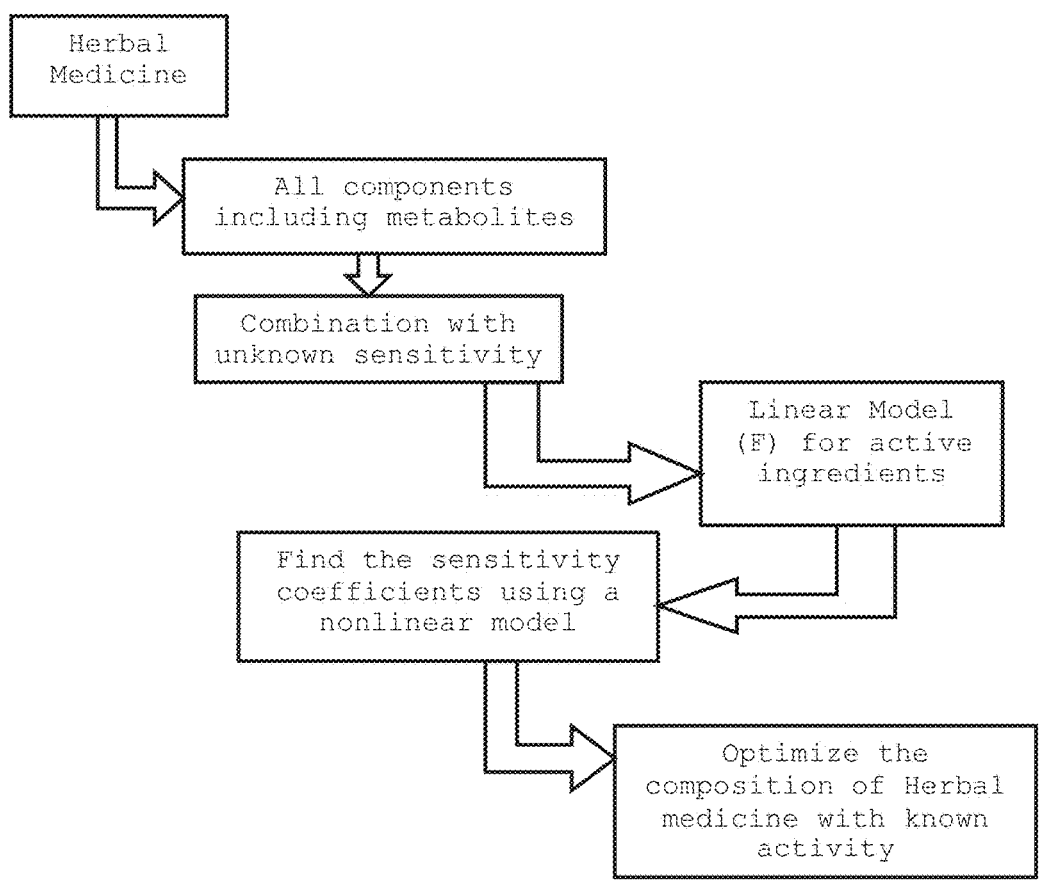
FIG. 3 shows a general flow chart of the optimization procedure; illustration of procedure.

In this invention, a detailed approach in obtaining pharmacokinetic and pharmacodynamic parameters of individual components in a mixture is described. FIG. 3 is a flow chart of the optimization procedure; which illustrates the steps taken in the procedure. These examples highlight the theoretical aspects of this invention. Through simulations, it is demonstrated that active components in a mixture can be accurately identified without purification of individual components, a process which has created a barrier for natural product research. Furthermore, the method described herein is employed to develop an herb, Red clover (*Trifolium pratense*), which is rich in phytoestrogens, for the treatment of postmenopausal osteoporosis.

In one embodiment, the present invention provides a method of predicting in vivo pharmacokinetics and pharmacodynamics properties of a composition with multiple components, comprising the steps of: (a) determining parameters describing the rate of elimination of the components in a plurality of mammalian tissue systems; (b) determining parameters describing distribution of the components in a plurality of mammalian tissue systems; and (c) inputting the parameters into mathematical models that will generate outputs to predict the pharmacokinetics and pharmacodynamics properties of the composition in vivo. In general, the parameters for the above methods are obtained from in vitro or in vivo studies. In one embodiment, the rate of elimination comprises one or more of the following: rate of metabolism, rate of adsorption, and rate of degradation. Representative examples of mammalian tissue systems include, but are not limited to, gastrointestinal tract, liver, kidney, blood, mammary gland, uterus, prostate, brain, and bone.

In one embodiment, the pharmacokinetics or pharmacodynamics properties of individual component are determined by in silico simulation. In another embodiment, the pharmacokinetics and pharmacodynamics properties comprise determining the potency of an individual component, and synergism or inhibition among the components. For example, the potency of an individual component can be determined by receptor binding assay, enzymatic assay, biochemical response assay, or assays with isolated tissues or organs.

In another embodiment, the present method further comprises the steps of determining parameters for active metabolites of the components according to steps (a) to (c) above, wherein outputs of the mathematical models will predict the pharmacokinetics and pharmacodynamics properties of the composition and the active metabolites in vivo. In general, pharmacokinetics and pharmacodynamics properties comprise concentration-time profiles and response-time profiles for the components and their metabolites.

In one embodiment, the rate of elimination comprises rate of metabolism and degradation. For rate of metabolism v, Michaelis-Menten kinetics or other forms of saturable kinetics can be used. For example, Michaelis-Menten kinetics is stated as follows:

$$v = \frac{V_{max} \cdot C}{EC_{50} + C},$$

where $V_{max}$ is the maximum metabolic rate, C is the concentration of substrate and $EC_{50}$ is the concentration at which 50% of the maximum rate occurs.

In one embodiment, rate of degradation (dc/dt) is generally assumed to be first order. What this means is that the rate of decomposition is concentration dependent:

$$\frac{dc}{dt} = C_0 e^{-Kt}$$

where c is concentration at time t, $C_0$ is the concentration at time zero and K is the first order degradation rate constant. This rate equation can be integrated and transformed to:

$$C = C_0 e^{-Kt}$$

The half-life of a substance is determined as time for 50% of the original concentration to disappear. From the above equation, half-life, $t^{1/2}$, is defined as:

$$t_{1/2} = \frac{0.693}{K}$$

In one embodiment, the arrows shown in FIG. 1 are first order processes that provide description for the decomposition.

In one embodiment, the method of the present invention comprises mathematical models that are capable of solving multiple unknowns which are linearly independent or interacting with each other. For example, the models include a model of weighted linear functions and the same model with added higher-order polynomial terms in single component doses and terms in the products of pairs of doses. In another embodiment, the mathematical models of the present invention comprise equations (7), (13) and/or (14) as described herein. In another embodiment, examples of applicable mathematical models include, but are not limited to, least absolute shrinkage and selection operator (LASSO), wavelet-based deconvolution, compressed sensing, and gradient projection algorithm.

In one embodiment, determining the rate of elimination in gastrointestinal tract comprises in vitro assays. For example, such assays comprise artificial gastric or intestinal juice, intestinal flora, intestinal microsomes, or permeability studies using cultured cells or intestinal tissues (e.g. Caco-2 cells or MDCK cells), whereas the rate of absorption can be determined by rate of permeability measured using cultured cells or intestinal tissues.

In one embodiment, determining the rate of elimination in liver comprises assays using freshly harvested hepatocytes, cryopreserved hepatocytes, hepatic microsomes, hepatic cytosol or S-9 fractions.

In one embodiment, determination of renal elimination is based on the components' chemical structure or in silico simulation.

In one embodiment, the determination of distribution in blood or plasma comprises determining binding to plasma protein, binding to blood protein, pKa, log P, log D, and volume of distribution of a component.

The present invention also provides a composition comprising multiple components as identified by the method disclosed herein, wherein the components have desirable in vivo pharmacokinetics and pharmacodynamics properties as determined by the method disclosed herein. For example, the composition may comprise Red clover (*Trifolium pratense*). In one embodiment, the Red clover comprises formononetin, biochanin A and their glycosides in amounts determined by the method disclosed herein.

EXAMPLE 1

Approach to Model Development for Estimating the Contribution of Each Component to the Response of a Mixture The objective of this example is to establish a mathematical framework upon which a mathematical model is developed to describe and quantify activity of individual components in a mixture. The mathematical problem that arises can be formulated as follows. Suppose one had a number of samples of the same herbal preparation (for example, *Panax ginseng*) coming from different sources, each of which has a potentially different composition in terms of quantity of active components. Suppose the samples are labeled by an index "i" that runs from 1 to M. Suppose also that each sample contains N active ingredients labeled by index "j" that runs from 1 to N. The concentration of each ingredient can be determined and is denoted as $c(i,j)$ such that summing $c(i,j)$ from 1 to N over j gives 1 (or 100% as they all add up to the total amount in each sample) for all samples (denoted by i's). It should be assumed that it is known that the physiologic effect (activity) of each sample to be $A(i)$ as determined by some available empirical data. It should in general be assumed that activity A is an a priori unknown nonlinear function of the concentrations $c(i,j)$. This in some cases can be established via experimentation, whereby the function A versus either individual component concentrations or the total dose can be measured experimentally. The only other thing of note is that it must be assumed here that when simulations are performed, a certain type of nonlinear relationship has to be assumed for obtaining fits to empirical data. The problem at hand is to determine the form of the function $A(c(i,j))$ using the limited size of the data sets available. Note that the form of A is not unique but it depends on the choice of the basis set of functions used in representing the dependence of A on the individual concentrations. There may be various functions used for this purpose; polynomial, exponential or trigonometric, for example. It could be assumed naively that A was to be a linear combination of individual concentrations but this would immediately eliminate the possibility of either saturation effects or interactions between the ingredients (both inhibitive and synergistic).

Consequently, a much more reasonable approach is to expect A to be represented as a series of polynomials of $c(i,j)$ starting with linear functions of c, followed by bilinear combinations, then quadratic functions of c, then trilinear combinations, cubic functions of c, etc. In this case, the first task is to determine the highest order of the polynomial in the expansion that will be consistent with the amount of data available. On the other hand, it is generally expected that the activity at high concentrations should show saturation effects which are more consistent with sigmoidal dependence and hence an exponential series. These saturation effects may be readily handled with a Michaelis-Menton, or other type of limit, by including an appropriate compensating correction prior to other calculations. Once the function $A(c(i,j))$ is found, it will be necessary to find its maxima in the multi-dimensional space of all the individual concentrations (N-dimensional in general) to propose an optimal formulation of the medicinal extract. Moreover, if the individual pharmacokinetics of each ingredient are known for its transit through the gastro-intestinal system and the eliminating organs such as the liver and kidneys, the metabolites resulting from this process should be added to the space of components (for example, there could be K new metabolites) effectively enlarging the multidimensional simulations space from N to $N'=N+K$ (FIG. 1). In principle, this aspect does not add any conceptual complexity to the problem if it is quantitatively known the metabolic reactions for each of the drug's components. Therefore, this aspect will not be discussed further in this document. An additional layer of complexity can be added by putting error bars on the activity values since they come from multiple experimental assays of possibly different purity. The final complication involves the pharmacokinetic properties of each individual ingredient. In other words each constituent compound shows a different time course $c(i,j; t)$ following administration. The question then arises: how to compose the combination of ingredients to arrive at the optimal dose delivered to the organ at which the ingredients are supposed to be active.

What is of key importance, however, is the determination of the subset of active ingredients (which will be accomplished using a principal component analysis, for example) and, secondly, the nature of interactions between active ingredients which will be accomplished by nonlinear data-fitting methods.

If dose-response curves for a sufficiently large set of linearly-independent mixtures are available, models can be produced to describe the response to a large distribution of components.

EXAMPLE 2

Construction of a Model to Describe the Activity of Individual Components in a Mixture The objective of this example is to employ the approach described in Example 1 to construct a model to describe individual component activity in a mixture. This model will be used to estimate activity of individual components of a hypothetical mixture with pre-determined activities.

Figure 4:
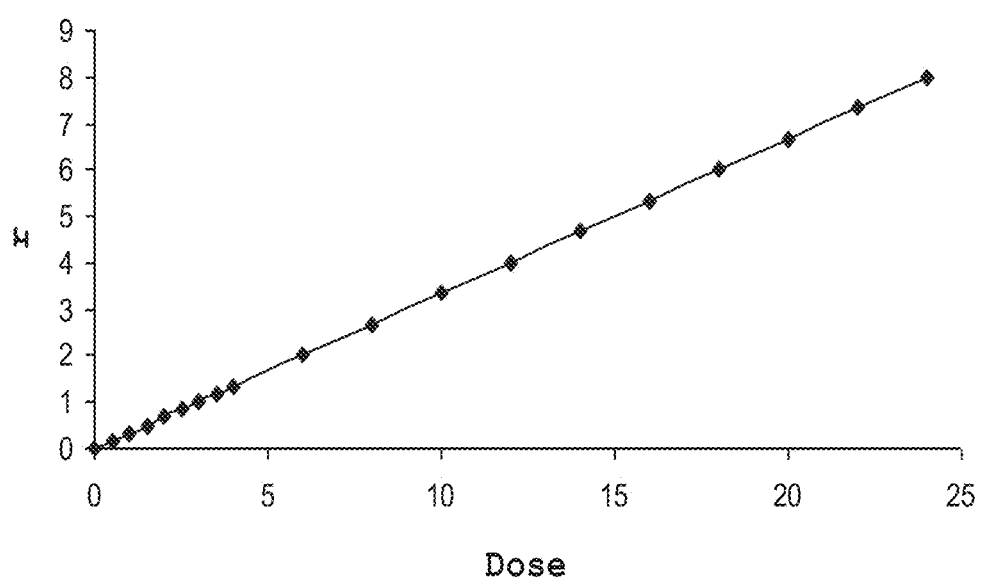
FIG. 4 shows a dose-response relationship of the Michaelis-Menton type, where r is a linear transformation of response in relationship to dose. r=response/(1-response).

The physiological reality of a dose-response relationship is that at low doses, responses are proportional to dose. However, response reaches a limit at higher doses. In this example, the Michaelis-Menton equation:

$$R = \frac{R_{max} \cdot C}{EC_{50} + C} \quad (4)$$

Where R is response, $R_{max}$ is maximum response, C is dose or concentration, and $EC_{50}$ is C that elicits 50% of $R_{max}$, is used to model this type of dose-response behavior (FIG. 2). To facilitate modeling, R is linearized using the following equation (FIG. 4):

$$r = \frac{R}{1-R} \quad (5)$$

In constructing the model, it is convenient to shift from considering the dose of a mixture, to considering the doses of the individual components. The first step in constructing the initial model is to choose a central reference point. The mean dose of each component across all the mixtures is obtained to provide a set of means. While any point could serve as this reference, best results are likely obtained if the reference is near the region of interest. The models are constructed using the difference between the doses at the point of interest, $d_i$, and the corresponding reference doses, $\bar{d}_1$. The transformed response at this dose, $\bar{r}$, is expected to be the mean of the doses.

As an initial model, the responses are assumed to be proportional to dose, for doses near a reference dose. This is equivalent to a model of weighted linear functions:

$$r \approx \bar{r} + \sum_i^N w_i(d_i - \bar{d}_i) \qquad (6)$$

A minimum of N linearly-independent mixtures are required to ensure that the system is linearly solvable. With data from more samples the system will be over-determined, and the optimal solution is obtained using least-squares.

Once the first model of physiological response is generated, it can be compared to the experimental data. In particular, the residuals, the differences between the model and the data are examined. At this stage, trends that have not been accounted for by the model are identified. The model can be improved by adding higher-order polynomial terms in single compound doses and terms in the products of pairs of doses. Degrees of correlation between the residuals and functions of these additional terms are calculated. A Pearson correlation coefficient is calculated between each of the possible additional terms and the residuals. Trends in the data not accounted for by the model should give rise to strong correlations, indicating that these terms should be added to the model. In practice it is expected that many terms will have little or no correlation. By excluding these from the model, problems of fitting many near-zero weights to the noise in the data are avoided. Ultimately the model may take the form:

$$r \approx \bar{r} + \sum_i w_i(d_i - \bar{d}_i) + \sum_i w'_i(d_i - \bar{d}_i)^2 + \sum_{i,j} w_{i,j}(d_i - \bar{d}_i)(d_j - \bar{d}_j) \qquad (7)$$

Where the first summation is just the linear contributions as in the previous equation, the second sum adds single-component non-linear behaviors, and the third sum adds two-component (pair-wise) interactions to the model. While this expression assumes that all possible square and pair terms are added, it is expected that only a few will be of real interest, and many may be ignored or omitted, or equivalently, the respective weights taken as zero. If applicable, higher-order polynomial and non-polynomial components may also be used.

As the model is improved through the process of adding terms to the model, the residuals should decrease in magnitude and become less ordered. Ultimately, a model should be obtained that adequately describes the data. As the model is developed, it may be desirable to use it to suggest locations to sample data that may help to reduce the uncertainties of the weights in the model or to better study any interesting patterns in the data.

In this example, a hypothetical mixture containing 15 components with predefined activities and interactions is examined (FIG. 6A). Compounds 2, 9, 10, 12 and 13 are active and compounds 4 and 10 (virtual compound 16) and compounds 7 and (virtual compound 17) are synergistic. For simplicity, relative potency has been ascribed a set of values ranging from 0 to 1, zero indicating no activity and 1 indicating maximum potency.

Figure 5:
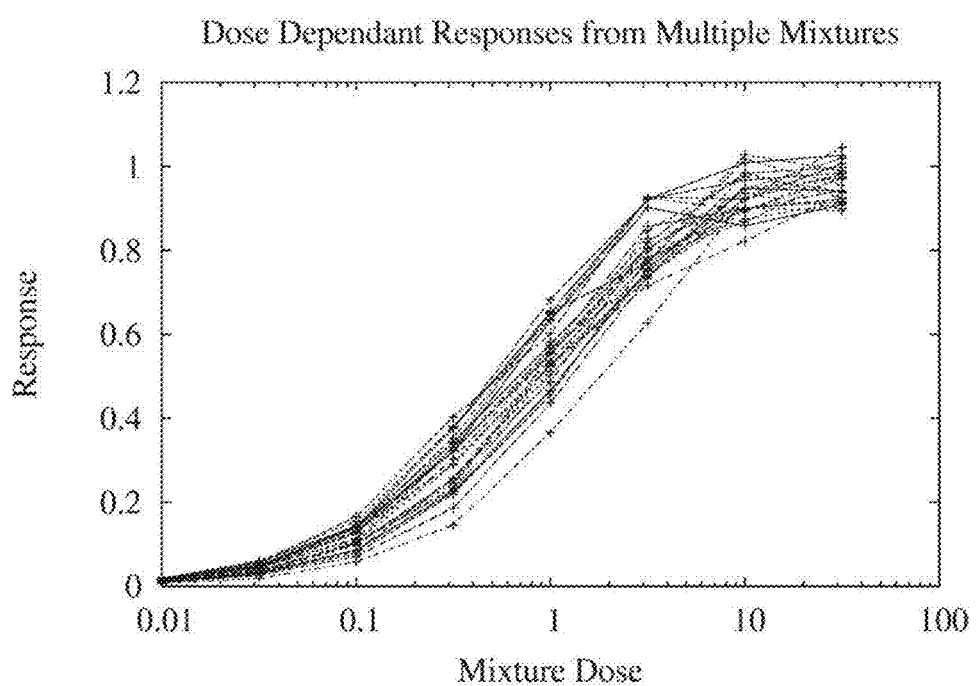
FIG. 5 shows a log dose-response relationship of 25 mixtures containing 15 hypothetical components. The error of each response measurement was assumed to be ±10%.

Twenty five mixtures were randomly generated and their relative quantities are listed on Table 1. A complete dose response curve is generated for each mixture (FIG. 5). The responses are listed on Table 2.

Using the model building approach described above, individual potency of each component was estimated (FIGS. 6A and 6B). These values were compared to that of the predetermined values. The established model was capable of correctly identifying the five active components (FIG. 6A), and the model could also identify pairs of components that are interacting with each other (FIG. 6B).

This simulation shows that active components and their interacting species can be identified without the need to use purified components to obtain the desired information. This approach will tremendously shorten the time to study a complicated mixture.

This methodology can be used to identify active components and their interactive species in more complicated mixtures which have different characteristics. This methodology can also be used to estimate permeability and rate of metabolism of the individual components in a mixture. The saturable processes can be described using either the Michaelis-Menton type of relationships or the modified forms thereof. In this invention, this approach will also be used to produce pharmacokinetic parameters for individual components.

TABLE 1

The Amount of 15 Components In Each of The 25 Mixtures

| Mixture | Component | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 1 | 0.73 | 0.06 | 0.76 | 0.35 | 0.61 | 0.75 | 0.25 | 0.67 | 1.00 | 0.02 | 0.39 | 0.24 | 0.81 | 0.94 | 0.96 |
| 2 | 0.31 | 0.20 | 0.24 | 0.03 | 0.20 | 0.46 | 0.10 | 0.32 | 0.49 | 0.97 | 0.64 | 0.49 | 0.36 | 0.84 | 0.36 |
| 3 | 0.67 | 0.07 | 0.62 | 0.43 | 0.43 | 0.70 | 0.45 | 0.72 | 0.67 | 0.12 | 0.22 | 0.09 | 0.44 | 0.45 | 0.86 |
| 4 | 0.73 | 0.53 | 0.63 | 0.90 | 0.32 | 0.01 | 0.28 | 0.53 | 0.84 | 0.61 | 0.52 | 0.32 | 0.90 | 0.93 | 0.13 |
| 5 | 0.10 | 0.81 | 0.84 | 0.51 | 0.51 | 0.34 | 0.50 | 0.37 | 0.57 | 0.58 | 0.36 | 0.28 | 0.61 | 0.72 | 0.29 |
| 6 | 0.78 | 0.59 | 1.00 | 0.79 | 0.48 | 0.67 | 0.21 | 0.56 | 0.52 | 0.55 | 0.89 | 0.14 | 0.51 | 0.36 | 0.79 |
| 7 | 0.52 | 0.30 | 0.26 | 0.82 | 0.81 | 1.00 | 0.54 | 0.51 | 0.33 | 0.20 | 0.50 | 0.03 | 0.49 | 0.89 | 0.25 |
| 8 | 0.80 | 0.42 | 0.95 | 0.68 | 0.22 | 0.51 | 0.49 | 0.19 | 0.94 | 0.32 | 0.57 | 0.36 | 0.11 | 0.66 | 0.51 |
| 9 | 0.12 | 0.58 | 0.79 | 0.55 | 0.78 | 0.26 | 0.85 | 0.63 | 0.68 | 0.20 | 0.39 | 0.65 | 0.44 | 0.40 | 0.91 |
| 10 | 0.95 | 0.87 | 0.97 | 0.66 | 0.13 | 0.49 | 0.87 | 0.44 | 0.62 | 0.81 | 0.93 | 0.58 | 0.71 | 0.46 | 0.76 |
| 11 | 0.99 | 0.79 | 0.98 | 0.45 | 0.01 | 0.07 | 0.48 | 0.59 | 0.96 | 0.25 | 0.46 | 0.26 | 0.68 | 0.41 | 0.21 |
| 12 | 0.23 | 0.83 | 0.22 | 0.55 | 0.60 | 0.91 | 0.05 | 0.03 | 0.17 | 0.41 | 0.21 | 0.39 | 0.26 | 0.12 | 0.38 |
| 13 | 0.90 | 0.88 | 0.26 | 0.16 | 0.90 | 0.55 | 0.07 | 0.43 | 0.56 | 0.78 | 0.53 | 0.91 | 0.11 | 0.96 | 0.42 |
| 14 | 0.62 | 0.68 | 0.20 | 0.53 | 0.69 | 0.57 | 0.23 | 0.64 | 0.01 | 0.35 | 0.64 | 0.87 | 0.82 | 0.94 | 0.96 |

TABLE 1-continued

The Amount of 15 Components In Each of The 25 Mixtures

| Mixture | Component | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 15 | 0.39 | 0.87 | 0.34 | 0.67 | 0.38 | 0.27 | 0.59 | 0.45 | 0.83 | 0.79 | 0.08 | 0.22 | 0.45 | 0.05 | 0.93 |
| 16 | 0.46 | 0.66 | 0.13 | 0.38 | 0.36 | 0.47 | 0.34 | 0.92 | 0.53 | 0.43 | 0.82 | 0.07 | 0.51 | 0.65 | 0.27 |
| 17 | 0.93 | 0.14 | 0.28 | 0.41 | 0.33 | 0.20 | 0.84 | 0.90 | 0.64 | 0.07 | 0.29 | 0.71 | 0.22 | 0.09 | 0.56 |
| 18 | 0.74 | 0.44 | 0.09 | 0.85 | 0.87 | 0.20 | 0.20 | 0.61 | 0.88 | 0.40 | 0.66 | 0.37 | 0.89 | 0.64 | 0.16 |
| 19 | 0.85 | 1.00 | 0.91 | 0.83 | 0.23 | 0.18 | 0.90 | 0.65 | 0.93 | 0.85 | 0.23 | 0.22 | 0.07 | 0.27 | 0.56 |
| 20 | 0.19 | 0.32 | 0.77 | 0.27 | 0.12 | 0.03 | 0.34 | 0.30 | 0.98 | 0.21 | 0.04 | 0.98 | 0.32 | 0.92 | 0.94 |
| 21 | 0.25 | 0.52 | 0.82 | 0.25 | 0.12 | 0.92 | 0.06 | 0.68 | 0.30 | 0.19 | 0.96 | 0.13 | 0.52 | 0.97 | 0.99 |
| 22 | 0.16 | 0.12 | 0.87 | 0.39 | 0.71 | 0.01 | 0.23 | 0.62 | 0.34 | 0.12 | 0.83 | 0.89 | 0.90 | 0.15 | 0.37 |
| 23 | 0.57 | 0.01 | 0.58 | 0.51 | 0.61 | 0.83 | 0.20 | 0.84 | 0.07 | 0.27 | 0.13 | 0.52 | 0.98 | 0.71 | 0.48 |
| 24 | 0.58 | 0.04 | 0.28 | 0.75 | 0.89 | 0.68 | 0.40 | 0.33 | 0.91 | 0.73 | 0.35 | 0.37 | 0.96 | 0.20 | 0.14 |
| 25 | 0.06 | 0.95 | 0.11 | 0.57 | 0.80 | 0.37 | 0.38 | 0.40 | 0.41 | 0.23 | 0.49 | 0.09 | 0.38 | 0.34 | 0.12 |

TABLE 2

Dose-Response Relationship of The 25 Mixtures

| Mixture | Relative Dose | | | | | | | |
|---|---|---|---|---|---|---|---|---|
| | 0.01 | 0.03 | 0.1 | 0.3 | 1 | 3 | 10 | 30 |
| 1 | 0.01 | 0.03 | 0.08 | 0.23 | 0.48 | 0.76 | 0.91 | 0.96 |
| 2 | 0.01 | 0.03 | 0.10 | 0.24 | 0.50 | 0.73 | 0.79 | 1.02 |
| 3 | 0.01 | 0.02 | 0.06 | 0.16 | 0.38 | 0.66 | 0.89 | 0.99 |
| 4 | 0.02 | 0.05 | 0.13 | 0.33 | 0.60 | 0.82 | 0.93 | 0.98 |
| 5 | 0.02 | 0.05 | 0.14 | 0.33 | 0.62 | 0.85 | 0.92 | 0.96 |
| 6 | 0.01 | 0.04 | 0.11 | 0.28 | 0.54 | 0.78 | 0.94 | 0.96 |
| 7 | 0.01 | 0.02 | 0.07 | 0.19 | 0.42 | 0.67 | 0.75 | 1.05 |
| 8 | 0.01 | 0.03 | 0.10 | 0.26 | 0.52 | 0.79 | 0.92 | 0.94 |
| 9 | 0.02 | 0.05 | 0.13 | 0.33 | 0.62 | 0.82 | 0.97 | 0.99 |
| 10 | 0.02 | 0.06 | 0.17 | 0.39 | 0.65 | 0.88 | 0.95 | 0.99 |
| 11 | 0.02 | 0.05 | 0.14 | 0.33 | 0.61 | 0.83 | 0.94 | 0.99 |
| 12 | 0.01 | 0.04 | 0.12 | 0.31 | 0.59 | 0.84 | 0.96 | 0.97 |
| 13 | 0.02 | 0.06 | 0.16 | 0.38 | 0.65 | 0.87 | 0.93 | 0.96 |
| 14 | 0.02 | 0.05 | 0.15 | 0.37 | 0.64 | 0.86 | 0.95 | 0.98 |
| 15 | 0.02 | 0.05 | 0.14 | 0.34 | 0.61 | 0.84 | 0.94 | 0.96 |
| 16 | 0.01 | 0.04 | 0.10 | 0.27 | 0.52 | 0.78 | 0.91 | 0.63 |
| 17 | 0.01 | 0.03 | 0.10 | 0.25 | 0.54 | 0.82 | 0.94 | 0.97 |
| 18 | 0.01 | 0.05 | 0.13 | 0.31 | 0.57 | 0.80 | 0.94 | 0.90 |
| 19 | 0.02 | 0.05 | 0.14 | 0.35 | 0.65 | 0.88 | 0.97 | 0.99 |
| 20 | 0.02 | 0.05 | 0.13 | 0.33 | 0.63 | 0.83 | 0.95 | 1.00 |
| 21 | 0.01 | 0.03 | 0.09 | 0.24 | 0.50 | 0.74 | 0.88 | 0.95 |
| 22 | 0.01 | 0.04 | 0.12 | 0.30 | 0.57 | 0.79 | 0.94 | 0.98 |
| 23 | 0.01 | 0.03 | 0.09 | 0.23 | 0.47 | 0.71 | 0.78 | 1.03 |
| 24 | 0.01 | 0.04 | 0.11 | 0.27 | 0.55 | 0.79 | 0.93 | 0.99 |
| 25 | 0.01 | 0.04 | 0.12 | 0.30 | 0.57 | 0.82 | 0.92 | 0.97 |

EXAMPLE 3

Detailed Approach in Identifying Active Components and the Interacting Species

The objective of this example is to outline an approach to mine all the active and interacting components in a mixture. In an herbal extract, there may exist hidden unknowns that have not been previously identified. This may occur when the components are transparent to quantitative or qualitative analysis; for example, components may have very little UV absorbance when a UV detector is used for identifying individual components. This aspect makes the problem open-ended from the point of view of model development and refinement in the course of experimentation.

This problem was looked at from a couple of different angles stated below. 1) It could be determined that by accounting for all the known variables, it is still not possible to describe the activity properly which will warrant additional empirical studies of the composition. 2) It is possible to assume that unknowns always exist and they can be lumped together as one group without our explicit knowledge of their identities.

A criterion for the existence of active hidden components can be introduced whereby a variability of more than the noise of an assay (for example, 15%) within a given set of experimental data indicates the presence of additional active components.

Moreover, a simple extension of the present modeling methodology can be accomplished such that several different types of activities may be assessed simultaneously and the activity function: $A_k$ ($c_i$, $c_j$) becomes a vector in a multidimensional space instead of a scalar. It can be optimized for a specific activity using the same procedures as those outlined above.

Below are illustrations of some pertinent mathematical approaches that allow one to solve the mathematical problem at hand, using a typical synthetic data set (shown in Tables 3 and 4). First address the issue of the data fit using a nonlinear model was addressed. In this case, the number of components may be either the actual one identified empirically or reduced to only the active component set using the principal component analysis approach or any other dimensionality reduction method.

APPROACH #1: Curve Fitting Using Nonlinear Regression Analysis

Here, the hypothetical example consists of a 15-component herbal medication. Table 3 is a summary of concentration information for each of the 25 hypothetical samples, each of which contains 15 independent ingredients. Table 4 shows a dose-response value for 25 hypothetical samples whose activity is measured at 8 different dose values. In summary there were 1+N+(N*(N+1))/2=121; N=15, representing the number of parameters to be determined by the fitting procedure, and 200 data points provided from experiment.

The main task is to find the sensitivity coefficients that minimize the expression $$\text{Min}_{\alpha,\beta}\{\Sigma_i(F(\alpha,\beta;c)-R)^2\}; i=1,2,\ldots,200 \quad (8)$$

using a nonlinear regression analysis.

TABLE 3

The Amount of The 15 Components In Each of The 25 Mixtures (Hypothetical Sample)

| Samples | Components |  |  |  |  |  |  |  |  |  |  |  |  |  |  |
|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 |
| 1 | 6.440 | 3.415 | 0.014 | 0.000 | 0.003 | 0.173 | 0.000 | 0.000 | 0.676 | 0.002 | 0.009 | 0.000 | 0.030 | 0.000 | 0.183 |
| 2 | 0.000 | 1.371 | 0.119 | 3.847 | 0.003 | 0.000 | 0.208 | 0.002 | 0.551 | 0.000 | 0.063 | 0.000 | 0.000 | 0.005 | 0.017 |
| 3 | 0.000 | 0.607 | 0.000 | 0.004 | 0.000 | 2.500 | 2.758 | 0.001 | 0.016 | 0.047 | 0.008 | 0.023 | 0.000 | 0.144 | 0.001 |
| 4 | 0.000 | 0.004 | 0.024 | 0.253 | 0.000 | 0.002 | 0.290 | 0.034 | 0.001 | 0.899 | 0.000 | 4.407 | 0.015 | 0.000 | 0.800 |
| 5 | 5.041 | 0.546 | 0.013 | 0.000 | 1.473 | 0.013 | 0.401 | 0.049 | 0.000 | 0.083 | 0.000 | 0.002 | 0.000 | 0.001 | 0.000 |
| 6 | 0.002 | 0.000 | 0.000 | 0.006 | 0.221 | 0.009 | 0.000 | 0.168 | 0.030 | 0.000 | 0.000 | 0.010 | 2.388 | 2.014 | 1.279 |
| 7 | 0.000 | 0.015 | 0.001 | 0.000 | 7.508 | 3.342 | 0.000 | 0.004 | 0.129 | 0.000 | 0.055 | 0.362 | 0.000 | 0.006 | 0.263 |
| 8 | 2.130 | 0.003 | 0.079 | 0.000 | 0.000 | 0.014 | 0.000 | 0.025 | 0.002 | 0.002 | 0.000 | 9.245 | 0.283 | 0.000 | 0.983 |
| 9 | 0.029 | 0.037 | 0.001 | 0.000 | 0.054 | 2.614 | 0.001 | 0.000 | 0.000 | 1.659 | 0.156 | 0.000 | 0.008 | 0.288 | 0.003 |
| 10 | 0.001 | 0.000 | 0.000 | 0.000 | 0.034 | 0.130 | 0.000 | 0.010 | 0.695 | 0.022 | 7.537 | 0.000 | 0.002 | 0.210 | 2.018 |
| 11 | 0.189 | 1.072 | 0.010 | 0.064 | 2.656 | 0.002 | 0.000 | 0.291 | 0.000 | 0.000 | 0.000 | 0.046 | 0.000 | 0.011 | 0.006 |
| 12 | 0.000 | 0.000 | 5.867 | 0.137 | 0.004 | 0.005 | 0.001 | 0.001 | 0.258 | 1.011 | 0.000 | 3.242 | 0.000 | 0.021 | 0.017 |
| 13 | 0.002 | 0.584 | 0.026 | 0.006 | 0.000 | 0.000 | 0.085 | 0.011 | 0.001 | 0.000 | 0.018 | 0.000 | 9.246 | 1.547 | 3.552 |
| 14 | 0.009 | 0.000 | 1.680 | 0.574 | 0.000 | 3.393 | 0.252 | 0.028 | 0.201 | 0.003 | 0.001 | 0.000 | 0.105 | 0.000 | 0.000 |
| 15 | 1.914 | 0.012 | 0.006 | 0.001 | 0.000 | 0.465 | 2.587 | 0.197 | 0.000 | 0.033 | 0.000 | 0.001 | 0.000 | 0.025 | 0.339 |
| 16 | 0.000 | 0.001 | 0.000 | 0.035 | 0.000 | 0.303 | 0.004 | 0.068 | 0.000 | 0.190 | 0.018 | 6.994 | 0.000 | 0.013 | 0.689 |
| 17 | 0.002 | 0.000 | 1.407 | 0.000 | 0.147 | 0.008 | 0.004 | 3.911 | 0.000 | 0.030 | 0.038 | 2.370 | 0.000 | 0.197 | 0.001 |
| 18 | 0.027 | 0.002 | 0.017 | 0.000 | 0.021 | 2.568 | 2.243 | 0.000 | 0.399 | 0.073 | 0.001 | 0.000 | 0.381 | 0.002 | 0.000 |
| 19 | 0.402 | 2.792 | 0.144 | 0.000 | 0.000 | 0.002 | 0.000 | 0.000 | 0.001 | 0.109 | 0.040 | 0.006 | 0.003 | 0.019 | 4.075 |
| 20 | 0.569 | 0.000 | 0.000 | 0.085 | 0.002 | 0.001 | 0.005 | 0.000 | 0.028 | 1.659 | 0.000 | 0.000 | 0.710 | 2.857 | 0.025 |
| 21 | 0.001 | 0.694 | 0.005 | 0.000 | 0.000 | 0.000 | 0.000 | 0.966 | 0.069 | 0.556 | 0.053 | 0.000 | 4.968 | 0.001 | 0.008 |
| 22 | 0.002 | 0.000 | 0.000 | 0.014 | 0.202 | 0.001 | 0.084 | 0.004 | 0.342 | 0.076 | 0.008 | 0.000 | 2.123 | 0.000 | 2.591 |
| 23 | 0.266 | 0.665 | 0.091 | 0.011 | 0.002 | 3.356 | 1.331 | 0.002 | 0.000 | 0.001 | 0.000 | 0.008 | 0.000 | 0.000 | 0.113 |
| 24 | 0.000 | 0.018 | 0.000 | 0.021 | 0.025 | 0.296 | 0.315 | 0.683 | 0.000 | 4.185 | 0.002 | 0.001 | 0.216 | 0.001 | 0.000 |
| 25 | 0.000 | 0.000 | 0.001 | 0.171 | 2.108 | 0.019 | 0.006 | 0.000 | 0.007 | 0.000 | 3.230 | 0.010 | 0.000 | 0.133 | 1.144 |

TABLE 4

Dose-Response Relationship of The 25 Mixtures (Hypothetical Sample)

| Samples | Doses |  |  |  |  |  |  |  |
|---|---|---|---|---|---|---|---|---|
|  | 0.01 | 0.03 | 0.1 | 0.3 | 1 | 3 | 10 | 30 |
| 1 | 0.031 | 0.091 | 0.241 | 0.501 | 0.761 | 0.909 | 0.969 | 0.990 |
| 2 | 0.013 | 0.041 | 0.119 | 0.299 | 0.575 | 0.810 | 0.931 | 0.977 |
| 3 | 0.006 | 0.018 | 0.055 | 0.155 | 0.367 | 0.647 | 0.853 | 0.948 |
| 4 | 0.029 | 0.086 | 0.230 | 0.486 | 0.749 | 0.904 | 0.968 | 0.990 |
| 5 | 0.005 | 0.016 | 0.048 | 0.138 | 0.335 | 0.615 | 0.834 | 0.941 |
| 6 | 0.005 | 0.016 | 0.048 | 0.137 | 0.335 | 0.614 | 0.834 | 0.941 |
| 7 | 0.003 | 0.008 | 0.026 | 0.078 | 0.212 | 0.460 | 0.729 | 0.895 |
| 8 | 0.058 | 0.164 | 0.383 | 0.662 | 0.861 | 0.951 | 0.984 | 0.995 |
| 9 | 0.001 | 0.004 | 0.012 | 0.038 | 0.110 | 0.282 | 0.553 | 0.797 |
| 10 | 0.001 | 0.002 | 0.007 | 0.022 | 0.066 | 0.182 | 0.413 | 0.690 |
| 11 | 0.010 | 0.031 | 0.091 | 0.241 | 0.502 | 0.761 | 0.910 | 0.970 |
| 12 | 0.022 | 0.066 | 0.182 | 0.414 | 0.691 | 0.876 | 0.957 | 0.986 |
| 13 | 0.024 | 0.071 | 0.195 | 0.433 | 0.707 | 0.884 | 0.960 | 0.987 |
| 14 | 0.001 | 0.002 | 0.005 | 0.016 | 0.049 | 0.140 | 0.340 | 0.620 |
| 15 | 0.000 | 0.001 | 0.002 | 0.007 | 0.021 | 0.064 | 0.178 | 0.407 |
| 16 | 0.044 | 0.128 | 0.318 | 0.596 | 0.823 | 0.936 | 0.979 | 0.993 |
| 17 | 0.016 | 0.048 | 0.136 | 0.333 | 0.612 | 0.833 | 0.940 | 0.980 |
| 18 | 0.001 | 0.004 | 0.013 | 0.039 | 0.115 | 0.291 | 0.564 | 0.804 |
| 19 | 0.025 | 0.075 | 0.203 | 0.446 | 0.718 | 0.890 | 0.962 | 0.988 |
| 20 | 0.002 | 0.008 | 0.024 | 0.072 | 0.198 | 0.439 | 0.712 | 0.886 |
| 21 | 0.038 | 0.112 | 0.285 | 0.558 | 0.800 | 0.927 | 0.976 | 0.992 |
| 22 | 0.005 | 0.015 | 0.045 | 0.129 | 0.319 | 0.598 | 0.824 | 0.937 |
| 23 | 0.006 | 0.019 | 0.058 | 0.163 | 0.381 | 0.661 | 0.860 | 0.951 |
| 24 | 0.003 | 0.009 | 0.027 | 0.081 | 0.219 | 0.470 | 0.737 | 0.899 |
| 25 | 0.000 | 0.000 | 0.001 | 0.004 | 0.011 | 0.034 | 0.100 | 0.260 |

FIG. 7 is a schematic illustration of the dose-activity dependence for the set of different combinations of compounds involving the same basic ingredients. Each curve represents a different set of activity coefficients. It is shown how the choice of these coefficients affects the overall activity of the compound and how the top curve would be chosen to represent the most efficacious combination.

The available data for study is a set of administered doses of the (mixed) compounds and a corresponding response. In a real case, these doses are likely imprecisely known and the response is prone to some (hopefully negligibly small) measurement uncertainty.

The method proposed is a generalization of an earlier approach in which the same mixture at several strengths was administered. The data was treated at differing strengths separately and then were combined in follow-up processing. By treating each strength case as a separate dose, the process was simplified. There is a positive effect on the accuracy of some cases.

Besides a direct linear contribution from the dose of each component, the model considered includes additional pseudo-compound components. One function of these is to allow consideration of synergistic interactions between components, another could be antagonistic. Doses of additional pseudo-compounds are constructed as the products of the doses of two other compounds. To prevent such pseudo-compounds from interfering with the parent compounds, they are constructed using an orthogonal polynomial. Note that if desired, higher order pseudo-compounds may be constructed from another pseudo-compound.

A second type of pseudo-compounds is necessary to work with large numbers of compounds without requiring enormous amounts of dose-response data. In this case, cluster analysis techniques identify several compounds with similar patterns of dosing. Note that in FIG. 7, several areas were seen where the dose-response curves for different components are very similar. The similar patterns of dosing are nearly co-linear, are more common in such large sets and require large numbers of dose-response pairs to accurately solve for the individual components. Replacing the members of these clusters with either a synthetic or representative member, a pseudo-compound representing the cluster is considered. If the cluster should prove to be important, it may be necessary to obtain additional dose-response pairs to properly resolve the contributions of individual members.

The creation of pseudo-compounds results in a purely linear system is discussed. The vector of responses, R, and dose matrix, $\underline{D}$, lead to the simple matrix equation R=$\underline{D}$S, where the unknown vector S is a sensitivity to each compound. The dose-sensitivity products, or activities, resulting from each compound (and pseudo-compound) add to produce the observed response. Note that the sensitivity, especially of pseudo-compounds, may be either positive or negative.

The essential problem is one of solving an under-determined system. In general, this is not possible, however here it is achieved by assuming that many of the terms are negligible. Treating these values as zeros, the problem is simplified to an over-determined system. This reduced system is then solved. By bootstrapping, estimates of the uncertainties in the solution may be obtained. The level of noise expected in the responses of any realistic data set is such that the system must be reduced to a point at which it is significantly over-determined before an accurate solution may be obtained. If the reduction results in a system of equations that is only slightly over-determined, then noise present in the data leads to large uncertainties in the result. Thus the number of data points available must be significantly larger than the number of unknowns to be solved. Unfortunately, this number is not known at the outset.

As the number of dose-response pairs increases, the effect of noise in the response is decreased. Mathematically, this is equivalent to averaging a number of repeated measurements, obtaining a more accurate value. In the simulated data sets, the strongest activities are consistently and accurately obtained. However, any error associated with a large component "contaminates" the rest of the data as the difference will be assigned to other, lower activity components where the error represents a much larger proportional contribution.

The first step is to calculate (linear) correlations between the observed responses and doses. Components with weak (or no) correlations are taken to be inactive. In practice, on simulated data, this assumption is verified. Strong correlations tend to be from both strongly active components and a few weakly- or non-active components. Once a small number of the system components have been identified as relevant, by their strong correlation with the response, the simplified system with only those components may then be solved. The over-determined systems do not have true solutions, however the solution that optimally solves the system, while minimizing the $|\underline{D}S-R|^2$ difference (least-squares solution), may be obtained.

To estimate result uncertainty, a bootstrapping process is used. One hundred thousand dose-response sets are constructed by selecting pairs (with replacement) from the observed pair set. Each constructed set is then solved, and the statistics from the distribution of these solutions are then taken as estimates for the solution of the observed pair set. The resulting solution may then be subtracted from the observed data to obtain a residual. Calculating correlations against the residual may reveal additional components with significant activities not solved for in the reduced system. Other components, solved in the reduced system may have been found to have only weak activity. The set of components included in the reduced system may be adjusted and a new solution obtained. By repeating, a final set of sensitivities that describes the data may be obtained.

APPROACH #2: Principal Component Analysis

Subset Selection-Principal Component Analysis (PCA) is used for dimensionality reduction in a data set by retaining the characteristics of the data set that contribute most to its variance. Sample results are shown in FIG. 8.

Note that in the synthetic data set studied (FIG. 9), 10 transformed variables out of the original 15 cover 80% of the variation in data. This suggests very little correlation/dependence/interaction and the information is spread over all the variables. Table 5 gives the results of the PCA method's application to the synthetic data set in Tables 3 and 4. It shows the linear coefficients $\alpha_i$ in the top row (i=1, ..., 15) followed by 15 rows of pair coefficients $\beta_{i,j}$ where i= 1, ..., 15 and j=1, ..., 15, yielding a 15×16 matrix. The highlighted coefficients are those retained by the PCA for the response function that covers the whole data set.

The data set discussed in this example can be adequately represented by the following response function using the PCA method, where there has been a substantial reduction of the parameter space to include only four coefficients: two for linear effects (components $x_6$ and $x_{12}$) as well as two for interactions (synergistic for components $x_{13}$ and $x_{15}$, antagonistic for components $x_1$ and $x_{15}$). The remaining variables are insignificant and can be ignored. Taking only the highlighted coefficients from Table 5, a corresponding response function was constructed:

$$\text{Response}=0.5248x_6-0.4893x_{12}+0.4745x_{13}x_{15}-0.5703x_1x_{15}$$

TABLE 5

Response Analysis Data (16 x 15 set)

| 0.0574 | 0.0183 | 0.0051 | 0.0130 | 0.0613 | *0.5248* | 0.2546 | -0.0303 | -0.0001 | 0.0486 | -0.0657 | *-0.4893* | -0.1484 | -0.0475 | -0.2019 |
|---|---|---|---|---|---|---|---|---|---|---|---|---|---|---|
| 0.4271 | 0.0919 | 0.0553 | 0.0077 | 0.1988 | 0.4830 | 0.3410 | 0.0038 | -0.0039 | -0.1258 | -0.2323 | 0.2944 | -0.6736 | -0.2971 | *-0.5703* |
| 0.0919 | 0.0137 | 0.0220 | 0.0020 | 0.0384 | 0.2253 | 0.1337 | -0.0021 | -0.0014 | -0.0132 | -0.0786 | 0.0288 | -0.1948 | -0.0826 | -0.1832 |
| 0.0553 | 0.0220 | -0.0094 | 0.0008 | 0.0339 | -0.1229 | -0.0486 | 0.0043 | 0.0004 | -0.0372 | 0.0157 | 0.0793 | -0.0072 | -0.0081 | 0.0216 |
| 0.0077 | 0.0020 | 0.0008 | 0.0007 | 0.0053 | 0.0288 | 0.0152 | -0.0014 | 0.0000 | 0.0007 | -0.0054 | -0.0193 | -0.0142 | -0.0055 | -0.0154 |
| 0.1988 | 0.0384 | 0.0339 | 0.0053 | 0.0929 | 0.3798 | 0.2335 | -0.0042 | -0.0022 | -0.0393 | -0.1361 | 0.0469 | -0.3621 | -0.1548 | -0.3307 |
| 0.4830 | 0.2253 | -0.1229 | 0.0288 | 0.3798 | -0.6096 | -0.2332 | -0.0121 | 0.0066 | -0.2461 | 0.1736 | -0.2226 | 0.0049 | -0.0180 | 0.1625 |
| 0.3410 | 0.1337 | -0.0486 | 0.0152 | 0.2335 | -0.2332 | -0.0559 | -0.0028 | 0.0024 | -0.1581 | 0.0382 | 0.0017 | -0.1484 | -0.0771 | -0.0397 |
| 0.0038 | -0.0021 | 0.0043 | -0.0014 | -0.0042 | -0.0121 | -0.0026 | 0.0030 | -0.0003 | -0.0047 | -0.0077 | 0.0587 | -0.0162 | -0.0083 | -0.0103 |
| -0.0039 | -0.0014 | 0.0004 | 0.0000 | -0.0022 | 0.0066 | 0.0024 | -0.0003 | 0.0000 | 0.0024 | -0.0005 | -0.0056 | 0.0015 | 0.0010 | -0.0004 |
| -0.1258 | -0.0132 | -0.0372 | 0.0007 | -0.0393 | -0.2461 | -0.1581 | -0.0047 | 0.0024 | 0.0291 | 0.1153 | -0.1782 | 0.2810 | 0.1227 | 0.2514 |
| -0.2323 | -0.0786 | 0.0157 | -0.0054 | -0.1361 | 0.1736 | 0.0362 | -0.0077 | -0.0005 | 0.1153 | 0.0059 | -0.1886 | 0.1555 | 0.0794 | 0.0877 |
| 0.2944 | 0.0288 | 0.0793 | -0.0193 | 0.0469 | -0.2226 | 0.0017 | 0.0587 | -0.0056 | -0.1782 | -0.1886 | 1.2199 | -0.5192 | -0.2556 | -0.3407 |
| -0.6736 | -0.1948 | -0.0072 | -0.0142 | -0.3621 | 0.0049 | -0.1484 | -0.0162 | 0.0015 | 0.2810 | 0.1555 | -0.5192 | 0.6934 | 0.3248 | *0.4745* |
| -0.2971 | -0.0826 | -0.0081 | -0.0055 | -0.1548 | -0.0180 | -0.0771 | -0.0083 | 0.0010 | 0.1227 | 0.0794 | -0.2556 | 0.3248 | 0.1515 | 0.2278 |
| -0.5703 | -0.1832 | 0.0216 | -0.0154 | -0.3307 | 0.1625 | -0.0397 | -0.0103 | -0.0004 | 0.2514 | 0.0677 | -0.3407 | 0.4745 | 0.2278 | 0.2850 |

Now some general comments about subset selection in the regression analysis are made. The choice of a model for a given set of data with many variables may pose a challenge. When there are many predictors (with many possible interactions), it can be difficult to find a good model. The question arises which main effects should be included; and an associated question is which interactions to include. Model selection tries to simplify this task. This is an "unsolved" problem in statistics: there are no magic procedures to obtain the "best model". Data mining can be used for model selection. To implement this, there was a need for a criterion or benchmark to compare two models, and a search strategy. With a limited number of predictors, it is possible to search all possible models.

Possible criteria are now examined. $R^2$ is not a good criterion, as it always increases with model size, and hence erroneously suggests that an optimum result would be obtained by taking the biggest model (Using adjusted $R^2$ is better, since it penalizes bigger models.) Mallows' $C_p$ (named for Colin Mallows) is mostly used as a stopping rule in stepwise regression. It is similar to Akaike's information criterion, and depends less on the number of effects on a model than $R^2$. It is defined, for a subset of P regressors out of the total set of regressors K, as $$\frac{\sum_{i=1,N}(Y_i - Y_{ip})}{S^2} - N + 2P \quad (9)$$

where $$\sum_{i=1,N}(Y_i - Y_{ip})$$

is the error sum of squares for the model, $Y_{ip}$ is the ith predicted value of Y out of the P regressors, $S^2$ is the residual mean square after regression on the complete set of regressors, and N is the sample size. Akaike's Information Criterion (AIC) and Schwarz's BIC are also considered. One search strategy is the "best subset" search, which involves searching all possible models and taking the one with highest adjusted $R^2$ or lowest $C_p$. A stepwise search (forward, backward or both) involves the choosing of an initial model and taking the biggest jump (up or down) within the selected criterion. The implementation in R Software Package includes a "Best subset" search which uses adjusted $R^2$, $C_p$ or BIC and does exhaustive searches with the branch-and-bound algorithm, and a stepwise search, which works by minimizing the Akaike Information Criterion (AIC).

Model Fitting: Other Possibilities

Multiple Linear Regression may not be enough. Using optimization to get a better fitting function may result in getting a non-concave function after interpolation. A concave function may be needed to find the maximal response easily.

$$\min_{\alpha,r,Q} \sum_{x=1}^{N} \left(A - \alpha - r^T x - \frac{1}{2}x^T Q x\right)^2 \quad (10)$$

$$\text{s.t.} - Q \geq 0$$

Where x is a vector representation of the ingredient compounds, $x^T$ is its transpose, A the activity, Q is an optimization parameter, and α is a vector of linear coefficients in the activity function. Now it must be decided whether to use generalized linear regression or logistic regression.

Subset Selection: Results

Selected variables (components) are chosen as $x_2$, $x_{12}$, $x_{13}$, $x_1 x_{15}$, $x_{10} x_{12}$. The resulting model is:

$$A = \alpha_0 + \alpha_2 x_2 + \alpha_{12} x_{12} + \alpha_{13} x_{13} + \beta_{1,15} x_1 x_{15} + \beta_{10,12} x_{10} x_{12} \quad (11)$$

The fitted model is:

$$A = 0.16 + 0.25 x_2 + 0.10 x_{12} + 0.05 x_{13} - 0.13 x_1 x_{15} + 0.04 x_{10} x_{12} \quad (12)$$

Where the final term represents synergism and the second-to-last term represents inhibition. The linear regression results give an adjusted $R^2$ of 0.9.

Finding Maximal Response

A possibly non-concave interpolated function was considered:

$$A = \alpha_0 + \sum_{i=1}^{n} \alpha_i x_i + \sum_{i=1}^{n} \sum_{j=1}^{n} \beta_{i,j} x_i x_j \quad (13)$$

Global optimization was used to find the maximal response over the range of all possible (or interesting) concentrations:

$$\max_{x} \alpha_0 + \sum_{i=1}^{n} \alpha_i x_i + \sum_{i=1}^{n} \sum_{j=1}^{n} \beta_{i,j} x_i x_j \quad (14)$$

$$\text{s.t.} \sum_{i=1}^{n} x_i = 1, \quad x_i \geq 0, \forall i$$

All other variables were fixed except for two and analyzed the graphs of the responses.

In order to determine which components interact significantly (25% criterion), estimated values were compared for their activities with the observed ones. If the observed values differ by much (>25%), this indicates the presence of interactions. A first order perturbation to the fully nonlinear function using linear coefficients as approximation was used.

The response function in (12) is based on the optimization of the nonlinear function (11) in general to the same data set as before. It gives (12) as the best fit with the correlation coefficient of 0.9. Note that as stated before, there is no magic statistical method so it is necessary to try as many as possible and select the one that gives the best outcome (i.e. highest correlation with the data set). Here, obviously, the PCA and the optimization of the function (12) using multiple linear regression do not give a perfect agreement, however they do identify the $x_{12}$ and $x_1 x_{15}$ terms. PCA suggests $x_{13} x_{15}$ while the other method suggests $x_{10} x_{12}$ is an interactive term. If different statistical methods produce divergent results, then in the absence of empirical evidence against either result, both results should be kept.

In conclusion, it can be seen from the above example that it is possible to identify the active components using statistical tools and PCA. One can also create an activity model using multi-linear regression. Optimized drug response can be found with a given activity of the compounds. The minimum number of measurements required for a unique solution with N components is:

$$1 + N + N^2/2 \quad (15)$$

Hence the number of measurements can be reduced by subset selection.

To find an optimum composition of the compound, equations (13) and (14) were used in the general case. Specifically, for the simplest possible example where two ingredients have been isolated but their relative concentration has not been optimized yet, the following example was considered. Suppose the activity function depends on these two components x and y according to:

$$\text{Activity} = 0.3x + 0.4y + 0.7xy \quad (16)$$

Where the last term describes the synergistic action of the two ingredients. Since the entire mixture only contains components x and y, the condition: x+y=1 exists. The activity function was then transformed into:

$$\text{Activity} = 0.4 + 0.6x - 0.7x^2 \quad (17)$$

such that this is effectively a function of only one variable, namely x. Activity was minimized with respect to x to obtain:

$$\frac{d(\text{Activity})}{dt} = 0 \quad (18)$$

giving $$x = 0.43$$

Consequently the optimized formulation is: x=0.43 and y=0.57. This example is illustrated in FIG. 10.

The same approach can be applied to a combination of many ingredients but will require a multi-dimensional analysis.

In FIGS. 11A-G a three-dimensional illustration is given with several examples of dose dependence for two ingredients affecting the overall response and how the residuals emerge in each case.

APPROACH #3: Miscellaneous Approaches

One of the aspects of our method was to generate a subset of variables that dominate the data set and provide a subsequent least squares regression fitting to the data. This is a fairly common problem in statistical inference dealing with sparse data sets that involves finding solutions to under-determined, or ill-conditioned, linear systems of equations. A standard approach consists in minimizing an objective function which includes a quadratic (squared) error term combined with a sparseness-inducing regularization term. Numerous mathematical approaches have been developed in this area, for example the basis pursuit, the least absolute shrinkage and selection operator (LASSO), wavelet-based deconvolution, and compressed sensing are well studied methods in this area. Another novel approach is the so-called gradient projection (GP) algorithm for the bound-constrained quadratic programming (BCQP) formulation of this type of problem. Variants of this approach select the line search parameters in different ways, including techniques based on the Barzilai-Borwein method. These GP approaches have been shown to perform well in a wide range of applications, often being significantly faster than competing methods. A recent reviews of this and similar techniques dealing with the problem can be found in a recent article (Figueiredo et al., 2007).

EXAMPLE 4

Enhance Likelihood of Identifying the Right Bioactive Components

The approaches taken in example 3 in identifying unknowns that are of potential value could be improved by two methods described below:

a. Use of in silico simulation to predict pharmacokinetic profiles of components that have been identified in the past, for example, components of chuanxiong. There are a number of methods reported in the literature which can be used to achieve this goal (Norinder and Bergstrom, 2006; Dearden, 2007; Fagerholm, 2007a; Fagerholm, 2007b; Moda et al., 2007). This approach is particularly useful for the a priori estimation of potentially important candidates; particularly these candidates are present in minute quantities, for example, coumestrols and lignans in red clover and ferulic acid in chuanxiong. Using this approach, it will become apparent that these components are not important in these herbs although they are active. This information is valuable in the cluster analysis outlined in Example 3.

b. The measurement of tissue distribution of a product in vivo will permit the identification of components present in the biophase. For example, the measurement of bone, mammary gland, uterus/prostate and brain content after the administration of soy isoflavones reveals that only conjugates and their respective aglycones plus a few metabolites are present. This greatly reduces the number of components that are required for the estimation of pharmacokinetic and pharmacodynamic properties, hence, the accuracy of determination of the profile of ingredients that is required to be standardized.

EXAMPLE 5

Use In Vitro Techniques to Generate Kinetic Data in the Gastrointestinal Tract for the Pharmacokinetic/Pharmacodynamic Model Outlined in FIG. 1

A more detailed description of the model is presented in FIG. 12. The kinetics of decomposition, metabolism and absorption will be measured using: a. artificial gastric and intestinal juice; b. intestinal flora; c. intestinal microsomes; and d. Caco-2 or MDCK cell membrane or intestinal tissue.

Stability in Artificial Gastric and Intestinal Juice:

A mixture of components is incubated with artificial gastric and intestinal juice. A standard procedure for preparing the artificial gastric and intestinal juice is described in the United States Pharmacopoeia. The kinetics of degradation is a measure of the stability of individual components in the mixture. Using the approach similar to that described in Example 1, (with the modification that r is replaced by degradation rate constants in equations 4 and 5), the stability of individual components and potential interactions in terms of altering stability or decomposition by other components could be identified.

Metabolism by Intestinal Flora:

Standard procedures for studying metabolism of herbal mixtures by intestinal flora are well established (Hasegawa et al., 1996; Hasegawa and Uchiyama, 1998; Hasegawa et al., 2000; Hasegawa, 2004). Ginsenosides are known active components of various types of ginseng including *Panax ginseng*, rotoginseng, American ginseng, etc. Interestingly, these components have little pharmacological activity. The aglycones produced by step-wise removal of the glycosides by intestinal bacterial enzymes are active. These aglycones have a much better bioavailability than the corresponding ginsenosides. The rate of metabolism of individual components and potential interactions among them by intestinal flora will be quantified using the approach described in Example 1.

Permeability:

Caco-2, MDCK cells, rat intestine and PAMPA are commonly employed for the measurement of intestinal permeability. Caco-2 cell layers are a common model employed for the estimation of the permeability of potential leads, although it is not a good model for predicting chemicals that are absorbed via paracellular transport. MDCK cells cultured with an in-house proprietary process provide a much better estimation. However, cell cultures are not often suitable for studying permeability of dosage forms, natural extracts or formulations. Experience tells us that the integrity of these preparations is not always guaranteed. PAMPA has not been used for the evaluation of natural substance absorption. It is not clear whether this model will be applicable for natural product research. Rat intestinal tissues have been used extensively to study absorption of synthetic and natural substances (Ruan et al., 2006). In general, the bioavailability estimated using this model corresponds well with that of rats and humans (Chiou, 1995; Chiou and Barve, 1998; Chiou et al., 2000). Using these methods and the approach described in example 1, the permeability of individual components and their effects on the permeability of other components in a mixture could be measured.

Intestinal Microsomes:

Components that are permeable are selected for incubation with intestinal microsomes. These components could be decomposition products in the gastrointestinal lumen, metabolites formed from intestinal flora, or intestinal enzymes. The reason for this is the fact that components that are not absorbable have no access to these enzymes (FIG. 13).

The rate of metabolism of individual components in a mixture can be estimated using the approach outlined in Example 1. Interacting components can also be identified. The rate of metabolism, enzyme induction or inhibition could be measured and scaled using a pharmacokinetic model similar to that of FIG. 1.

Data generated from this series of studies will provide all the parameters for describing the stability, metabolism and rate of absorption in the gut after oral administration of a mixture (parameters for FIGS. 1, 12 and 13). Potential interactions can also be identified at the absorption and metabolism level.

EXAMPLE 6

Generate Hepatic Metabolism Data for the Liver Compartment in the Pharmacokinetic Model It has been shown in recent literature that metabolic data generated using cryopreserved human hepatocytes provide better prediction of hepatic clearance in human than human liver microsomes (Lam and Benet, 2004; Hallifax et al., 2005). The advantage of using hepatocytes is that membrane uptakes of components into the cell are accounted for (FIG. 14).

Only components and their metabolites which are absorbed from the intestine are studied. These substances will be concentrated from intestinal microsomes. The absorbable components are collected from the basal compartment of the apparatus after a permeability study.

The approach described in Example 1 may be used to evaluate the rate of metabolism of a component in a mixture. Instead of using the concentration-effect relationship, the rate of metabolism is used in the place of effect. Data collected from these studies will also permit component-component and component-metabolite interactions.

Hepatic clearance can be predicted using published methods (Lau et al., 2002; Hallifax et al., 2005). These data will be incorporated into the pharmacokinetic/pharmacodynamic model for profile prediction.

EXAMPLE 7

Estimation of Plasma Protein Binding and Volume of Distribution

All of the absorbable components and metabolites are expected to be present in the circulatory system. In theory, the number of components generated from a mixture after oral administration will be at least an order of magnitude higher than that of the number of absorbable species. However, many of these components are present in extremely minute quantities and it would be difficult to measure them accurately. These minute components are likely insignificant contributors to the pharmacokinetics and pharmacodynamics of the mixture. However, if they do have significant contributions, mathematical analysis will be able to detect them. Unless there are reasons to follow them, they will be treated as inactives.

In this example, the plasma protein binding of a component in a mixture is measured using human plasma. Methods such as equilibrium dialysis are commonly employed to measure the binding of chemicals in plasma. A schematic of distribution of a component in blood is shown in FIG. 15. Potential interaction between components will be evaluated using the approach outlined in Example 1. The only difference is that the binding equation is used to describe the potential interaction.

Free fraction of components in the plasma will be obtained from these types of in vitro studies. The data can be used in two ways: 1. the free fraction is inserted into the pharmacokinetic/pharmacodynamic model in the blood compartment; and 2. Volume of distribution can be predicted using plasma protein binding and log P values of the components (Lobell and Sivarajah, 2003). Again, this parameter can be inserted into the pharmacokinetic/pharmacodynamic model.

EXAMPLE 8

Prediction of the Rate of Renal Excretion of Components and their Metabolites

The rate of renal excretion of components and their metabolites can be predicted using a published method (Brightman et al., 2006a). Again, potential interactions among components can be predicted using the approach described in Example 1. The only difference is the concentration-effect relationship is replaced with the excretion rate constants.

EXAMPLE 9

Use of a Physiologically Based Pharmacokinetic and Pharmacodynamic Model to Describe the Concentration and Effect Time Course of Components in a Mixture after Oral Administration This physiologically based pharmacokinetic and pharmacodynamic model is graphically represented in FIGS. 1, and 12-15. The parameters for this model can be generated by the studies outlined in examples 5 to 8. Potential pharmacokinetic interactions can be predicted using the data. If appropriate pharmacological model(s) is chosen for measuring such multi-component activities as those outlined in example 1, the composite response by these components can be described. In this example, the theoretical aspects of the pharmacokinetic/pharmacodynamic model (FIG. 1) are described.

The Segmental Dissolution, Transit and Absorption (SDTA) model accounts for the dissolution and transit flow in the stomach, duodenum, jejunum, and ileum and the absorption in the duodenum, jejunum, and ileum. The gastrointestinal tract is divided into three compartments: Stomach, small intestine, and colon. The human small intestine can be described by seven sub-compartments, where a drug transfers from one sub-compartment to the next one in a first-order fashion (Yu et al, 1996). The SDTA model includes the following two assumptions: First, that absorption from the stomach is insignificant compared with that from the small intestine; and the second is that a drug moving through the small intestine can be considered as a process of flowing through a series of segments, each described by a single sub-compartment with linear transfer kinetics from one to next, and all compartments may have different volumes and flow rates, but the same residence times.

In the equations that follow, the subscript i refers to the particle size groups that make up the overall particle size-mass distribution. Within any particle size group, all particles are the same size and their size will not change as dissolution or precipitation occurs. Instead, dissolution and precipitation occurs by changing the number of particles. Therefore, for a non-degradable drug dosed in an immediate release dosage form, the dissolution, absorption, and transit in the gastrointestinal tract can be depicted as follows:

Stomach $$\frac{dM_{si}^s}{dt} = -K_s M_{si}^s - K_{d_s} M_{si}^s \tag{19}$$

$$\frac{dM_{di}^s}{dt} = -K_s M_{di}^s + K_{d_s} M_{si}^s \tag{20}$$

Small Intestine $$\frac{dM_{si}^n}{dt} = K_t M_{si}^{n-1} - K_t M_{si}^n + K_{d_n} M_{si}^n \quad n = 1, 2, \ldots 7 \tag{21}$$

$$\frac{dM_{di}^n}{dt} = K_t M_{di}^{n-1} - K_t M_{di}^n + K_{d_n} M_{si}^n - K_{a_n} M_{di}^n \quad n = 1, 2, \ldots 7 \tag{22}$$

Colon $$\frac{dM_{si}^c}{dt} = K_t M_{si}^7 - K_c M_{si}^c + K_{d_n} M_{si}^c \tag{23}$$

$$\frac{dM_{di}^c}{dt} = K_t M_{di}^7 - K_c M_{di}^c + K_{d_c} M_{si}^c - K_{a_c} M_{di}^c \tag{24}$$

where t is time, $M_{si}^s M_{si}^n M_{si}^c$ are the amounts of solid drug in stomach, nth segment of small intestine, and colon respectively. $K_s$, $K_t$, $K_c$, and $K_a$ are the rate constants of gastric emptying, small intestine transit, colon transit, and intrinsic absorption, respectively. In Eq. (3,4), when n=1, the term $K_rM^0$ is replaced by $K_sM^s$.

The overall rate of drug absorption can be calculated by:

$$\frac{dM_a}{dt} = \frac{2P_{eff}}{R}M_L + \frac{2P_{eff_{colon}}}{R_{colon}}M_L^C \quad (25)$$

where $M_a$ is amount of drug absorbed at time t, Peff is the effective permeability of intestinal membrane to the drug, R is radius of small intestine, $M_L = \Sigma M_L^n$, n=1, 2 ... 7, $P_{eff(colon)}$ is effective permeability of the colon membrane to the drug and $R_{colon}$ is the colon radius. The fraction of dose absorbed can then be calculated by $$F_a = M_{a_{t\to\infty}}/M_0 \quad (26)$$

$$= \frac{1}{M_0}\int_0^\infty \left[\frac{2P_{eff}}{R}M_L + \frac{2P_{eff_{colon}}}{R_{colon}}M_L^C\right]dt$$

Equations 25 and 26 can be used to estimate the fraction dose absorbed and the rate of drug absorption which in turn can be related to conventional compartmental pharmacokinetic models.

The absorption can be limited by dissolution rate and permeation rate, where permeation rate refers to the flux of drug across the intestinal membrane. The supply rate of dissolution and the uptake rate of permeation determine the concentration of drug in GI tract. However, the concentration in GI tract is also limited by the solubility of drug. When the supply rate is far more than the uptake rate, the drug concentration in the gastrointestinal fluid approaches its solubility limit. Mathematically, the dissolution rate is expressed by:

$$Rate_{dissolution} = \frac{3DM_s}{dhr}\left(C_s - \frac{M_L}{V}\right) \quad (27)$$

Where D is diffusion coefficient, h is diffusion layer thickness, d is density of solid drug, Cs is the solubility, and V is the volume. Thus, poor dissolution can be caused either by particle size (r) or solubility.

This model simulates the transport, dissolution, and absorption of compounds through the human intestine and computes flux into the portal vein, the total fraction absorbed, and (if body pharmacokinetic parameters are available) the concentration-time curve in the plasma. Intestinal transport is modelled as serial compartments, which has been shown to reproduce the small intestinal transit time distribution with sufficient accuracy given the in vivo variability (Lartigue et al., 1991). Dissolution dynamics are either interpolated from an in vitro dissolution curve or are simulate d using the Noyes-Whitney equation, accounting for the particle size, the solubility as adjusted for pH using the Henderson-Hasselbach equation, and local saturation. Local absorption rate is proportional to dissolved drug concentration; i.e. the apical membrane is assumed to be the rate limiting barrier to absorption, with absorbed drug sufficiently rapidly mixed with the body compartment as to maintain sink conditions, and transport to be either passive or in a linear regime. The absorption rate coefficient is determined by in vitro experiment using Caco-2 or MDCK cells or intestinal tissue, anatomical properties of the small intestine, and a correction factor determined by a single parameter fit to a diverse set of drugs. The primary purpose of the correction factor is to account for the increased surface area available for absorption in vivo as compared with the flat in vitro monolayers, but there is also a phenomenological component to the correction, as evidenced by substantial difference between the correction required for MDCK and Caco-2 monolayers. Absorbed flux enters the central body compartment for distribution and clearance using a physiological model as described in FIG. 1 (Brightman et al., 2006a; Brightman et al., 2006b).

The primary purpose of the virtual gut model is to transform local information about permeability garnered from in vitro experiments into a prediction of the overall level and time course of drug absorption. The gut is essentially a somewhat flexible tube with semipermeable walls. Food and water pass through the gut while nutrients and fluids are absorbed into the portal system.

The transit rate in the gut is slow, with an average small intestine transit time around three hours, and around 24 hours for the entire GI tract. Thus, fluid motion in the gut lumen may be assumed to be highly laminar and poorly mixed in the radial direction. The properties of a cylindrical laminar flow model with wall absorption have been studied in the context of heat exchangers and have also been applied to intestinal absorption (Amidon et al 1980 and Elliot, 1979). The principal problem with this approach is that the precise details of fluid flow and drug transport are unlikely to be reflective of the physiological situation, given the variations in tube shape, the peristaltic nature of fluid transport, the motions of the individual, and so on. Much simpler models, such as complete radial mixing coupled with longitudinal dispersion, are just as reflective of gut transit characteristics, and are easier to work with. The most popular model, the compartmental absorption and transit model, in fact includes dispersion only implicitly through the use of a small number of longitudinal compartments.

A one-dimensional advection-diffusion model for transport in the gut would be as follows:

$$\frac{\partial C}{\partial t} = D\frac{\partial^2 C}{\partial x^2} - v\frac{\partial C}{\partial x} + F(C) \quad (28)$$

Where x is the location along the gut, C(x,t) is the substance concentration, assumed uniform across the gut cross section, at a particular place and time, v is the velocity of transport through the gut, D is the dispersion constant, and F is a function capturing non-transit characteristics such as absorption, metabolism, etc.

Discretizing the advection term for use in a finite difference model, showed $$\frac{\partial C}{\partial x} \approx \frac{C(x+\delta) - C(x)}{\delta} = \frac{\partial C}{\partial x} + \frac{1}{2}\delta\frac{\partial^2 C}{\partial x^2} + O(\delta^2) \quad (29)$$

Which shows that there is a diffusive component of the discretized equation, called numerical diffusion, which is usually seen as an annoyance. The compartmental absorption and transit model takes advantage of this by using it to model the diffusive nature of the underlying system, and adjusting the discretization size δ appropriately to capture the dispersion observed in vivo.

The function F(C), included above, is selected to capture absorption, metabolism, and other characteristics. The simplest and most important factor, passive absorption, is given by $$F(C) = -K_a S \quad (30)$$

using $$K_a = \frac{2\lambda P_{eff}}{R} \quad (31)$$

Where $P_{eff}$ is the effective permeability, R is the gut radius, and $\lambda$ is a surface-to-volume correction factor selected to allow for the surface area differences between the foliations of the actual gut wall and the relatively flat surface of a cell monolayer.

The drug flux into the portal vein J and the fraction absorbed $F_a$ are computed as $$J(t) = \sum_{x=d, j_{1-4}, i} K_x C_x(t) \quad (32)$$

$$F_a = \int_0^\infty J(t) dt \quad (33)$$

Active transport can be modeled by replacing $P_{eff}$ with a concentration dependent permeability $$P_{eff}(C) = \frac{P_{max}}{K_m + C} \quad (34)$$

Where the maximum rate of permeation $P_{max}$ and the effective binding constant $K_m$ may be estimated from in vitro experiments and are potentially region dependent.

Metabolism is modeled by tracking concentrations of parent and metabolite separately, and including a term in the local model that converts parent to metabolite. Although this is possible to extend to any number of metabolites, the current model is illustrated using a single metabolite. The transformation terms are of the form:

$$\frac{d}{dt}\begin{bmatrix} C_p \\ C_m \end{bmatrix} = \begin{bmatrix} -\frac{V_{max}}{K_m + C_p} & 0 \\ \frac{V_{max}}{K_m + C_p} & 0 \end{bmatrix} \begin{bmatrix} C_p \\ C_m \end{bmatrix} \quad (35)$$

Where $V_{max}$ and $K_m$ may be region dependent and each component (parent and metabolite) following similar transport and absorption dynamics.

Dissolution is modeled similarly by considering the transformation from the solid phase to the dissolved phase. Dissolution is limited by diffusion of the dissolved species away from the solid particle. For the case of uniform spherical particles dissolving into an infinite medium, the diffusion equation can be solved in the form of the Hixson-Crowell Cube Root law, $$M_0^{1/3} - M^{1/3} = \kappa t \quad (36)$$

Where $\kappa$ is the cube root dissolution constant. Since the flux input is based on the quantity of original undissolved material, a term for input from dissolving solids of the form was $$\frac{d}{dt} C_d = \frac{3C_s}{T_d}(1 - t/T_d)^2 \quad (37)$$

Where $C_s$, the concentration of undissolved particles, is altered only through transport and $T_d$, the dissolution time is defined as $$T_d = \frac{d\rho}{2C_s D/h} \quad (38)$$

Where d is the particle diameter, $\rho$ is the density of the particles, $C_s$ is the solubility, D is the diffusion constant, and h is the effective depth of the unstirred layer. This input is set to zero when $t > T_d$.

The number of compartments, the total transit time, the luminal surface-to-volume ratio 2/R and the gastric emptying rate are all relatively independent of drug but depend on the species under consideration (Table 6).

TABLE 6

Species-Specific Parameters

| | Human | Rat | Dog |
|---|---|---|---|
| Number of compartments | 7[1] | 7 | 7 |
| Total small intestine transit time | 199 min[1] | 180 min | 83 min[2] |
| Effective gut radius | 1.75 cm[1] | 0.2 cm | 0.75 cm |
| Gastric emptying time | 15 min | 15 min | 15 min |

[1]Yu et al, 1996,
[2]Iwanaga et al, 1998

The number of compartments is an indication of the dispersion, and takes into account the degree of longitudinal mixing during the transport of material along the small intestine. The transit time is the average amount of time material spends in the small intestine. The gastric emptying time is the amount of time required for half of the gastric contents to enter the duodenum through the pyloric valve. While gastric emptying is quite variable, the dynamics of gastric emptying do not have a large effect on fraction absorbed, due to the principle of superposition. Gastric emptying will however affect the detailed dynamics of the drugs, altering pharmacokinetic parameters such as $C_{max}$ and $T_{max}$.

While computational systems can in general only be validated through careful design and implementation, there are several specific tests applicable to the current system that act to ensure both that the numerical integrations have a sufficient degree of accuracy and that certain kinds of gross errors are absent.

Every molecule of drug put into a system must go somewhere: it must be excreted, distributed to some part of the body, or transformed into some metabolite. Mass balance is often used in experimental pharmacokinetics, and it has value here as well.

For the special case of drugs which exhibit purely passive diffusion, high solubility, and no regional permeability, the system of equations may be solved exactly for $F_a$, giving $$F_a = 1 - (1 + K_d/K_t)^{-N} \tag{39}$$

Where $K_t$ is the transport constant between each compartment and N is the number of compartments.

Within the pharmacokinetic model, the body is represented with several compartments. Each has a volume and the parameters are listed on Table 7.

Of particular interest is the "Tissue Compartment" which represents body tissues not otherwise accounted for in the model. The compound concentrations in this compartment determine the intensity of physiologic effect. This is shown by the striped connection to the adjacent "Response" box.

The movement of materials between compartments is shown with arrows. Initial doses enter the stomach, while the colon, liver, and kidneys are sites of potential elimination from the system. The movement of the compounds between compartments is proportional to the volume of fluid flow between the compartments and the concentration of the compound in the originating compartment, and inversely proportional to the volume of the original compartment.

The model assumes a "mass-balance" approach, with equality between the amounts of material that leave one compartment and the amounts that enter into another.

Given an initial distribution of the compounds in the various compartments, the model is integrated forwards in time, using a 4th order Runge-Kutta algorithm, with variable time-steps.

The tissue compartment is sized so that the sum of the compartments, excluding the GI-tract interiors, is equal to the volume of distribution for a 70 kg man.

Using the 15-component mixture described in example 2, a list of pharmacokinetic parameters is generated and is detailed on Table 7. The parameters that are inherent to the pharmacokinetic model are listed on Tables 8 and 9. These data are extracted from published data (Bernareggi and Rowland, 1991; Davies and Morris, 1993; Brown et al., 1997).

The above examples outline the integrated in silico and in vitro methods which are used for identifying active and interacting species from a mixture, similar to those of a natural substance. Using the physiologically based pharmacokinetic and pharmacodynamic model, the concentration time course of each of the 15 components is estimated (FIG. 16). Similarly, the time course for the composite response is also calculated (FIG. 17). Once data such as that of FIG. 17 is generated, an optimal dosage to produce a desired response can be reconstructed. This dosage consists of an ingredient profile, which is essential for the development a new product and/or dosage form.

TABLE 7

Pharmacokinetic Parameters of The 15 Compounds

| Compound Number | Intestinal Permeability, min$^{-1}$ | Intrinsic Hepatic Clearance, min$^{-1}$ | Hepatic Clearance, L/min | Volume of Distribution L/kg |
|---|---|---|---|---|
| 1 | 0.17 | 632 | 0.59 | 0.53 |
| 2 | 0.86 | 6633 | 1.31 | 1.16 |
| 3 | 4.02 | 1104 | 0.79 | 0.36 |
| 4 | 4.43 | 2011 | 1.01 | 0.66 |
| 5 | 1.89 | 183 | 0.24 | 0.52 |
| 6 | 0.52 | 810 | 1.34 | 1.64 |
| 7 | 2.40 | 555 | 0.54 | 0.95 |
| 8 | 6.88 | 8929 | 1.35 | 0.58 |

TABLE 7-continued

Pharmacokinetic Parameters of The 15 Compounds

| Compound Number | Intestinal Permeability, min$^{-1}$ | Intrinsic Hepatic Clearance, min$^{-1}$ | Hepatic Clearance, L/min | Volume of Distribution L/kg |
|---|---|---|---|---|
| 9 | 0.14 | 15406 | 1.41 | 0.90 |
| 10 | 0.19 | 1428 | 0.89 | 1.57 |
| 11 | 0.12 | 792 | 1.33 | 2.28 |
| 12 | 0.20 | 294 | 0.35 | 0.35 |
| 13 | 0.80 | 915 | 0.72 | 0.79 |
| 14 | 2.99 | 223 | 0.28 | 0.80 |
| 15 | 0.38 | 443 | 0.46 | 0.95 |

TABLE 8

Blood Flow Rate To And From Various Organs

| Flow | Clearance, mL/min |
|---|---|
| along GI tract | 2 |
| blood → intestine/colon | 235 |
| intestine/colon → liver | 235 |
| blood → liver | 239 |
| liver → blood | 1180 |
| blood ↔ tissue | 3110 |

TABLE 9

Physiological Volumes of Various Organs

| Compartment | Volume, L |
|---|---|
| interiors of stomach/intestine/colon | 0.155 |
| intestinal segments | 0.212 |
| colon | 0.371 |
| kidneys | 0.280 |
| liver | 1.69 |
| blood | 5.20 |

EXAMPLE 10

An Integrative Example Showing the Contribution of "Drug-Like" Properties to the Effective Ingredients The objective of this example is to provide a means of estimating the active ingredients in a simulated mixture of 50 components. In Table 10, the in vitro response for each of the fifty components in the system is shown. Additionally two pairs of components (3, 23) and (20, 50) have synergistic interactions with activities of 0.800 and 1.00 respectively. A ±5% was randomly added to the data and the overall response of each mixture show a Michaelis-Menton style limit to the total interactions. FIG. 18 shows typical of overall response data for mixtures with components randomly distributed between 0 and 1 unit in each mixture.

Using randomly generated pharmacokinetic parameters for these ingredients, this example also illustrates the importance of the drug-like properties in the determination of therapeutically relevant ingredient profile.

TABLE 10

In vitro Response For Components In The System

| No. | Activity |
|---|---|
| 1 | $3.34 \times 10^{-1}$ |
| 2 | $9.11 \times 10^{-3}$ |

TABLE 10-continued

In vitro Response For Components In The System

| No. | Activity |
|---|---|
| 3 | $6.71 \times 10^{-1}$ |
| 4 | $6.40 \times 10^{-3}$ |
| 5 | $6.15 \times 10^{-1}$ |
| 6 | $5.48 \times 10^{-3}$ |
| 7 | $6.62 \times 10^{-3}$ |
| 8 | $2.08 \times 10^{-2}$ |
| 9 | $1.41 \times 10^{-2}$ |
| 10 | $4.53 \times 10^{-3}$ |
| 11 | $1.36 \times 10^{-2}$ |
| 12 | $6.19 \times 10^{-3}$ |
| 13 | $2.88 \times 10^{-2}$ |
| 14 | $2.57 \times 10^{-1}$ |
| 15 | $5.81 \times 10^{-3}$ |
| 16 | $8.75 \times 10^{-1}$ |
| 17 | $1.90 \times 10^{-2}$ |
| 18 | $2.09 \times 10^{-2}$ |
| 19 | $7.43 \times 10^{-3}$ |
| 20 | $5.81 \times 10^{-1}$ |
| 21 | $9.68 \times 10^{-3}$ |
| 22 | $9.43 \times 10^{-3}$ |
| 23 | $6.84 \times 10^{-1}$ |
| 24 | $4.63 \times 10^{-3}$ |
| 25 | $6.14 \times 10^{-3}$ |
| 26 | $3.48 \times 10^{-3}$ |
| 27 | $3.85 \times 10^{-3}$ |
| 28 | $7.18 \times 10^{-3}$ |
| 29 | $5.03 \times 10^{-3}$ |
| 30 | $3.71 \times 10^{-1}$ |
| 31 | $1.05 \times 10^{-2}$ |
| 32 | $2.51 \times 10^{-1}$ |
| 33 | $4.55 \times 10^{-1}$ |
| 34 | $5.88 \times 10^{-3}$ |
| 35 | $2.05 \times 10^{-2}$ |
| 36 | $1.34 \times 10^{-2}$ |
| 37 | $2.58 \times 10^{-2}$ |
| 38 | $6.80 \times 10^{-3}$ |
| 39 | $1.43 \times 10^{-2}$ |
| 40 | $2.25 \times 10^{-1}$ |
| 41 | $7.58 \times 10^{-3}$ |
| 42 | $7.37 \times 10^{-3}$ |
| 43 | $9.08 \times 10^{-3}$ |
| 44 | $1.03 \times 10^{-2}$ |
| 45 | $5.56 \times 10^{-3}$ |
| 46 | $6.03 \times 10^{-3}$ |
| 47 | $1.61 \times 10^{-2}$ |
| 48 | $1.18 \times 10^{-2}$ |
| 49 | $1.83 \times 10^{-2}$ |
| 50 | $10.0 \times 10^{-1}$ |

With 150 mixtures and overall responses from the 1.0 dose point (FIG. 18) and assuming a linear response from each of the 50 components estimated responses (x with ±1 standard deviation error bars). These generally compare well with the actual responses (◯), but some large differences are present (FIG. 19).

Using the approach described in Example 3, the correlations between the residual and each of the multiplicative pairs terms is plotted. Higher correlations are darker, particularly striking is the (20,50) pair, one of the interacting pairs in the input activities (FIG. 20).

Adding four pair terms as pseudo-components 51 to 54 yields a new and improved estimate. Particularly noticeable are that 51 and 54 are active, while 52 and 53 are not. Generally component may be classified as active or inactive (FIG. 21).

Repeating the same systems, but now using data from three dose points (1.0, 0.3, and 0.1) gives a tighter and more accurate fit in the first estimate (FIG. 22).

The residual correlation plot looks very similar to the single dose point case and is omitted for brevity. Using the same four pseudo-components gives a second estimate with a better fit than in the single dose point case. Similar observations are observed with the four pseudo-components. Components 51 and 54 are shown to interact and 52 and 53 are found to be inactive (FIG. 23). This example clearly shows that activity of individual components and their interactions can be accurately predicted using the approach described in this invention.

In the second part of this study, a two compartment pharmacokinetic system with first order kinetics was used for the simulation. The first compartment is intestinal with a volume of 0.4 for all fifty components. From the intestinal compartment there is direct elimination from the first compartment and absorption into the second compartment with differing clearances for each component. The second compartment represents the body, for which each component has a different volume and clearance from the system. All of these are listed in Table 11, along with the half-lives and area under the time-quantity curves in the body compartment. The volumes and rate constants were generated with uniformly distributed pseudo-random values over appropriate intervals and all other numbers were calculated from these.

TABLE 11

| | Intestinal Clearances | | Body Compartment | | | |
|---|---|---|---|---|---|---|
| | Elimination | Absorption | Volume | Clearance | Half-life | AUC |
| 1 | $8.3 \times 10^{-2}$ | $4.8 \times 10^{-4}$ | 137 | 8.10 | 11.7 | 0.39 |
| 2 | $7.6 \times 10^{-2}$ | $1.3 \times 10^{-3}$ | 97 | 5.71 | 11.7 | 1.15 |
| 3 | $8.2 \times 10^{-2}$ | $6.3 \times 10^{-4}$ | 130 | 4.79 | 18.9 | 0.82 |
| 4 | $7.7 \times 10^{-2}$ | $5.1 \times 10^{-4}$ | 134 | 6.33 | 14.6 | 0.55 |
| 5 | $7.6 \times 10^{-2}$ | $4.9 \times 10^{-4}$ | 104 | 2.60 | 27.7 | 1.01 |
| 6 | $7.6 \times 10^{-2}$ | $3.6 \times 10^{-4}$ | 110 | 5.56 | 13.8 | 0.37 |
| 7 | $7.5 \times 10^{-2}$ | $2.6 \times 10^{-4}$ | 149 | 13.84 | 7.4 | 0.15 |
| 8 | $8.6 \times 10^{-2}$ | $3.8 \times 10^{-3}$ | 132 | 8.69 | 10.5 | 2.54 |
| 9 | $8.4 \times 10^{-2}$ | $1.9 \times 10^{-3}$ | 141 | 10.63 | 9.2 | 1.19 |
| 10 | $8.4 \times 10^{-2}$ | $1.3 \times 10^{-3}$ | 84 | 0.52 | 112.2 | 10.06 |
| 11 | $8.3 \times 10^{-2}$ | $7.8 \times 10^{-4}$ | 77 | 2.39 | 22.2 | 1.19 |
| 12 | $7.4 \times 10^{-2}$ | $3.3 \times 10^{-3}$ | 87 | 6.10 | 9.9 | 2.45 |
| 13 | $7.3 \times 10^{-2}$ | $4.0 \times 10^{-4}$ | 118 | 2.84 | 28.8 | 0.90 |
| 14 | $7.9 \times 10^{-2}$ | $2.2 \times 10^{-4}$ | 59 | 0.67 | 61.3 | 1.00 |
| 15 | $8.3 \times 10^{-2}$ | $1.0 \times 10^{-3}$ | 110 | 7.13 | 10.7 | 0.75 |
| 16 | $8.7 \times 10^{-2}$ | $3.7 \times 10^{-4}$ | 120 | 8.26 | 10.0 | 0.24 |
| 17 | $7.4 \times 10^{-2}$ | $4.4 \times 10^{-4}$ | 83 | 7.01 | 8.2 | 0.28 |
| 18 | $7.8 \times 10^{-2}$ | $3.0 \times 10^{-4}$ | 45 | 3.44 | 9.1 | 0.20 |
| 19 | $8.1 \times 10^{-2}$ | $3.5 \times 10^{-3}$ | 88 | 5.09 | 11.9 | 2.84 |
| 20 | $8.6 \times 10^{-2}$ | $1.4 \times 10^{-3}$ | 131 | 7.72 | 11.8 | 1.07 |
| 21 | $7.5 \times 10^{-2}$ | $5.8 \times 10^{-4}$ | 70 | 1.80 | 27.1 | 1.20 |
| 22 | $7.9 \times 10^{-2}$ | $1.8 \times 10^{-3}$ | 85 | 1.86 | 31.8 | 4.08 |
| 23 | $8.4 \times 10^{-2}$ | $2.1 \times 10^{-4}$ | 115 | 7.28 | 11.0 | 0.16 |
| 24 | $8.4 \times 10^{-2}$ | $2.9 \times 10^{-4}$ | 124 | 2.87 | 30.0 | 0.60 |
| 25 | $8.1 \times 10^{-2}$ | $2.6 \times 10^{-4}$ | 91 | 7.06 | 8.9 | 0.16 |
| 26 | $7.8 \times 10^{-2}$ | $2.0 \times 10^{-3}$ | 125 | 9.49 | 9.1 | 1.32 |
| 27 | $8.8 \times 10^{-2}$ | $1.2 \times 10^{-3}$ | 67 | 3.15 | 14.8 | 1.20 |
| 28 | $8.3 \times 10^{-2}$ | $2.1 \times 10^{-4}$ | 130 | 1.96 | 45.8 | 0.67 |
| 29 | $8.0 \times 10^{-2}$ | $3.4 \times 10^{-4}$ | 61 | 2.43 | 17.4 | 0.42 |
| 30 | $8.0 \times 10^{-2}$ | $8.3 \times 10^{-4}$ | 133 | 6.54 | 14.1 | 0.84 |
| 31 | $8.7 \times 10^{-2}$ | $1.9 \times 10^{-3}$ | 62 | 1.35 | 32.0 | 3.89 |
| 32 | $7.5 \times 10^{-2}$ | $1.3 \times 10^{-3}$ | 37 | 0.77 | 33.0 | 3.33 |
| 33 | $7.5 \times 10^{-2}$ | $3.5 \times 10^{-3}$ | 122 | 2.41 | 35.2 | 8.99 |
| 34 | $7.9 \times 10^{-2}$ | $1.2 \times 10^{-3}$ | 134 | 9.91 | 9.4 | 0.80 |
| 35 | $8.4 \times 10^{-2}$ | $1.0 \times 10^{-3}$ | 56 | 1.75 | 22.3 | 1.51 |
| 36 | $8.4 \times 10^{-2}$ | $3.2 \times 10^{-4}$ | 78 | 5.67 | 9.5 | 0.21 |
| 37 | $8.8 \times 10^{-2}$ | $2.9 \times 10^{-4}$ | 129 | 5.69 | 15.7 | 0.30 |
| 38 | $7.5 \times 10^{-2}$ | $7.5 \times 10^{-4}$ | 133 | 6.75 | 13.6 | 0.77 |
| 39 | $7.9 \times 10^{-2}$ | $1.1 \times 10^{-3}$ | 43 | 1.15 | 25.9 | 2.13 |
| 40 | $7.5 \times 10^{-2}$ | $3.7 \times 10^{-3}$ | 129 | 10.22 | 8.8 | 2.35 |
| 41 | $7.6 \times 10^{-2}$ | $1.5 \times 10^{-3}$ | 118 | 8.79 | 9.3 | 1.04 |
| 42 | $8.3 \times 10^{-2}$ | $9.0 \times 10^{-4}$ | 73 | 2.40 | 21.0 | 1.30 |
| 43 | $7.9 \times 10^{-2}$ | $1.4 \times 10^{-3}$ | 38 | 0.32 | 82.1 | 8.51 |
| 44 | $7.7 \times 10^{-2}$ | $2.2 \times 10^{-4}$ | 114 | 3.16 | 24.9 | 0.42 |
| 45 | $7.5 \times 10^{-2}$ | $3.5 \times 10^{-4}$ | 82 | 4.79 | 11.9 | 0.32 |
| 46 | $8.1 \times 10^{-2}$ | $9.4 \times 10^{-4}$ | 41 | 0.23 | 124.3 | 8.23 |
| 47 | $7.6 \times 10^{-2}$ | $3.2 \times 10^{-4}$ | 93 | 2.83 | 22.8 | 0.55 |
| 48 | $8.4 \times 10^{-2}$ | $2.7 \times 10^{-4}$ | 59 | 3.95 | 10.3 | 0.19 |

TABLE 11-continued

| | Intestinal Clearances | | Body Compartment | | | |
|---|---|---|---|---|---|---|
| | Elimination | Absorption | Volume | Clearance | Half-life | AUC |
| 49 | $8.7 \times 10^{-2}$ | $3.8 \times 10^{-3}$ | 55 | 3.94 | 9.7 | 2.33 |
| 50 | $7.5 \times 10^{-2}$ | $8.4 \times 10^{-4}$ | 109 | 7.87 | 9.6 | 0.61 |

Using the pharmacokinetic data generated and an oral dose of 4 units for each of the 50 components (Table 11), a family of concentration-time curves is produced (FIG. 24).

Area Under Curve (AUC) for the concentration in body-time curves is an indicator of exposure, a net result of absorption and elimination. This data was given in Table 11. What is striking is that the range of AUC values can span as much 2 orders of magnitude (FIG. 25).

Taking the AUC values to be the exposure of the body to each compound, the same set of 150 mixtures can be scaled by the AUC of each compound. This corresponds to the difference between in vitro and in vivo experiments when compound activity is modulated by varied pharmacokinetic properties. The previous case is identical to one in which every component has the same properties. Note that what was a moderately active component in the previous system is now overwhelmingly the most active due to favorable pharmacokinetic properties. With fewer activities remaining in the system the estimates using the same three doses are quite good (FIG. 26).

The residuals, after incorporation the pharmacokinetic parameters, vary dramatically from the previous plots (FIG. 27 vs. FIG. 20). The darkness in each of these plots is scaled to the most correlated points in the plot, so the appearance of individual points can only be compared within each of these figures and not between them. The strongest correlations are actually weaker in this plot than in the previous one.

A second estimate with four pseudo-components added to it is not much different from the first estimate, and the pseudo-components have very small responses as the components composing them are not significantly present (FIG. 28).

A second pharmacokinetic system with a different set of pharmacokinetic parameters was considered, but chosen from the same ranges of values. The results from this system are shown in Table 12.

TABLE 12

| | Intestinal Clearances | | Body Compartment | | | |
|---|---|---|---|---|---|---|
| | Elimination | Absorption | Volume | Clearance | Half-life | AUC |
| 1 | $8.3 \times 10^{-2}$ | $2.0 \times 10^{-3}$ | 41 | 3.47 | 8.2 | 1.14 |
| 2 | $8.2 \times 10^{-2}$ | $2.2 \times 10^{-4}$ | 110 | 7.44 | 10.2 | 0.16 |
| 3 | $8.3 \times 10^{-2}$ | $6.1 \times 10^{-4}$ | 38 | 0.52 | 51.3 | 2.16 |
| 4 | $7.9 \times 10^{-2}$ | $8.8 \times 10^{-4}$ | 148 | 8.12 | 12.6 | 0.81 |
| 5 | $8.2 \times 10^{-2}$ | $2.9 \times 10^{-3}$ | 42 | 2.39 | 12.2 | 2.40 |
| 6 | $8.0 \times 10^{-2}$ | $1.9 \times 10^{-3}$ | 116 | 5.91 | 13.7 | 1.83 |
| 7 | $8.5 \times 10^{-2}$ | $8.2 \times 10^{-4}$ | 147 | 13.33 | 7.6 | 0.42 |
| 8 | $8.3 \times 10^{-2}$ | $3.0 \times 10^{-4}$ | 86 | 2.81 | 21.2 | 0.45 |
| 9 | $8.3 \times 10^{-2}$ | $2.5 \times 10^{-4}$ | 145 | 4.59 | 21.9 | 0.37 |
| 10 | $8.3 \times 10^{-2}$ | $2.8 \times 10^{-4}$ | 55 | 4.61 | 8.3 | 0.16 |
| 11 | $8.6 \times 10^{-2}$ | $1.8 \times 10^{-3}$ | 129 | 4.76 | 18.8 | 2.22 |
| 12 | $8.3 \times 10^{-2}$ | $2.2 \times 10^{-3}$ | 133 | 5.46 | 16.8 | 2.51 |
| 13 | $8.6 \times 10^{-2}$ | $2.6 \times 10^{-3}$ | 91 | 3.27 | 19.3 | 3.27 |
| 14 | $7.6 \times 10^{-2}$ | $2.6 \times 10^{-4}$ | 69 | 4.42 | 10.9 | 0.21 |
| 15 | $8.0 \times 10^{-2}$ | $3.4 \times 10^{-4}$ | 49 | 0.46 | 74.2 | 1.82 |
| 16 | $7.6 \times 10^{-2}$ | $7.3 \times 10^{-4}$ | 83 | 7.36 | 7.9 | 0.43 |
| 17 | $8.6 \times 10^{-2}$ | $2.4 \times 10^{-3}$ | 119 | 9.07 | 9.1 | 1.45 |
| 18 | $8.7 \times 10^{-2}$ | $3.5 \times 10^{-3}$ | 139 | 1.03 | 93.4 | 20.97 |

TABLE 12-continued

| | Intestinal Clearances | | Body Compartment | | | |
|---|---|---|---|---|---|---|
| | Elimination | Absorption | Volume | Clearance | Half-life | AUC |
| 19 | $8.3 \times 10^{-2}$ | $1.3 \times 10^{-3}$ | 137 | 4.75 | 20.0 | 1.77 |
| 20 | $8.2 \times 10^{-2}$ | $3.2 \times 10^{-3}$ | 118 | 2.37 | 34.5 | 7.41 |
| 21 | $7.2 \times 10^{-2}$ | $3.9 \times 10^{-3}$ | 131 | 10.39 | 8.7 | 2.60 |
| 22 | $8.3 \times 10^{-2}$ | $2.9 \times 10^{-4}$ | 146 | 2.09 | 48.5 | 0.98 |
| 23 | $7.7 \times 10^{-2}$ | $2.3 \times 10^{-3}$ | 93 | 1.68 | 38.3 | 6.50 |
| 24 | $8.1 \times 10^{-2}$ | $3.0 \times 10^{-4}$ | 109 | 3.68 | 20.5 | 0.44 |
| 25 | $8.5 \times 10^{-2}$ | $5.6 \times 10^{-4}$ | 128 | 6.77 | 13.1 | 0.50 |
| 26 | $7.7 \times 10^{-2}$ | $6.8 \times 10^{-4}$ | 96 | 7.54 | 8.8 | 0.45 |
| 27 | $7.6 \times 10^{-2}$ | $7.4 \times 10^{-4}$ | 61 | 5.35 | 7.9 | 0.44 |
| 28 | $8.7 \times 10^{-2}$ | $2.2 \times 10^{-3}$ | 44 | 1.66 | 18.5 | 2.64 |
| 29 | $8.1 \times 10^{-2}$ | $6.1 \times 10^{-4}$ | 77 | 2.15 | 24.9 | 1.09 |
| 30 | $8.0 \times 10^{-2}$ | $3.9 \times 10^{-4}$ | 101 | 2.74 | 25.5 | 0.72 |
| 31 | $8.2 \times 10^{-2}$ | $3.2 \times 10^{-4}$ | 52 | 3.56 | 10.2 | 0.23 |
| 32 | $7.8 \times 10^{-2}$ | $1.0 \times 10^{-3}$ | 71 | 5.28 | 9.4 | 0.71 |
| 33 | $8.6 \times 10^{-2}$ | $1.4 \times 10^{-3}$ | 108 | 7.74 | 9.7 | 0.91 |
| 34 | $7.7 \times 10^{-2}$ | $1.1 \times 10^{-3}$ | 47 | 2.92 | 11.1 | 0.94 |
| 35 | $7.8 \times 10^{-2}$ | $3.5 \times 10^{-4}$ | 141 | 9.72 | 10.1 | 0.26 |
| 36 | $7.9 \times 10^{-2}$ | $9.9 \times 10^{-4}$ | 106 | 5.86 | 12.6 | 0.90 |
| 37 | $7.2 \times 10^{-2}$ | $1.5 \times 10^{-3}$ | 120 | 6.59 | 12.7 | 1.49 |
| 38 | $8.0 \times 10^{-2}$ | $5.1 \times 10^{-4}$ | 80 | 5.37 | 10.3 | 0.37 |
| 39 | $8.7 \times 10^{-2}$ | $3.4 \times 10^{-4}$ | 37 | 3.12 | 8.1 | 0.18 |
| 40 | $7.9 \times 10^{-2}$ | $4.8 \times 10^{-4}$ | 70 | 6.25 | 7.7 | 0.27 |
| 41 | $8.5 \times 10^{-2}$ | $2.0 \times 10^{-3}$ | 76 | 5.11 | 10.3 | 1.37 |
| 42 | $8.2 \times 10^{-2}$ | $2.3 \times 10^{-3}$ | 107 | 2.65 | 28.0 | 4.49 |
| 43 | $7.4 \times 10^{-2}$ | $2.5 \times 10^{-4}$ | 50 | 1.83 | 18.9 | 0.38 |
| 44 | $7.7 \times 10^{-2}$ | $2.7 \times 10^{-3}$ | 149 | 9.33 | 11.1 | 2.14 |
| 45 | $8.4 \times 10^{-2}$ | $3.4 \times 10^{-3}$ | 47 | 1.08 | 30.2 | 6.86 |
| 46 | $7.9 \times 10^{-2}$ | $7.9 \times 10^{-4}$ | 67 | 5.74 | 8.1 | 0.46 |
| 47 | $8.0 \times 10^{-2}$ | $3.5 \times 10^{-4}$ | 54 | 3.91 | 9.6 | 0.24 |
| 48 | $7.4 \times 10^{-2}$ | $3.1 \times 10^{-4}$ | 87 | 2.36 | 25.6 | 0.63 |
| 49 | $8.3 \times 10^{-2}$ | $4.5 \times 10^{-4}$ | 88 | 4.86 | 12.5 | 0.39 |
| 50 | $7.6 \times 10^{-2}$ | $2.0 \times 10^{-4}$ | 115 | 6.91 | 11.5 | 0.18 |

Figure 32:
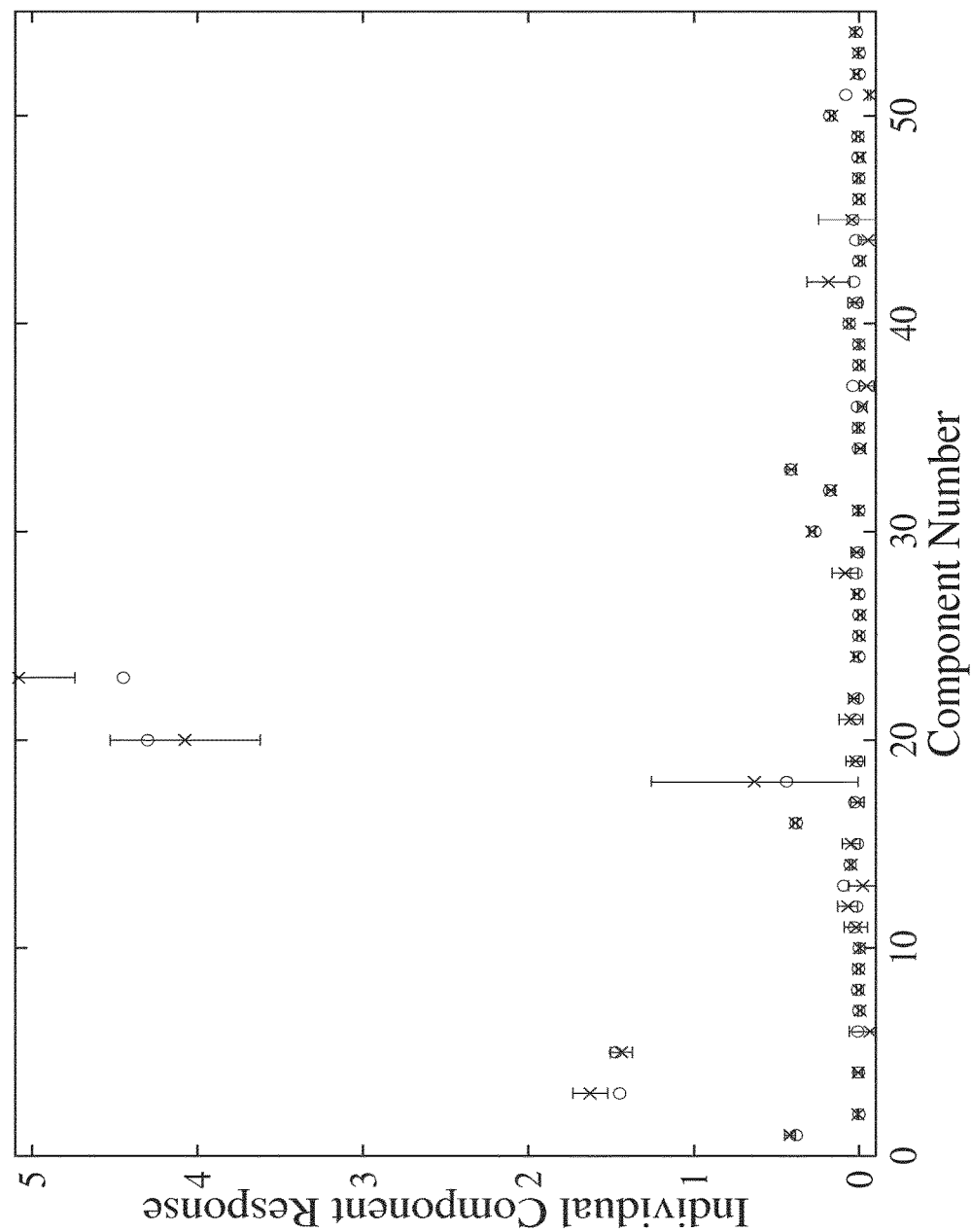

The second set of pharmacokinetic parameters gives concentration-time curves as shown on FIG. 29. The AUCs corresponding to the concentrations in the previous plot are shown in FIG. 30. The first estimate now reveals two important components, and two moderate ones (FIG. 31). Again, adding four pseudo-components has little effect on the system as the synergistic terms are largely suppressed due to the insignificant overlapping exposure of the interacting components (FIG. 32).

In these three examples, the response due to each component and pseudo-component is recovered from knowledge of the mixture compositions, the dose-overall response curve and a set of mixture-dose-overall response data. While these values are known beforehand in these simulations, the generation of estimates from the other data, suggests that reasonable estimates of these values could be obtained from experimental data for which activity estimates are not available. The strong differences between the three cases serve to emphasize the differences between in vivo and in vitro activities.

These examples also illustrate an important aspect of potential interaction. In vitro interaction does not always imply that there will be in vivo interaction. In this example, components 51 and 54 are interactive pairs in vitro, but interactions do not occur in vivo. It is therefore important to take pharmacokinetic differences into account when potential interactions are discovered in vitro. If the concentration profile overlap between the interacting species is insignificant, meaning if the pharmacokinetic characteristics of these potential interacting components are very different, the probability of interaction is likely to be minimal.

EXAMPLE 11

Applications of this Invention

The objective of this example is to illustrate some of the uses of this invention. It is common that ingredients may have multiple activities involving a number of biochemical processes. Depending on the conditions, a number of activity testing methods can be employed before the optimal composite response is decided. On the other hand, this invention can be used for estimating efficacy and toxicity when in vitro models are available. Both active and toxic components can be identified. With this information, an optimal ingredient profile can be designed.

After the optimal ingredient profile is obtained, the desired quantities of these ingredients can be obtained using one or a combination of the following ways: a. blend appropriate batches of raw materials; b. develop a customized method to extract the ingredients of interest; c. design growing conditions to yield the desired ingredients; d. develop a set of growing conditions under controlled environments such as that of a green house; e. genetically modify a species to produce the desired ingredients; and f. purify substances of interest and mix them according to the ingredient list.

For product design, a formulation can be prepared to deliver these substances in an optimal fashion such that optimal response is achieved.

Products design using this approach will have all the active ingredients identified; their interacting components revealed and the quality of the product will have quality equivalent to a single component pharmaceutical, except that it contains multiple components.

The advantage of developing products in this fashion is that the therapeutic values of natural substances are known ahead of time and potential toxicities may also be identified ahead of time.

This type of product can easily be adapted to a drug development program so that it can be treated as one of the leads to be moved forward for preclinical and clinical testing. The same approach as that outlined in examples 1 to 9 can be used to examine the source of toxicity and also components that are responsible for lowering toxicity.

EXAMPLE 12

Development of Red Clover for the Treatment of Osteoporosis

The objective of this example is to employ this invention to develop a popular herb for the treatment of postmenopausal osteoporosis. Like most of the well studied herbs in the market, Red clover's (*Trifolium pratense*) clinical efficacy is at best equivocal (Beck et al., 2005; Wuttke et al., 2007). Table 13 shows that the dosage of total phytoestrogens is approximately the same among commercial products (Beck et al., 2003). However, the quantity of individual components can vary anywhere between 2 to 12 times. There is no surprise that the performance of these products is not consistent. There are minute quantities of other phytoestrogens such as coumestrols and their contribution to the overall efficacy of the herb is not known. Interestingly, the major active components, genistein and daidzein are present in minute quantities in Red clover; however, their precursors, biochanin A and formononetin and their glycosides are present in much higher quantities. The questions are: 1. How do these ingredients work together; 2. Where do the metabolic conversions occur? 3. Are there any interactions between the components both pharmacokinetically and pharmacodynamically; 4. Are there other metabolites that would likely contribute to the overall efficacy of Red clover? 5. What is the best profile of ingredients that can be estimated using the present invention? 6. Are there any ways to improve the performance of Red clover?

TABLE 13

Composition of Phytoestrogens in Different Commercial Products

| Name | Daily dosage (total isoflavones, mg) | Biochanin A % wt | Formononetin % wt | Genistein % wt | Daidzein % wt |
|---|---|---|---|---|---|
| Promensil | 40 | 4.13 | 2.6 | 0.17 | 0.1 |
| Rimostil | 57 | 2.28 | 20.65 | 0.03 | 0.11 |
| Trinovin | 40 | 4.35 | 2.5 | 0.16 | 0.1 |
| Rotklee Activ tablets | N.A. | 2.37 | 4.8 | 0.17 | 0.36 |
| Red clover tablets | N.A. | 2.39 | 4.64 | 0.36 | 0.82 |
| Red clover | 40 | 4.6 | 2.5 | 0.13 | 0.13 |
| Isoflavones Boots | 40 | 4.62 | 2.67 | 0.16 | 0.15 |
| Menoflavon | 40-80 | 1.97 | 5.46 | 0.11 | 0.43 |

There are a lot of studies performed on Red clover and soy which contain high contents of phytoestrogens. The single component that received the most attention is genistein. It has been shown that genistein, 54 mg/day, given orally for a year, is as effective as hormone replacement therapy (Morabito et al., 2002). However, it is not known why there are not more confirmatory studies published.

In vitro permeability studies on five phytoestrogens, genistein, daidzein, glycitein, formononetin, biochanin A and prumetin have been performed using Caco-2 cell monolayer or Caco-2 cell lysates (Chen et al., 2005a). It has been found that these compounds are rapidly transported and metabolized. However, there is no information relating to their potential interactions among these species. Michaelis-Menten parameters for the glucuronide and sulfate conjugations for these five species were measured.

In Red clover, the most abundant phytoestrogens are formononetin, biochanin A and the glycosides of these phytoestrogens (FIG. 33). The most active components are genistein and daidzein, the metabolites of formononetin and biochanin A, respectively (Beck et al., 2003). The conversion from formononetin and biochanin A to daidzein and genistein, respectively, occurs in the colon via intestinal flora (Bowey et al., 2003). It is also found that a metabolite of daidzein, equol, formed in the microflora of the colon, is the most potent (Bowey et al., 2003; Setchell et al., 2005). Genistein and daidzein are present in minute quantities in Red clover extracts; usually it is less than 10% (Table 13).

The metabolism of glycosides of genistein and daidzein was measured using human intestinal and liver tissues (Day et al., 1998). The rate of metabolism of these two precursors of genistein and daidzein was individually measured.

The first-pass metabolism and enterohepatic cycling of genistein, daidzein, formononetin, biochanin A and prunetin were evaluated using a perfused rat intestinal model and microsomes prepared from rat liver, duodenum, jejunum, ileum and colon (Chen et al., 2005b). The rate of metabolism and absorption along the intestine was elucidated. Furthermore, the significance of liver metabolism and enterohepatic cycling was also reported. Again, there was no attempt to study a mixture.

Pharmacokinetic studies of biochanin A have been performed in rats (Moon et al., 2006) and Red clover in humans (Howes et al., 2002). Plasma phytoestrogens and their metabolites have been reported. Although these data are important, there is no estimation of the free concentration of the active moieties in the plasma; therefore, the concentration of active moieties at the site of action. It is difficult to deduce whether there are any significant interactions among these species.

The major soy isoflavones are genistein, daidzein and glycitein (Ewies, 2002). Since Red clover has a higher content of phytoestrogens, it has a better potential to treat disorders related to menopause (Beck et al., 2005). Unlike estradiol, phytoestrogens show higher binding affinity towards estrogen receptor beta (ERß) than estrogen receptor alpha (ERα) and recruit coregulators necessary for transcription of target genes selectively to ERß (Kuiper et al., 1998). The differential affinity for these receptors which are tissue specific may explain the specificity of these phytoestrogens (Enmark et al., 1997; Kuiper et al., 1997; Onoe et al., 1997; Wiik et al., 2003). The affinity for ERß may explain the beneficial effect of phytoestrogens for osteoporosis in menopause and lack of carcinogenic toxicity in the breast and other organs. Genistein has been found to have the highest affinity for ERß. This is the reason why this compound is the most studied and it is also the compound which is employed in a clinical trial (Morabito et al., 2002). Recent studies showed that daidzein is more potent in osteoblast formation in vitro (Li et al., 2005; Ge et al., 2006) than genistein. These recent results clearly show that more than one component in Red clover is responsible for its estrogenic effects. An innovative approach is required to identify the active ingredients instead of studying them individually.

Despite the higher content of phytoestrogens in Red clover, the proportion of genistein and daidzein is higher in soy. The reason why Red clover is preferred is because there is a much higher content of the precursors of genistein and daidzein, biochanin A and formononetin, respectively. The bioavailability of the aglycones of genistein and daidzein is less than 5%; this is mainly due to high first-pass gut and/or liver metabolism. Presumably, aglycone released in the colon by the enzymes of the intestinal flora would enhance the bioavailability of the aglycones because absorption from colon may partially bypass first-pass metabolism (Setchell et al., 2001).

The conversion of these precursors to their respective aglycones is dependent on metabolism by intestinal flora. The variability in intestinal flora content is high among individuals; it is hypothesized that the conversion of biochanin A and formononetin to their respective aglycones is highly inconsistent. This variability could have significant contribution to the erratic results observed clinically.

The importance of intestinal flora on phytoestrogen metabolism and bioavailability has been demonstrated recently (Ohta et al., 2002; Nielsen and Williamson, 2007). Immature intestinal flora have been shown to affect the bioavailability of isoflavones in soy (Nielsen and Williamson, 2007). Fructooligosaccharides (FOS) stimulate the growth of bifidobacteria, which cleave isoflavone conjugates to yield the corresponding aglycones and metabolites (Ohta et al., 2002). This study showed that the bioavailability of isoflavones was increased and this was due to an increase in ß-glucosidase activity which is responsible for the metabolism of the glycosides of isoflavones to their respective aglycones which are readily absorbed. It is hypothesized that healthy intestinal flora will not only promote isoflavone in Red clover absorption but also reduce inter-subject fluctuation of isoflavone blood levels. To optimize the function of Red clover, a prebiotic should be included.

The body of information in the literature can be used to validate part of the present invention. This will lend support to the accuracy of optimal ingredient profile estimation obtained from the present invention.

From the published studies, it is clear that the in vitro tools used are similar to that proposed in this invention. What is required is to repeat the same studies using a group of Red clover extracts which contains a diverse composition of individual phytoestrogens. The results from these studies will provide metabolic information and activity profiles of individual components and their potential interactions.

Metabolism by the intestinal flora appears to be the most important factor in the determination of the clinical activity of Red clover. Therefore, prebiotics, such as oligosaccharides and ß-glucans, and probiotics will be important in improving the consistency of active moieties production.

Using the concept of the present invention, it is highly feasible to obtain an optimal ingredient profile for Red clover for the treatment of osteoporosis. It is predicted that formononetin, biochanin A and their glycosides are the target for standardization. It is also predicted that the quantity of total formononetin (aglycone+glycosides) to be higher than that of total biochanin A (aglycone+glycosides). The incorporation of a prebiotic or probiotic to promote beneficial intestinal floral growth is required to enhance the activity of this new Red clover extract. The daily dosage of this new Red clover product will be between 50 to 200 mg total phytoestrogens per day.

REFERENCES

Ahlemeyer B and Krieglstein J (2003) Pharmacological studies supporting the therapeutic use of *Ginkgo biloba* extract for Alzheimer's disease. *Pharmacopsychiatry* 36 Suppl 1:S8-14.

Beck V, Rohr U and Jungbauer A (2005) Phytoestrogens derived from red clover: an alternative to estrogen replacement therapy? *J Steroid Biochem Mol Biol* 94:499-518.

Beck V, Unterrieder E, Krenn L, Kubelka W and Jungbauer A (2003) Comparison of hormonal activity (estrogen, androgen and progestin) of standardized plant extracts for large scale use in hormone replacement therapy. *J Steroid Biochem Mol Biol* 84:259-268.

Bernareggi A and Rowland M (1991) Physiologic modeling of cyclosporin kinetics in rat and man. *J Pharmacokinet Biopharm* 19:21-50.

Blumenthal M and Milot B (2004) Bioassays for testing activity and bioavailability of botanical products. Journal of the *American Botanical Council:* 48-51.

Bowey E, Adlercreutz H and Rowland I (2003) Metabolism of isoflavones and lignans by the gut microflora: a study in germ-free and human flora associated rats. *Food Chem Toxicol* 41:631-636.

Brazier N C and Levine M A (2003) Drug-herb interaction among commonly used conventional medicines: a compendium for health care professionals. *Am J Ther* 10:163-169.

Brightman F A, Leahy D E, Searle G E and Thomas S (2006a) Application of a generic physiologically based pharmacokinetic model to the estimation of xenobiotic levels in human plasma. *Drug Metab Dispos* 34:94-101.

Brightman F A, Leahy D E, Searle G E and Thomas S (2006b) Application of a generic physiologically based pharmacokinetic model to the estimation of xenobiotic levels in rat plasma. *Drug Metab Dispos* 34:84-93.

Brown R P, Delp M D, Lindstedt S L, Rhomberg L R and Beliles R P (1997) Physiological parameter values for physiologically based pharmacokinetic models. *Toxicol Ind Health* 13:407-484.

Chang T K, Chen J and Teng X W (2006) Distinct role of bilobalide and ginkgolide A in the modulation of rat CYP2B1 and CYP3A23 gene expression by *Ginkgo biloba* extract in cultured hepatocytes. *Drug Metab Dispos* 34:234-242.

Chen J, Lin H and Hu M (2005a) Absorption and metabolism of genistein and its five isoflavone analogs in the human intestinal Caco-2 model. *Cancer Chemother Pharmacol* 55:159-169.

Chen J, Wang S, Jia X, Bajimaya S, Lin H, Tam V H and Hu M (2005b) Disposition of flavonoids via recycling: comparison of intestinal versus hepatic disposition. *Drug Metab Dispos* 33:1777-1784.

Cheng Y, Wang Y and Wang X (2006) A causal relationship discovery-based approach to identifying active components of herbal medicine. *Comput Biol Chem* 30:148-154.

Chiou W L (1995) The validation of the intestinal permeability approach to predict oral fraction of dose absorbed in humans and rats. *Biopharm Drug Dispos* 16:71-75.

Chiou W L and Barve A (1998) Linear correlation of the fraction of oral dose absorbed of 64 drugs between humans and rats. *Pharm Res* 15:1792-1795.

Chiou W L, Ma C, Chung S M, Wu T C and Jeong H Y (2000) Similarity in the linear and non-linear oral absorption of drugs between human and rat. *Int J Clin Pharmacol Ther* 38:532-539.

Chou T C (2006) Theoretical basis, experimental design, and computerized simulation of synergism and antagonism in drug combination studies. *Pharmacol Rev* 58:621-681.

Davies B and Morris T (1993) Physiological parameters in laboratory animals and humans. *Pharm Res* 10:1093-1095.

Day A J, DuPont M S, Ridley S, Rhodes M, Rhodes M J, Morgan M R and Williamson G (1998) Deglycosylation of flavonoid and isoflavonoid glycosides by human small intestine and liver beta-glucosidase activity. *FEBS Lett* 436:71-75.

Dearden J C (2007) In silico prediction of ADMET properties: how far have we come? *Expert Opin Drug Metab Toxicol* 3:635-639.

Enmark E, Pelto-Huikko M, Grandien K, Lagercrantz S, Lagercrantz J, Fried G, Nordenskjold M and Gustafsson J A (1997) Human estrogen receptor beta-gene structure, chromosomal localization, and expression pattern. *J Clin Endocrinol Metab* 82:4258-4265.

Ewies A A (2002) Phytoestrogens in the management of the menopause: up-to-date. *Obstet Gynecol Surv* 57:306-313.

Fagerholm U (2007a) Prediction of human pharmacokinetics—evaluation of methods for prediction of hepatic metabolic clearance. *J Pharm Pharmacol* 59:803-828.

Fagerholm U (2007b) Prediction of human pharmacokinetics—gastrointestinal absorption. *J Pharm Pharmacol* 59:905-916.

Figueiredo M A T, Nowak R D and Wright S J (2007) Gradient Projection for Sparse Reconstruction: Application to Compressed Sensing and Other Inverse Problems, in: Selected Topics in Signal Processing. *IEEE Journal* 1:586-597.

Ge Y, Chen D, Xie L and zhang R (2006) Enhancing effect of daidzein on the differentiation and mineralization in mouse osteoblast-like MC3T3-E1 cells. *Yakugaku Zasshi* 126:651-656.

Grass G M, Leesman G D, Norris D A, Sinko P J and Wehrli J E (2003) Pharmacokinetic-based drug design tool and method, in (Office USPaT ed), Lion Bioscience AG, U.S.A.

Hallifax D, Rawden H C, Hakooz N and Houston J B (2005) Prediction of metabolic clearance using cryopreserved human hepatocytes: kinetic characteristics for five benzodiazepines. *Drug Metab Dispos* 33:1852-1858.

Hasegawa H (2004) Proof of the mysterious efficacy of ginseng: basic and clinical trials: metabolic activation of ginsenoside: deglycosylation by intestinal bacteria and esterification with fatty acid. *J Pharmacol Sci* 95:153-157.

Hasegawa H, Lee K S, Nagaoka T, Tezuka Y, Uchiyama M, Kadota S and Saiki I (2000) Pharmacokinetics of ginsenoside deglycosylated by intestinal bacteria and its transformation to biologically active fatty acid esters. *Biol Pharm Bull* 23:298-304.

Hasegawa H, Sung J H, Matsumiya S and Uchiyama M (1996) Main ginseng saponin metabolites formed by intestinal bacteria. *Planta Med* 62:453-457.

Hasegawa H and Uchiyama M (1998) Antimetastatic efficacy of orally administered ginsenoside Rb1 in dependence on intestinal bacterial hydrolyzing potential and significance of treatment with an active bacterial metabolite. *Planta Med* 64:696-700.

Hollman P C, van Trijp J M, Buysman M N, van der Gaag M S, Mengelers M J, de Vries J H and Katan M B (1997) Relative bioavailability of the antioxidant flavonoid quercetin from various foods in man. *FEBS Lett* 418:152-156.

Homma M, Oka K, Yamada T, Niitsuma T, Ihto H and Takahashi N (1992) A strategy for discovering biologically active compounds with high probability in traditional Chinese herb remedies: an application of saiboku-to in bronchial asthma. *Anal Biochem* 202:179-187.

Howes J, Waring M, Huang L and Howes L G (2002) Long-term pharmacokinetics of an extract of isoflavones from red clover (*Trifolium pratense*). *J Altern Complement Med* 8:135-142.

Hu Z, Yang X, Ho P C, Chan S Y, Heng P W, Chan E, Duan W, Koh H L and Zhou S (2005) Herb-drug interactions: a literature review. *Drugs* 65:1239-1282.

Khwaja T A and Friedman E P (2000) Pharmaceutical grade St. John's Wort, in *USPTO Patent Full-Text and Image Database* (USPTO ed), University of Southern California Pharmaprint Inc., USA.

Khwaja T A and Friedman E P (2002) Pharmaceutical grade botanical drugs, in *USPTO Patent Full-Text and Image Database* (USPTO ed), PharmaPrint, Inc. University of Southern California, U.S.A. Komoroski B J, Parise R A, Egorin M J, Strom S C and Venkataramanan R (2005)

Effect of the St. John's wort constituent hyperforin on docetaxel metabolism by human hepatocyte cultures. *Clin Cancer Res* 11:6972-6979.

Komoroski B J, Zhang S, Cai H, Hutzler J M, Frye R, Tracy T S, Strom S C, Lehmann T, Ang C Y, Cui Y Y and Venkataramanan R (2004) Induction and inhibition of cytochromes P450 by the St. John's wort constituent hyperforin in human hepatocyte cultures. *Drug Metab Dispos* 32:512-518.

Kuiper G G, Carlsson B, Grandien K, Enmark E, Haggblad J, Nilsson S and Gustafsson J A (1997) Comparison of the ligand binding specificity and transcript tissue distribution of estrogen receptors alpha and beta. *Endocrinology* 138:863-870.

Kuiper G G, Lemmen J G, Carlsson B, Corton J C, Safe S H, van der Saag P T, van der Burg B and Gustafsson J A (1998) Interaction of estrogenic chemicals and phytoestrogens with estrogen receptor beta. *Endocrinology* 139:4252-4263.

Kwak W J, Han C K, Son K H, Chang H W, Kang S S, Park B K and Kim H P (2002) Effects of Ginkgetin from *Ginkgo biloba* Leaves on cyclooxygenases and in vivo skin inflammation. *Planta Med* 68:316-321.

Lam J L and Benet L Z (2004) Hepatic microsome studies are insufficient to characterize in vivo hepatic metabolic clearance and metabolic drug-drug interactions: studies of digoxin metabolism in primary rat hepatocytes versus microsomes. *Drug Metab Dispos* 32:1311-1316.

Lartigue S, Bizais Y, Bruley des Varannes S, Cloarec D and Galmiche J P (1991) [Measurement of gastric emptying, intestinal transit time and colonic filling by scintiscan in healthy subjects]. *Gastroenterol Clin Biol* 15:379-385.

Lau Y Y, Sapidou E, Cui X, White R E and Cheng K C (2002) Development of a novel in vitro model to predict hepatic clearance using fresh, cryopreserved, and sandwich-cultured hepatocytes. *Drug Metab Dispos* 30:1446-1454.

Li X H, Zhang J C, Sui S F and Yang M S (2005) Effect of daidzin, genistin, and glycitin on osteogenic and adipogenic differentiation of bone marrow stromal cells and adipocytic transdifferentiation of osteoblasts. *Acta Pharmacol Sin* 26:1081-1086.

Liu Y and Yang L (2006) Early metabolism evaluation making traditional Chinese medicine effective and safe therapeutics. *J Zhejiang Univ Sci B* 7:99-106.

Lobell M and Sivarajah V (2003) In silico prediction of aqueous solubility, human plasma protein binding and volume of distribution of compounds from calculated pKa and AlogP98 values. *Mol Divers* 7:69-87.

Mahmoud F F, Haines D D, Abul H T, Abal A T, Onadeko B O and Wise J A (2004) In vitro effects of astaxanthin combined with ginkgolide B on T lymphocyte activation in peripheral blood mononuclear cells from asthmatic subjects. *J Pharmacol Sci* 94:129-136.

Mathews J M, Etheridge A S and Black S R (2002) Inhibition of human cytochrome P450 activities by kava extract and kavalactones. *Drug Metab Dispos* 30:1153-1157.

Mathews J M, Etheridge A S, Valentine J L, Black S R, Coleman D P, Patel P, So J and Burka L T (2005) Pharmacokinetics and disposition of the kavalactone kawain: interaction with kava extract and kavalactones in vivo and in vitro. *Drug Metab Dispos* 33:1555-1563.

Moda T L, Montanari C A and Andricopulo A D (2007) Hologram QSAR model for the prediction of human oral bioavailability. *Bioorg Med Chem* 15:7738-7745.

Mohutsky M A, Anderson G D, Miller J W and Elmer G W (2006) *Ginkgo biloba*: evaluation of CYP2C9 drug interactions in vitro and in vivo. *Am J Ther* 13:24-31.

Moon Y J, Sagawa K, Frederick K, Zhang S and Morris M E (2006) Pharmacokinetics and bioavailability of the isoflavone biochanin A in rats. *Aaps J* 8:E433-442.

Morabito N, Crisafulli A, Vergara C, Gaudio A, Lasco A, Frisina N, D'Anna R, Corrado F, Pizzoleo M A, Cincotta M, Altavilla D, Ientile R and Squadrito F (2002) Effects of genistein and hormone-replacement therapy on bone loss in early postmenopausal women: a randomized double-blind placebo-controlled study. *J Bone Miner Res* 17:1904-1912.

Newman D J, Cragg G M and Snader K M (2003) Natural products as sources of new drugs over the period 1981-2002. *J Nat Prod* 66:1022-1037.

Nielsen I L and Williamson G (2007) Review of the factors affecting bioavailability of soy isoflavones in humans. *Nutr Cancer* 57:1-10.

Norinder U and Bergstrom C A (2006) Prediction of ADMET Properties. *ChemMedChem* 1:920-937.

Ohta A, Uehara M, Sakai K, Takasaki M, Adlercreutz H, Morohashi T and Ishimi Y (2002) A combination of dietary fructooligosaccharides and isoflavone conjugates increases femoral bone mineral density and equol production in ovariectomized mice. *J Nutr* 132:2048-2054.

Onoe Y, Miyaura C, Ohta H, Nozawa S and Suda T (1997) Expression of estrogen receptor beta in rat bone. *Endocrinology* 138:4509-4512.

Pan J Y and Cheng Y Y (2006) Identification and analysis of absorbed and metabolic components in rat plasma after oral administration of 'Shuangdan' granule by HPLC-DAD-ESI-MS/MS. *J Pharm Biomed Anal* 42:565-572.

Pang P K T, Shan J J and Chiu K W (2000) Chemical and pharmacological standardization of herbal extracts, in *USPTO Patent Full-Text and Image Database* (USPTO ed), CV Technologies Inc., U.S.A.

Ruan L P, Chen S, Yu B Y, Zhu D N, Cordell G A and Qiu S X (2006) Prediction of human absorption of natural compounds by the non-everted rat intestinal sac model. *Eur J Med Chem* 41:605-610.

Schulz H U, Schurer M, Bassler D and Weiser D (2005) Investigation of pharmacokinetic data of hypericin, pseudohypericin, hyperforin and the flavonoids quercetin and isorhamnetin revealed from single and multiple oral dose studies with a *hypericum* extract containing tablet in healthy male volunteers. *Arzneimittelforschung* 55:561-568.

Setchell K D, Brown N M, Desai P, Zimmer-Nechemias L, Wolfe B E, Brashear W T, Kirschner A S, Cassidy A and Heubi J E (2001) Bioavailability of pure isoflavones in healthy humans and analysis of commercial soy isoflavone supplements. *J Nutr* 131:1362 S-1375S.

Setchell K D, Clerici C, Lephart E D, Cole S J, Heenan C, Castellani D, Wolfe B E, Nechemias-Zimmer L, Brown N M, Lund T D, Handa R J and Heubi J E (2005) S-equol, a potent ligand for estrogen receptor beta, is the exclusive enantiomeric form of the soy isoflavone metabolite produced by human intestinal bacterial flora. *Am J Clin Nutr* 81:1072-1079.

Tam Y K and Anderson K E (2000) Simulated biological dissolution and absorption system, in *USPTO Patent Full-Text and Image Database* (USPTO ed), U.S.A.

Venkataramanan R, Komoroski B and Strom S (2006) In vitro and in vivo assessment of herb drug interactions. *Life Sci* 78:2105-2115.

Venkataramanan R, Ramachandran V, Komoroski B J, Zhang S, Schiff P L and Strom S C (2000) Milk thistle, a herbal supplement, decreases the activity of CYP3A4 and uridine diphosphoglucuronosyl transferase in human hepatocyte cultures. *Drug Metab Dispos* 28:1270-1273.

Wang Y, Wang X and Cheng Y (2006) A computational approach to botanical drug design by modeling quantitative composition-activity relationship. *Chem Biol Drug Des* 68:166-172.

Wiik A, Glenmark B, Ekman M, Esbjornsson-Liljedahl M, Johansson O, Bodin K, Enmark E and Jansson E (2003) Oestrogen receptor beta is expressed in adult human skeletal muscle both at the mRNA and protein level. *Acta Physiol Scand* 179:381-387.

Williamson E M (2001) Synergy and other interactions in phytomedicines. *Phytomedicine* 8:401-409.

Williamson E M (2005) Interactions between herbal and conventional medicines. *Expert Opin Drug Saf* 4:355-378.

Wuttke W, Jarry H and Seidlova-Wuttke D (2007) Isoflavones—safe food additives or dangerous drugs? *Ageing Res Rev* 6:150-188.

Yan R, Ko N L, Li S L, Tam Y K and Lin G (2008) Pharmacokinetics and metabolism of ligustilide, a major bioactive component in Rhizoma Chuanxiong, in the rat. *Drug Metab Dispos* 36:400-408.

Yan R, Lin G, Ko N L and Tam Y K (2007) Low Oral Bioavailability and Pharmacokinetics of Senkyunolide A, a Major Bioactive Component in Rhizoma Chuanxiong, in the Rat. *Ther Drug Monit* 29:49-56.

Yim J S, Kim Y S, Moon S K, Cho K H, Bae H S, Kim J J, Park E K and Kim D H (2004) Metabolic activities of ginsenoside Rb1, baicalin, glycyrrhizin and geniposide to their bioactive compounds by human intestinal microflora. *Biol Pharm Bull* 27:1580-1583.

Zhang J L, Cui M, He Y, Yu H L and Guo D A (2005) Chemical fingerprint and metabolic fingerprint analysis of Danshen injection by HPLC-UV and HPLC-MS methods. *J Pharm Biomed Anal* 36:1029-1035.

Zhou S, Huang M, Xu A, Yang H, Duan W and Paxton J W (2005) Prediction of herb-drug metabolic interactions: a simulation study. *Phytother Res* 19:464-471.

What is claimed is:

1. A method of preparing a herbal composition comprising multiple components for drug formulations, the method comprises the steps of:

a) preparing multiple samples having different random concentrations of a herbal mixture that comprises multiple components, each of said sample comprises the same multiple components, said samples further comprise multiple doses of the mixture, wherein the identities of or interactions among the components are not known a priori;

b) obtaining a dataset comprising pharmacodynamic parameters describing the dose-response of said samples of mixture;

c) performing linear modeling on said dataset to identify the components having strong correlation with the response as potential active components; said modeling system comprises $$r \approx \bar{r} + \sum_i w_i(d_i - \bar{d}_i) + \sum_i w'_i(d_i - \bar{d}_i)^2 +$$

-continued
$$\sum_{i,j} w_{i,j}(d_i - \bar{d}_i)(d_j - \bar{d}_j) \min_{w_i, w'_i, w_{i,j}} \left\{ r - \left[ \bar{r} + \sum_i w_i(d_i - \bar{d}_i) + \sum_i w'_i(d_i - \bar{d}_i)^2 + \sum_{i,j} w_{i,j}(d_i - \bar{d}_i)(d_j - \bar{d}_j) \right] \right\}^2$$

wherein r is linearized response, $\bar{r}$ is average linearized response; $w_i$ is weight of the $i^{th}$ component, $w'_i$ is weight of the non-linear self-interaction behavior of the $i^{th}$ component, $d_i$ is the dose of the $i^{th}$ component, $\bar{d}_i$ and $\bar{d}_j$ are average doses of the $i^{th}$ and $j^{th}$ component, and $w_{i,j}$ is the weight of the interacting pair, $$\min_{w_i, w'_i, w_{i,j}}$$

is a minimization procedure to minimize the difference between r and said first modeling system by varying $w_i$, $w'_i$, $w_{i,j}$, wherein said first modeling system generates outputs comprising (i) optimal weights $\alpha_i$ and $\beta_{i,j}$, which are optimal values of $w_i$ and $w'_i$ and $w_{i,j}$ obtained from said minimization procedure, and (ii) total dose of the components D, which is defined as $$\sum_{i=1}^{n} d_i;$$

d) Using Bootstrapping approach to repeat steps b)-c) to refine the optimal weights $\alpha_i$ and $\beta_{i,j}$ and potential active components;

e) using in vitro assays or in silico methods to obtain parameters describing the rate of elimination of said potential active components from (d) and their active metabolites in a plurality of mammalian tissue systems;

f) using in vitro assays or in silico methods to obtain parameters describing distribution of said potential active components from (d) and their active metabolites in a plurality of mammalian tissue systems;

g) estimating the effect-time relationship of the potential active components by incorporating said parameters of (e) and (f);

h) performing Subset-selection principal component analysis to infer the final set of active components based on parameters from d), e), f) and g);

i) inputting the optimal weights, $\alpha_i$ and $\beta_{i,j}$, from (d) of final set of active components from h) into a second modeling system that comprises $$A = \alpha_0 + \sum_{i=1}^{n} \alpha_i x_i + \sum_{i=1}^{n}\sum_{j=1}^{n} \beta_{i,j} x_i x_j \max_x \alpha_0 + \sum_{i=1}^{n} \alpha_i x_i + \sum_{i=1}^{n}\sum_{j=1}^{n} \beta_{i,j} x_i x_j$$

s.t.

$$\sum_{i=1}^{n} x_i = 1$$

$$x_i \geq 0, \forall i$$

wherein, A is estimated response generated by said active components per total dose, $\alpha_0$ is an average linearized response per total dose, $x_i$ and $x_j$ are defined as $d'_i/D$ and $d'_j/D$ respectively, which are fractions of said total dose D contributed by the $i^{th}$ and $j^{th}$ component respectively, and wherein $$D = \sum_{i=1}^{n} d'_i,$$

$$\max_{x}$$

is a maximization procedure achieved by varying $x_i$, $\forall_i$ is for all i values, wherein said second modeling system generates outputs comprising dosages of active components that generate maximal response; and j) using dosages of active components that generate the maximal response from (i) to prepare a herbal composition comprising multiple components, wherein the dosages for said multiple components are obtained from said dosages of active components that generate the maximal response.

2. The method of claim 1, wherein the pharmacodynamic parameters describing the response of an individual component are determined through receptor binding assays, enzymatic assays, biochemical response assays, or assays with isolated tissues or organs.

3. The method of claim 1, wherein said outputs of the first and second modeling systems comprise pharmacokinetic concentration-time profiles and response-time profiles for the components, or comprise pharmacodynamic descriptions on the synergism or inhibition among the components.

4. The method of claim 1, wherein the mammalian tissue systems are selected from the group consisting of gastrointestinal tract, liver, kidney, blood, mammary gland, uterus, prostate, brain, and bone.

5. The method of claim 1, wherein the rate of elimination comprises one or more parameters selected from the group consisting of rate of metabolism, rate of absorption, and rate of degradation.

6. The method of claim 5, wherein the rate of absorption is determined by rate of permeability measured using cultured cells or intestinal tissues.

7. The method of claim 4, wherein determining the rate of elimination in gastrointestinal tract comprises assays using artificial gastric or intestinal juice, intestinal flora or intestinal microsomes.

* * * * *

UNITED STATES PATENT AND TRADEMARK OFFICE
CERTIFICATE OF CORRECTION

PATENT NO. : 10,114,931 B2
APPLICATION NO. : 14/327529
DATED : October 30, 2018
INVENTOR(S) : Yun Kau Tam and Jack Adam Tuszynski It is certified that error appears in the above-identified patent and that said Letters Patent is hereby corrected as shown below:

On the Title Page

Under abstract "7 Claims, 36 Drawing Sheets" should read --9 Claims, 36 Drawing Sheets--.

In the Claims

Column 49, Line 46-Column 52, Line 26, (approx.) please replace the claims with the claims as shown below:

1. A method of preparing a herbal composition comprising multiple components for drug formulations, the method comprises the steps of:
   a) preparing multiple samples of a herbal mixture that comprises multiple components, each of said sample comprises the same multiple components with randomized concentrations, said samples further comprise multiple doses of the mixture, wherein the identities of or interactions among the components are not known a priori;
   b) using *in vitro* assays or *in silico* methods to obtain parameters describing the rate of elimination of said components and their active metabolites in a plurality of mammalian tissue systems;
   c) using *in vitro* assays or *in silico* methods to obtain parameters describing distribution of said components and their active metabolites in a plurality of mammalian tissue systems;
   d) obtaining pharmacodynamic parameters describing the response of said samples of mixture;
   e) performing Subset-Selection Principal Component Analysis to reduce dimensionality of the parameters from (b) to (d), Signed and Sealed this
Twelfth Day of February, 2019

Andrei Iancu
*Director of the United States Patent and Trademark Office* thereby generating parameters for active components in the mixture;

f) inputting the parameters for active components from (e) into a first modeling system to estimate optimal weights of the active components, said modeling system comprises $$r \approx \bar{r} + \sum_i w_i (d_i - \bar{d}_i) + \sum_i w'_i (d_i - \bar{d}_i)^2 + \sum_{i,j} w_{i,j} (d_i - \bar{d}_i)(d_j - \bar{d}_j)$$

$$\min_{w_i, w'_i, w_{i,j}} \left\{ r - \left[ \bar{r} + \sum_i w_i (d_i - \bar{d}_i) + \sum_i w'_i (d_i - \bar{d}_i)^2 + \sum_{i,j} w_{i,j} (d_i - \bar{d}_i)(d_j - \bar{d}_j) \right] \right\}^2$$

wherein $r$ is linearized response, $\bar{r}$ is average linearized response; $w_i$ is weight of the $i^{th}$ component, $w'_i$ is weight of the non-linear self-interaction behavior of the $i^{th}$ component, $d_i$ is the dose of the $i^{th}$ component, $\bar{d}_i$ and $\bar{d}_j$ are average doses of the $i^{th}$ and $j^{th}$ component, and $w_{i,j}$ is the weight of the interacting pair, $\min_{w_i, w'_i, w_{i,j}}$ is a minimization procedure to minimize the difference between r and said first modeling system by varying $w_i$, $w'_i$, $w_{i,j}$,
wherein said first modeling system generates outputs comprising (i) optimal weights $\alpha_i$ and $\beta_{i,j}$, which are optimal values of $w_i$ and $w'_i$ and $w_{i,j}$ obtained from said minimization procedure, and (ii) total dose of the components D, which is defined as $\sum_{i=1}^{n} d_i$;

g) inputting the optimal weights, $\alpha_i$ and $\beta_{i,j}$, from (f) into a second modeling system that comprises $$A = \alpha_0 + \sum_{i=1}^{n} \alpha_i x_i + \sum_{i=1}^{n} \sum_{j=1}^{n} \beta_{i,j} x_i x_j$$

$$\max_{x} \quad \alpha_0 + \sum_{i=1}^{n} \alpha_i x_i + \sum_{i=1}^{n} \sum_{j=1}^{n} \beta_{i,j} x_i x_j$$

$$s.t. \quad \sum_{i=1}^{n} x_i = 1$$
$$x_i \geq 0, \forall i$$

wherein, $A$ is estimated response generated by said active components per total dose, $\alpha_0$ is an average linearized response per total dose, $x_i$ and $x_j$ are defined as $d'_i/D$ and $d'_j/D$ respectively, which are fractions of said total dose D contributed by the $i^{th}$ and $j^{th}$ component respectively, and wherein $D = \sum_{i=1}^{n} d'_i$, $\max_{x}$ is a maximization procedure achieved by varying $x_i$, $\Box_i$ is for all $i$ values,
wherein said second modeling system generates outputs comprising dosages of active components that generate maximal response; and h) using dosages of active components that generate the maximal response from (g) to prepare a herbal composition comprising multiple components, wherein the dosages for said multiple components are obtained from said dosages of active components that generate the maximal response.

2. The method of claim 1, wherein the herbal mixture is from a natural source or a synthetic source.

3. The method of claim 2, wherein the natural source is a botanical source.

4. The method of claim 1, wherein the pharmacodynamic parameters describing the response of an individual component are determined through receptor binding assays, enzymatic assays, biochemical response assays, or assays with isolated tissues or organs.

5. The method of claim 1, wherein said outputs of the first and second modeling systems comprise pharmacokinetic concentration-time profiles and response-time profiles for the components, or comprise pharmacodynamic descriptions on the synergism or inhibition among the components.

6. The method of claim 1, wherein the mammalian tissue systems are selected from the group consisting of gastrointestinal tract, liver, kidney, blood, mammary gland, uterus, prostate, brain, and bone.

7. The method of claim 1, wherein the rate of elimination comprises one or more parameters selected from the group consisting of rate of metabolism, rate of absorption, and rate of degradation.

8. The method of claim 7, wherein the rate of absorption is determined by rate of permeability measured using cultured cells or intestinal tissues.

9. The method of claim 6, wherein determining the rate of elimination in gastrointestinal tract comprises assays using artificial gastric or intestinal juice, intestinal flora or intestinal microsomes.